United States Patent
Rzymski et al.

(10) Patent No.: US 9,745,299 B2
(45) Date of Patent: Aug. 29, 2017

(54) SUBSTITUTED TRICYCLIC BENZIMIDAZOLES AS KINASE INHIBITORS

(71) Applicant: SELVITA SA, Kraków (PL)

(72) Inventors: Tomasz Rzymski, Elblag (PL); Adrian Zarebski, Kraków (PL); Agnieszka Dreas, Poznan (PL); Karolina Osowska, Kraków (PL); Katarzyna Kucwaj, Kraków (PL); Joanna Fogt, Leszno (PL); Marek Cholody, Kraków (PL); Michal Galezowski, Skierniewice (PL); Wojciech Czardybon, Mikolów (PL); Raymond Horvath, Montreal (CA); Katarzyna Wiklik, Kraków (PL); Mariusz Milik, Kraków (PL); Krzysztof Brzózka, Kraków (PL)

(73) Assignee: SELVITA SA, Cracow (PL)

( * ) Notice: Subject to any disclaimer, the term of this patent is extended or adjusted under 35 U.S.C. 154(b) by 0 days.

(21) Appl. No.: 14/441,785

(22) PCT Filed: Nov. 7, 2013

(86) PCT No.: PCT/EP2013/073311
§ 371 (c)(1),
(2) Date: May 8, 2015

(87) PCT Pub. No.: WO2014/072435
PCT Pub. Date: May 15, 2014

(65) Prior Publication Data
US 2015/0274726 A1    Oct. 1, 2015

(30) Foreign Application Priority Data
Nov. 8, 2012 (GB) .................................. 1220157.0

(51) Int. Cl.
| | | |
|---|---|---|
| *C07D 471/06* | (2006.01) | |
| *A61K 31/4745* | (2006.01) | |
| *C07D 487/06* | (2006.01) | |
| *A61K 45/06* | (2006.01) | |
| *A61K 31/496* | (2006.01) | |
| *A61K 31/5377* | (2006.01) | |
| *A61K 31/541* | (2006.01) | |
| *A61K 31/55* | (2006.01) | |
| *A61K 31/551* | (2006.01) | |

(52) U.S. Cl.
CPC ........ *C07D 471/06* (2013.01); *A61K 31/4745* (2013.01); *A61K 31/496* (2013.01); *A61K 31/5377* (2013.01); *A61K 31/541* (2013.01); *A61K 31/55* (2013.01); *A61K 31/551* (2013.01); *A61K 45/06* (2013.01); *C07D 487/06* (2013.01)

(58) Field of Classification Search
CPC .......................... C07D 471/06; A61K 31/4745
USPC .............................................. 546/79; 514/290
See application file for complete search history.

(56) References Cited

U.S. PATENT DOCUMENTS

| | | | |
|---|---|---|---|
| 6,794,382 | B2 | 9/2004 | Barth et al. |
| 2012/0071477 | A1 | 3/2012 | Porter et al. |
| 2012/0202785 | A1* | 8/2012 | Heald .................. C07D 401/12 514/210.18 |

FOREIGN PATENT DOCUMENTS

| | | |
|---|---|---|
| EP | 0 405 442 A1 | 1/1991 |
| EP | 0 700 913 A1 | 3/1996 |
| WO | WO 02/12239 A1 | 2/2002 |
| WO | WO 03/051879 A1 | 6/2003 |
| WO | WO 2007/018998 A2 | 2/2007 |

OTHER PUBLICATIONS

Elderfield, R.C., et al., "A study of the synthesis of plasmochin by the reductive amination method with Raney nickel," *J Am Chem Soc.* 70(1):40-4, American Chemical Society, United States (1948).
Eiderfield, R.C., et al., "Synthesis of Bz-polymethoxy-8-aminoquinolines and some derivatives thereof," *J. Org. Chem.*, 17 (3):358-370, American Chemical Society, United States (1952).
Simonov, A.M., and Poludnenko. V.G., "Derivatives of 5,6-dihydro-4H-imidazo[4, 5, 1-i,j] quinoline. III. Substitution reactions in a 5, 6-dihydro-4H-imidazo [4, 5, 1-i-j] quinolone,"(English Abstract) *Khimiya Geterotsiklicheskikh Soedinenii* 2: 242-6, Latvian Institute of Organic Synthesis, Latvia (1972) (STN CAPLUS abstract No. 1972:140645)
Werbel, et al., "Synthesis of 5,6-dihydro-8-methoxy-4H-imidazo[4,5,1-ij]quinolines and some related ring systems," *Journal of Heterocyclic Chemistry* 5(3):371 378, Wiley Online Library (1968).

(Continued)

*Primary Examiner* — Rita Desai
(74) *Attorney, Agent, or Firm* — Sterne, Kessler, Goldstein and Fox P.L.L.C.

(57) ABSTRACT

Disclosed are substituted tricyclic benzimidazoles compounds as defined herein in formula (I) or pharmaceutically acceptable salts thereof. The compounds of the invention selectively inhibit CDK8 and are therefore useful for treating diseases related to this kinase, especially colorectal and melanoma cancers and other solid and hemathological malignancies, autoimmune diseases and inflammatory diseases. Also disclosed are processes for preparing these compounds.

(I)

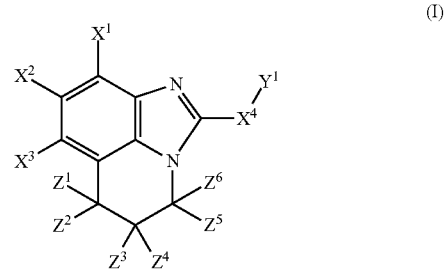

18 Claims, 4 Drawing Sheets

(56) References Cited

OTHER PUBLICATIONS

Combined Search and Examination Report for UK Patent Application No. GB1220157.0, UK Intellectual Property Office, England, dated Apr. 12, 2013, 5 pages.
Adler, A.S., et al., "CDK8 Maintains Tumor Dedifferentiation and Embryonic Stem Cell Pluripotency," Cancer Research 72(8):2129-2139, American Association for Cancer Research, United States (2012).
Chou, T.C., "Drug Combination Studies and their Synergy Quantification Using the Chou-Talalay Method," Cancer Research 70(2):440-446, American Association for Cancer Research, United States (2010).
Donner, A.J., et al., "CDK8 is a Positive Regulator of Transcriptional Elongation within the Serum Response Network," Nature Structural and Molecular Biology 17(2):194-201, Nature Publising Group, United States (2010).
Drogat, J., et al., "Cdk11-CyclinL Controls the Assembly of the RNA Polymerase II Mediator Complex," Cell Reports 2(5):1068-1076, Cell Press, United States (2012).
Firestein, R., et al., "CDK8 Expression in 470 Colorectal Cancers in Relation to Beta-catenin Activation, Other Molecular Alterations and Patient Survival," International Journal of Cancer 126(12):2863-2873, Wiley-Liss, United States (2010).
Firestein, R., et al., "CDK8 is a Colorectal Cancer Oncogene that Regulates β-catenin Activity," Nature 455(7212):547-551, Nature Publishing Group, England (2008).
Gray, N., et al., "ATP-site Directed Inhibitors of Cyclin-dependent Kinases," Current Medicinal Chemistry 6(9):859-875, Bentham Science Publishers, Netherlands (1999).
International Search Report and Written Opinion for International Application No. PCT/EP2013/073311, European Patent Office, Netherlands, dated Dec. 16, 2013, 8 pages.
Kapoor, A., et al., "The Histone Variant MacroH2A Suppresses Melanoma Progression through Regulation of CDK8," Nature 468(7327):1105-1109, Macmillan Publishers Ltd., England (2010).
MacKeigan, J.P., et al., "Sensitized RNAi Screen of Human Kinases and Phosphatases Identifies New Regulators of Apoptosis and Chemoresistance," Nature Cell Biology 7(6):591-600, Macmillan Magazines Ltd., England (2005).
Malumbres, M. and Barbacid, M., "Cell Cycle, CDKs and Cancer: A Changing Paradigm," Nature Reviews. Cancer 9(3):153-166, Macmillan Publishers Ltd., England (2009).
Morgan, D.O., "Principles of CDK Regulation," Nature 374(6518):131-134, Nature Publishing Group, England (1995).
Pines, J., "The Cell Cycle Kinases," Seminars in Cancer Biology 5(4):305-313, Academic Press, England (1994).
Porter, D.C., et al., "Cyclin-dependent Kinase 8 Mediates Chemotherapy-induced Tumor-promoting Paracrine Activities," Proceedings of the National Academy of Sciences, USA 109(34):13799-13804, National Academy of Sciences, United States (2012).
Sausville, E.A., "Complexities in the Development of Cyclin-dependent Kinase Inhibitor Drugs," Trends in Molecular Medicine 8(4 Suppl):S32-S37, Elsevier Science Ltd., England (2002).
Sherr, C.J. and Roberts, J.M., "CDK Inhibitors: Positive and Negative Regulators of G1-phase Progression," Genes and Development 13(12):1501-1512, Cold Spring Harbor Laboratory Press, United States (1999).
Westerling, T., et al., "Cdk8 Is Essential for Preimplantation Mouse Development," *Mol Cell Biol.* 27(17):6177-82, American Society for Microbiology, United States (2007).

\* cited by examiner

SUBSTITUTED TRICYCLIC BENZIMIDAZOLES AS KINASE INHIBITORS

FIELD OF THE INVENTION

The present invention relates to substituted tricyclic benzimidazoles and pharmaceutically acceptable salts thereof. The present invention further relates to pharmaceutical compositions comprising such compounds, wherein the pharmaceutical compositions are particularly useful in the treatment of CDK8-related disorders such as cancers (e.g. colorectal cancer, melanoma, lung cancer and other solid and hematological malignancies), autoimmune diseases and inflammatory diseases.

BACKGROUND OF THE INVENTION

Protein kinases are enzymes dedicated to transfer phosphate groups from ATP to a substrate protein. Phosphorylation of the targeted proteins results in a functional change of their activity and can also modify the association with other proteins, trafficking and subcellular localization. It is estimated that up to 30% of all proteins can be modified by kinases. For this reason, kinases are key regulators of the majority of cellular pathways, especially those involved in signal transduction. Phosphorylation is a mode of transmission of information on biomolecular level.

There are receptor protein kinases, which are located in cellular membranes, and non-receptor protein kinases, which are located in the cytoplasm.

Cyclin dependent protein kinases (CDKs) are non-receptor kinases that require cyclin for their activity. CDKs comprise a family of Ser/Thr kinases divided into two groups, including the cell cycle CDKs, which orchestrate cell cycle progression, and the transcriptional CDKs, which contribute to transcriptional regulation [Malumbres et al., *Nat Rev Cancer* 9: 153-166, (2009); Sausville, *Trends Mol Med* 8: S32-S37, (2002)]. The first group encompasses core components of the cell cycle machinery, including cyclin D-dependent kinases 4 and 6, as well as cyclin E-CDK2 complexes, which sequentially phosphorylate the retinoblastoma protein, Rb, to facilitate the G1/S transition. Cyclin A-dependent kinases 2 and 1 are required for orderly S phase progression, whereas cyclin BCDK1 complexes control the G2/M transition and participate in mitotic progression [Pines, *Semin Cancer Biol* 5: 305-313, (1994)]. The functional activation of cell cycle CDKs depends in part on the formation of heterodimeric cyclin-CDK complexes, which may be modulated by association with endogenous Cip/Kip or INK4 inhibitors [Sherr et al., *Genes Dev* 13: 1501-1512, (1999)]. CDKs are also regulated by phosphorylation, including positive events directed by CDK-activating kinase (CAK, cyclin H/CDK7/MAT1) and negative phosphorylation events [Morgan, *Nature* 374: 131-134, (1995)].

The transcriptional CDKs, including cyclin H-CDK7, cyclin C-CDK8 and cyclin T-CDK9 (P-TEFb), promote initiation and elongation of nascent RNA transcripts by phosphorylating the carboxy-terminal domain (CTD) of RNA polymerase II. CDK8 is a part of the Mediator complex that functions as a transcriptional coactivator in all eukaryotes. In addition, two other kinase components of this complex CDK11 and CDK19 (which is structurally similar to CDK8) were described [Drogat et al. *Cell Reports* 2: 1-9, (2012)]. CDK8 functions as an oncoprotein, especially in colorectal cancers where it regulates activity of β-catenin, and there is considerable interest in developing drugs specifically targeting the CDK8 kinase activity [Firestein et al., Nature 7212: 547-551, (2008)].

CDK8 resides on a region of Chr. 13 that is known to undergo chromosomal gain in 40-60% of colorectal cancers. Moreover, high CDK8 expression was detected in 70% tumors by immunohistochemistry [Adler et al., Cancer Res. 72: 2129-2139, (2008)]. Colorectal cancer cells that express elevated CDK8 levels are highly dependent on its expression for proliferation [Firestein et al., Nature 7212: 547-551, (2008)]. CDK8 was required to promote rapid tumor growth as well as maintain the CRC tumors in an undifferentiated state. CDK8 expression induced focus formation, anchorage-independent colony growth and tumor formation in immunodeficient animals [Adler et al., Cancer Res. 72: 2129-2139, (2008)].

CDK8 levels are also elevated in response to loss of the histone variant macroH2A (mH2A) [Kapoor et al. Nature 468(7327): 1105-1109, (2011)]. Loss of histone isoform mH2A promotes malignant phenotype of melanoma cells. Tumor promoting functions of mH2A are at least partially mediated by up-regulation of CDK8. Knockdown of CDK8 was able to suppress the enhanced proliferation of melanoma cells induced by mH2A loss in vitro and in vivo.

CDK8 is also involved in secretory activity of senescent cells in response to chemotherapy. Selective inhibition of CDK8 and CDK19 repressed expression of certain cytokines and growth factors which are released in response to chemotherapy treatment and stimulate tumor growth [Porter et al., PNAS (34) 109: 13799-13804, (2012)]. The role of CDK8 in expression of proinflammatory cytokines such as TNFα and IL6, upon stimulation with exogenous and endogenous factors, such as LPS and other TLR agonists, was so far not reported in the literature to the best of our knowledge. Therefore CDK8 can be considered as a novel, emerging target in the treatment of autoimmune and inflammatory disorders.

Suppression of CDK8 kinase is also an attractive strategy for targeting colorectal cancers, including these resistant to anti-EGFR therapies due to activating mutations in KRAS and BRAF downstream in the pathway [Donner et al., Nat Struct Mol Biol. 17: 194-201, (2010)].

In contrast CDK8 deficiency in cultured "normal" metazoan cells did not affect cell viability [Westerling et al., Nature. 382:638-42 (1996)]. Hence, inhibitors of CDK8 are considered as promising agents for cancer.

High expression of CDK8 significantly increased colon cancer-specific mortality [Firestein et al., Int J Cancer 126 (12): 2863-2873, (2010)] and decreased duration of relapse-free survival in patients with breast and ovarian cancer [Porter et al., PNAS (34) 109: 13799-13804, (2012)].

The majority of small molecule inhibitors block kinases by binding to the ATP binding site, which is highly conserved, especially in the family of CDKs. Most of the known CDK inhibitors are, however, rather unselective and display undesired side effects. Small molecules which selectively target the transcriptional kinase CDK8 are thus desirable when treating e.g. cancer, autoimmune and inflammatory diseases.

OBJECTS AND SUMMARY OF THE INVENTION

The inventors of the present invention inter alia surprisingly found that compounds of formula (I) as defined herein exhibit a selective inhibitory activity against CDK8.

In a first aspect, the present invention refers to compounds of formula (I)

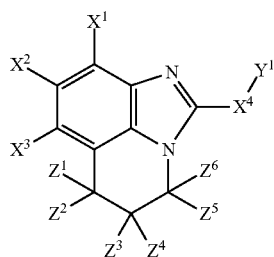

(I)

wherein

X¹, X² and X³ are each independently selected from the group consisting of H, F, Cl, Br, I, —OT¹, —N(T²)(T³), —NHC(=O)T⁴, nitro, cyano, cyclopropyl and —C$_{1-3}$alkyl, with the proviso that at least two substituents selected from X¹, X² and X³ are not H;

Z¹ and Z² are either taken together to form an oxo group at the carbon atom to which they are attached; or Z¹ and Z² are each independently selected from the group consisting of H, —C$_{1-6}$alkyl, —OT¹ and —N(T²)(T³);

Z³ and Z⁴ are either taken together to form an oxo group at the carbon atom to which they are attached; or Z³ and Z⁴ are each independently selected from the group consisting of H, —C$_{1-6}$alkyl, —OT¹ and —N(T²)(T³);

Z⁵ and Z⁶ are either taken together to form an oxo group at the carbon atom to which they are attached; or Z⁵ and Z⁶ are each independently selected from the group consisting of H, —C$_{1-6}$alkyl, —OT¹ and —N(T²)(T³);

X⁴ is either absent or selected from the group consisting of —NR⁴—, —N(R⁴)(CH₂)—, —C(=O)NH— and —C(=O)—;

R⁴ is selected from H and —C$_{1-6}$alkyl;

Y¹ is selected from the group consisting of H, —C$_{1-6}$alkyl and a 4- to 7-membered saturated or unsaturated aromatic carbocycle or heterocycle, with the proviso that the point of attachment on said heterocycle is carbon if X⁴ is —NR⁴— or —C(=O)NH—, wherein said —C$_{1-6}$alkyl is optionally substituted with one or more substituents independently selected from —OT¹, —ST¹, —N(T²)(T³) and a 5- to 6-membered saturated heterocycle, and wherein said 4- to 7-membered saturated or unsaturated aromatic carbocycle or heterocycle is optionally substituted with one or more substituents independently selected from F, Cl, Br, I, —C(=O)H, —OT¹, —N(T²)(T³), —C(=O)N(T²)(T³), —C(=O)OT¹, —ST¹ and —C$_{1-3}$alkyl, wherein said —C$_{1-3}$alkyl is optionally substituted with one or more substituents independently selected from —OT¹ and —N(T²)(T³);

T¹, T² and T³ are each independently selected from H and —C$_{1-6}$alkyl optionally substituted with one or more substituents independently selected from —N(T⁵)(T⁶), —OT⁷, —ST⁷, nitro, cyano, —C(=O)OT⁷, —C(=O)N(T⁵)(T⁶), —OC(=O)N(T⁵)(T⁶), —S(=O)₂T⁷, —S(=O)₂OT⁸ and —S(=O)₂N(T⁵)(T⁶);

T⁴ is —C$_{1-6}$alkyl optionally substituted with one or more substituents independently selected from —N(T⁵)(T⁶), —OT⁷, —ST⁷, nitro, cyano, —C(=O)OT⁷, —C(=O)N(T⁵)(T⁶), —OC(=O)N(T⁵)(T⁶), —S(=O)₂T⁸, —S(=O)₂OT⁷ and —S(=O)₂N(T⁵)(T⁶);

T⁵, T⁶ and T⁷ are each independently selected from H and —C$_{1-6}$alkyl optionally substituted with one or more substituents independently selected from amino, hydroxyl, thiol, nitro and cyano; and T⁸ is selected from —C$_{1-6}$alkyl optionally substituted with one or more substituents independently selected from amino, hydroxyl, thiol, nitro and cyano;

or a pharmaceutically acceptable salt thereof.

In a particularly preferred embodiment, Y¹ is a 4- to 7-membered saturated or unsaturated aromatic carbocycle or heterocycle, with the proviso that the point of attachment on said heterocycle is carbon if X⁴ is —NR⁴— or —C(=O)NH—, wherein said 4- to 7-membered saturated or unsaturated aromatic carbocycle or heterocycle is optionally substituted with one or more substituents independently selected from F, Cl, Br, I, —C(=O)H, —OT¹, —N(T²)(T³), —C(=O)N(T²)(T³), —C(=O)OT¹, —ST¹ and —C$_{1-3}$alkyl, wherein said —C$_{1-3}$alkyl is optionally substituted with one or more substituents independently selected from —OT¹ and —N(T²)(T³).

In yet another particularly preferred embodiment, X⁴ is either absent or selected from the group consisting of —NR⁴— and —N(R⁴)(CH₂)— and Y¹ is a 4- to 7-membered saturated or unsaturated aromatic carbocycle or heterocycle, with the proviso that the point of attachment on said heterocycle is carbon if X⁴ is —NR⁴—, wherein said 4- to 7-membered saturated or unsaturated aromatic carbocycle or heterocycle is optionally substituted with one or more substituents independently selected from F, Cl, Br, I, —C(=O)H, —OT¹, —N(T²)(T³), —C(=O)N(T²)(T³), —C(=O)OT¹, —ST¹ and —C$_{1-3}$alkyl, wherein said —C$_{1-3}$alkyl is optionally substituted with one or more substituents independently selected from —OT¹ and —N(T²)(T³).

In another particularly preferred embodiment, said 4- to 7-membered saturated or unsaturated aromatic carbocycle or heterocycle is selected from the group consisting of azetidine, oxetane, thietane, cyclopentyl, pyrrolidine, tetrahydrofuran, thiolane, pyrazolidine, cyclohexyl, piperidine, tetrahydropyran, thiane, piperazine, morpholine, thiomorpholine, pyridine, benzyl, azepane, oxepane and thiepane, preferably from the group consisting of azetidine, pyrrolidine, cyclohexyl, piperidine, piperazine, morpholine, tetrahydropyran, thiomorpholine, pyridine, benzyl and azepane. In a particularly preferred embodiment, said 4- to 7-membered saturated or unsaturated aromatic carbocycle or heterocycle is selected from the group consisting of piperidine, morpholine and piperazine, and is most preferably piperazine.

In another preferred embodiment, said 5- to 6-membered saturated heterocycle is selected from the group consisting of pyrrolidine, piperidine and piperazine.

In another preferred embodiment, X¹, X² and X³ are each independently selected from the group consisting of H, F, Cl, Br, I, —OT¹, —N(T²)(T³), —NHC(=O)T⁴, nitro, cyano, cyclopropyl and —C$_{1-3}$alkyl, with the proviso that at least two substituents selected from X¹, X² and X³ are not H, wherein said —C$_{1-3}$alkyl is methyl or ethyl, preferably methyl. It can be particularly preferred that X¹ is methyl.

In another preferred embodiment, X¹, X² and X³ are each independently selected from the group consisting of F, Cl, Br, I, —OT¹, —N(T²)(T³), —NHC(=O)T⁴, nitro, cyano, cyclopropyl and —C$_{1-3}$alkyl. It can further be preferred that said —C$_{1-3}$alkyl is methyl or ethyl, more preferably methyl.

In another preferred embodiment, X¹ is selected from the group consisting of H, F, Cl, Br, I, —OT¹, —N(T²)(T³), —NHC(=O)T⁴, nitro, cyano, cyclopropyl and —C$_{1-3}$alkyl, and X² and X³ are independently selected from the group consisting of F, Cl, Br, I and —C$_{1-3}$alkyl. It can also be preferred that X¹ is selected from the group consisting of F, Cl, Br, I, —OT¹, —N(T²)(T³), —NHC(=O)T⁴, nitro, cyano, cyclopropyl and —C$_{1-3}$alkyl, and X² and X³ are independently selected from the group consisting of F, Cl, Br, I and methyl. In another preferred embodiment, $X^1$ is methyl and $X^2$ and $X^3$ are independently selected from the group consisting of F, Cl, Br and I.

In another preferred embodiment, $X^1$, $X^2$ and $X^3$ are each independently selected from the group consisting of F, Cl, Br and I. In a particularly preferred embodiment, $X^1$, $X^2$ and $X^3$ are each Br.

In another preferred embodiment, at least two substituents selected from $X^1$, $X^2$ and $X^3$ are independently selected from the group consisting of F, Cl, Br and I.

In another preferred embodiment, $Z^1$ and $Z^2$ are each independently selected from the group consisting of H, —$C_{1-6}$alkyl, —$OT^1$ and —$N(T^2)(T^3)$. It can be preferred that $Z^1$ and $Z^2$ are each H.

In another preferred embodiment, $Z^3$ and $Z^4$ are each independently selected from the group consisting of H, —$C_{1-6}$alkyl, —$OT^1$ and —$N(T^2)(T^3)$. It can be preferred that $Z^3$ and $Z^4$ are each H.

In another preferred embodiment, $Z^5$ and $Z^6$ are each independently selected from the group consisting of H, —$C_{1-6}$alkyl, —$OT^1$ and —$N(T^2)(T^3)$. It can be preferred that $Z^5$ and $Z^6$ are each H.

In a preferred embodiment, $X^4$ is either absent or selected from the group consisting of —$NR^4$— and —$N(R^4)(CH_2)$—.

In another preferred embodiment, $X^4$ is —$NR^4$— and $Y^1$ is selected from H and —$C_{1-6}$alkyl, wherein said —$C_{1-6}$alkyl is optionally substituted with one or more substituents independently selected from —$OT^1$, —$ST^1$, —$N(T^2)(T^3)$ and a 5- to 6-membered saturated heterocycle. In this embodiment, it can be particularly preferred that said 5- to 6-membered saturated heterocycle is selected from the group consisting of pyrrolidine, piperazine and morpholine with point of attachment being nitrogen. Further, it can be preferred that said —$C_{1-6}$alkyl is a —$C_{1-3}$alkyl.

In another preferred embodiment, $X^4$ is absent and $Y^1$ is a 4- to 7-membered saturated heterocycle, wherein said 4- to 7-membered saturated heterocycle is optionally substituted with one or more substituents independently selected from F, Cl, Br, I, —C(═O)H, —$OT^1$, —$N(T^2)(T^3)$, —C(═O)N($T^2$)($T^3$), —C(═O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$. In this embodiment, it can be particularly preferred that said 4- to 7-membered saturated heterocycle is selected from the group consisting of azetidine, pyrrolidine, piperazine, peperidine, morpholine, thiomorpholine and azepane with point of attachment being nitrogen. Piperazine or piperidine may be particularly preferred in this respect. It can further be preferred that said 4- to 7-membered saturated heterocycle is a 5- to 6-membered saturated heterocycle, preferably a 6-membered saturated heterocycle, which is preferably selected from piperidine and piperazine.

In another preferred embodiment, $X^4$ is absent and $Y^1$ is a 6-membered saturated heterocycle, wherein said 6-membered saturated heterocycle is optionally substituted with one or more substituents independently selected from —$OT^1$, —$N(T^2)(T^3)$ and —$C_{1-3}$alkyl, wherein said —$C_{1-3}$alkyl is optionally substituted with —$N(T^2)(T^3)$. In this embodiment, it can be particularly preferred that said 6-membered saturated heterocycle is piperazine with point of attachment being nitrogen.

In another preferred embodiment, $X^4$ is absent and $Y^1$ is a 6-membered saturated carbocycle or heterocycle, wherein said 6-membered saturated carbocycle or heterocycle is optionally substituted with one or more substituents independently selected from F, Cl, Br, I, —C(═O)H, —$OT^1$, —$N(T^2)(T^3)$, —C(═O)N($T^2$)($T^3$), —C(═O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$. In this embodiment, it can be particularly preferred that said 6-membered saturated heterocycle is selected from the group consisting of piperazine and piperidine with point of attachment being carbon.

In another preferred embodiment, $X^4$ is —$NR^4$— and $Y^1$ is a 4- to 6-membered saturated or unsaturated aromatic carbocycle or heterocycle, wherein said 4- to 6-membered saturated or unsaturated aromatic carbocycle or heterocycle is optionally substituted with one or more substituents independently selected from F, Cl, Br, I, —C(═O)H, —$OT^1$, —$N(T^2)(T^3)$, —C(═O)N($T^2$)($T^3$), —C(═O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$. In this embodiment, it can be particularly preferred that said 4- to 6-membered saturated or unsaturated aromatic carbocycle or heterocycle is selected from the group consisting of azetidine, pyrrolidine, cyclohexyl, piperidine, tetrahydropyran, pyridine and benzyl with point of attachment being carbon.

In another preferred embodiment, $T^1$, $T^2$ and $T^3$ are each independently selected from H and —$C_{1-6}$alkyl optionally substituted with one or more substituents independently selected from —$N(T^5)(T^6)$, —$OT^7$, —$ST^7$, nitro and cyano.

In another preferred embodiment, $T^4$ is —$C_{1-6}$alkyl optionally substituted with one or more substituents independently selected from —$N(T^5)(T^6)$, —$OT^7$, —$ST^7$, nitro and cyano.

In another preferred embodiment, $T^5$, $T^6$ and $T^7$ are each independently selected from H and —$C_{1-6}$alkyl optionally substituted with one or more substituents independently selected from amino and hydroxyl.

In another preferred embodiment, $T^8$ is selected from —$C_{1-6}$alkyl optionally substituted with one or more substituents independently selected from amino and hydroxyl.

Embodiment (A) of the first aspect of the present invention relates to a compound of formula (I)

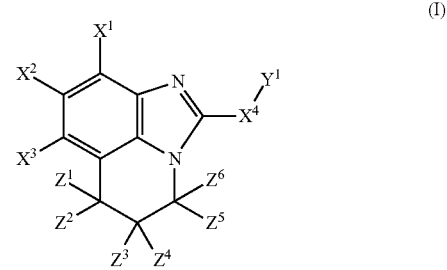

(I)

wherein
$X^1$, $X^2$ and $X^3$ are each independently selected from the group consisting of H, F, Cl, Br, I, —$OT^1$, —$N(T^2)(T^3)$, —NHC(═O)$T^4$, nitro, cyano, cyclopropyl and —$C_{1-3}$alkyl, with the proviso that at least two substituents selected from $X^1$, $X^2$ and $X^3$ are each independently selected from the group consisting of F, Cl, Br and I;
$Z^1$ and $Z^2$ are each independently selected from the group consisting of H, —$C_{1-6}$alkyl, —$OT^1$ and —$N(T^2)(T^3)$;
$Z^3$ and $Z^4$ are either taken together to form an oxo group at the carbon atom to which they are attached; or $Z^3$ and $Z^4$ are each independently selected from the group consisting of H, —$C_{1-6}$alkyl, —$OT^1$ and —$N(T^2)(T^3)$;

$Z^5$ and $Z^6$ are either taken together to form an oxo group at the carbon atom to which they are attached; or $Z^5$ and $Z^6$ are each independently selected from the group consisting of H, —$C_{1-6}$alkyl, —$OT^1$ and —$N(T^2)(T^3)$;

$X^4$ is either absent or selected from the group consisting of —$NR^4$—, —$N(R^4)(CH_2)$—, —$C(=O)NH$— and —$C(=O)$—;

$R^4$ is selected from H and —$C_{1-6}$alkyl;

$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —$NR^4$— or —$C(=O)NH$—, wherein said —$C_{1-6}$alkyl is optionally substituted with one or more substituents independently selected from —$OT^1$, —$ST^1$, —$N(T^2)(T^3)$ and a 5- to 6-membered saturated heterocycle, and wherein said 4- to 7-membered saturated or unsaturated aromatic carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$;

$T^1$, $T^2$ and $T^3$ are each independently selected from H and —$C_{1-6}$alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^7$, —$S(=O)_2OT^8$ and —$S(=O)_2N(T^5)(T^6)$;

$T^4$ is —$C_{1-6}$alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^5$, $T^6$ and $T^7$ are each independently selected from H and —$C_{1-6}$alkyl optionally substituted with one or more substituents independently selected from amino, hydroxyl, thiol, nitro and cyano; and $T^8$ is selected from —$C_{1-6}$alkyl optionally substituted with one or more substituents independently selected from amino, hydroxyl, thiol, nitro and cyano;

or a pharmaceutically acceptable salt thereof.

In a preferred embodiment of embodiment (A) of the first aspect, $X^1$ is selected from the group consisting of H, F, Cl, Br, I, —$OT^1$, —$N(T^2)(T^3)$, —$NHC(=O)T^4$, nitro, cyano, cyclopropyl and —$C_{1-3}$alkyl; and $X^2$ and $X^3$ are independently selected from the group consisting of F, Cl, Br and I. It can further be preferred in this respect that $X^1$ is selected from the group consisting of F, Cl, Br, I, nitro, cyano, cyclopropyl and —$C_{1-3}$alkyl; and $X^2$ and $X^3$ are independently selected from the group consisting of F, Cl, Br and I. It can also be preferred in this respect that $X^1$ is —$C_{1-3}$alkyl, preferably methyl; and $X^2$ and $X^3$ are independently selected from the group consisting of F, Cl, Br and I. In a particularly preferred embodiment relating to the present paragraph, $X^2$ and $X^3$ are Br.

In another preferred embodiment of embodiment (A) of the first aspect, $Y^1$ is a 4- to 7-membered saturated or unsaturated aromatic carbocycle or heterocycle, with the proviso that the point of attachment on said heterocycle is carbon if $X^4$ is —$NR^4$— or —$C(=O)NH$—, wherein said 4- to 7-membered saturated or unsaturated aromatic carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$.

In yet another preferred embodiment of embodiment (A) of the first aspect, $X^4$ is absent and $Y^1$ is a 4- to 7-membered saturated or unsaturated aromatic carbocycle or heterocycle, wherein said 4- to 7-membered saturated or unsaturated aromatic carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$. With respect to the above, said 4- to 7-membered saturated or unsaturated aromatic carbocycle or heterocycle may be selected from the group consisting of azetidine, oxetane, thietane, cyclopentyl, pyrrolidine, tetrahydrofuran, thiolane, pyrazolidine, cyclohexyl, piperidine, tetrahydropyran, thiane, piperazine, morpholine, thiomorpholine, pyridine, benzyl, azepane, oxepane and thiepane, preferably from the group consisting of azetidine, pyrrolidine, cyclohexyl, piperidine, piperazine, morpholine, tetrahydropyran, thiomorpholine, pyridine, benzyl and azepane; a selection from the group consisting of pyrrolidine, piperidine and piperazine may be particularly preferred. It can further be preferred in this respect that $X^4$ is absent and $Y^1$ is a 4- to 7-membered saturated heterocycle, wherein said 4- to 7-membered saturated heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$.

It can further be preferred in embodiment (A) of the first aspect that $X^4$ is absent and $Y^1$ is piperazine, wherein said piperazine is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$. Finally, it can be preferred in this regard that $X^4$ is absent and $Y^1$ is piperazine, wherein the point of attachment on said piperazine is nitrogen.

In still another preferred embodiment of embodiment (A) of the first aspect, $Z^1$, $Z^2$, $Z^3$, $Z^4$, $Z^5$ and $Z^6$ are each independently selected from the group consisting of H, —$C_{1-6}$ alkyl, —$OT^1$ and —$N(T^2)(T^3)$. It can be preferred in this respect that $Z^1$, $Z^2$, $Z^3$, $Z^4$, $Z^5$ and $Z^6$ are each independently selected from the group consisting of H and —$C_{1-6}$alkyl. It can be particularly preferred in this respect that $Z^1$, $Z^2$, $Z^3$, $Z^4$, $Z^5$ and $Z^6$ are each H.

In yet another preferred embodiment of embodiment (A) of the first aspect, $T^1$, $T^2$ and $T^3$ are each independently selected from H and —$C_{1-6}$alkyl optionally substituted with one or more substituents independently selected from —$N(T^5)(T^6)$, —$OT^7$, —$ST^7$, nitro and cyano. Further, $T^4$ may be —$C_{1-6}$alkyl optionally substituted with one or more substituents independently selected from —$N(T^5)(T^6)$, —$OT^7$, —$ST^7$, nitro and cyano. Also $T^5$, $T^6$ and $T^7$ may each be independently selected from H and —$C_{1-6}$alkyl optionally substituted with one or more substituents independently selected from amino and hydroxyl. Finally, $T^8$ may be selected from —$C_{1-6}$alkyl optionally substituted with one or more substituents independently selected from amino and hydroxyl.

A particularly preferred compound of the first aspect of the invention is 7,8-dibromo-9-methyl-2-(piperazin-1-yl)-5,6-dihydro-4H-imidazo[4,5,1-ij]quinoline, particularly the hydrochloride salt thereof.

In another preferred embodiment, the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate. The hydrochloride salt can be particularly preferred.

In a second aspect, the present invention is concerned with a pharmaceutical composition comprising the compound according to the first aspect as outlined above, including all preferred embodiments as mentioned above. Preferred embodiments of the second aspect are referred to when describing the present invention in more detail.

In a third aspect, the present invention is concerned with a pharmaceutical composition according to the present invention for use in the treatment of specific diseases, as will also be set out below in more detail.

Further, the present invention is concerned with methods and uses as set out hereinafter.

DETAILED DESCRIPTION OF THE INVENTION

Figure 1:
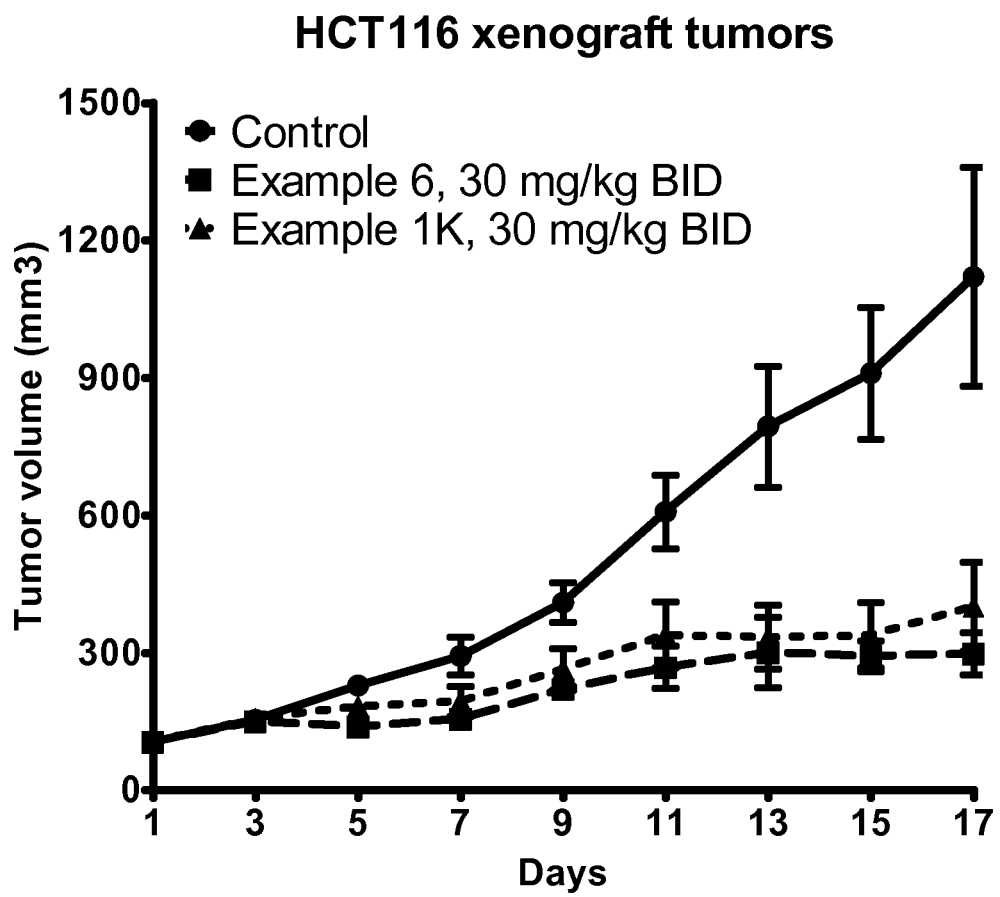
FIG. 1: Inhibition of HCT116 tumor growth by oral administration of the compounds "Example 6" and "Example 1K" in NOD/SCID mice.

The inventors of the present invention inter alia succeeded in identifying new compounds which efficiently inhibit CDK8. The compounds of the present invention may thus be particularly used in the treatment of cancer, autoimmune and inflammatory diseases.

Before some of the embodiments of the present invention are described in more detail, the following definitions are introduced.

1. DEFINITIONS

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "alkyl" refers to a hydrocarbon chain that may be a straight chain or branched chain, containing the indicated number of carbon atoms. For example, $C_{1-6}$ indicates that the group may have from 1 to 6 (inclusive) carbon atoms in it. If there is no indication of carbon atoms of the alkyl, the term "alkyl" refers to a $C_{1-15}$alkyl, preferably a $C_{1-10}$alkyl, and more preferably to a $C_{1-4}$alkyl.

In general, the number of carbon atoms present in a given group is designated "Cx-y" where x and y are the lower and upper limits, respectively. For example, a group designated as "$C_{1-5}$" contains from 1 to 5 carbon atoms. The carbon number as used in the definitions herein refers to carbon backbone and carbon branching, but does not include carbon atoms of the substituents. General examples of alkyl groups include methyl, ethyl, propyl, isopropyl, butyl, n-butyl, isobutyl, sec-butyl, tert-butyl, and pentyl. For example, the term "$C_{1-3}$alkyl" refers to a straight or branched chain saturated hydrocarbon containing 1-3 carbon atoms. Examples of a $C_{1-3}$alkyl group include, but are not limited to, methyl, ethyl, propyl and isopropyl. For example, the term "$C_{6-10}$alkyl" refers to a straight or branched chain saturated hydrocarbon containing 6-10 carbon atoms. Examples of a $C_{6-10}$alkyl group include, but are not limited to, hexyl, octyl and decyl.

The term "heterocycle" refers to a cyclic structure comprising carbon atoms and at least one heteroatom. The term "heteroatom" as used herein preferably refers to nitrogen, sulfur and oxygen atoms. A heterocycle may generally contain different heteroatoms. For the present invention, nitrogen as heteroatom may be preferred. Further, for the present invention, it can be preferred that a heterocycle comprises one or two heteroatoms. If reference to a specific heterocycle is made herein (such as e.g. to piperazine), this reference has to be understood as relating to the commonly used and defined structure of said heterocycle in the field of chemistry.

If e.g. reference to a "4- to 7-membered saturated or unsaturated aromatic carbocycle or heterocycle" is made herein, it needs to be understood that the term "aromatic" is used in combination with the term "unsaturated" only; thus, the above definition may also be regarded as short definition of a "4- to 7-membered saturated non-aromatic or a 4- to 7-membered unsaturated aromatic carbocycle or heterocycle". Of course, the term "aromatic" as used in the short definition is not to be read in combination with the term "saturated" since reference would otherwise be made to a non-existing "saturated aromatic carbocycle or heterocycle".

The term "halogen" includes fluoride, bromide, chloride or iodide. The term "amino" represents —NH$_2$, the term "hydroxyl" is —OH, the term "thiol" is —SH, the term "nitro" is —NO$_2$—, the term "cyano" is —CN and "oxo" is =O. "Carbon branching" or "branched alkyl" means that one or more alkyl groups such as methyl, ethyl or propyl, replace one or both hydrogens in a —CH$_2$— group of a linear alkyl chain.

If a substituent is not defined as the final substituent but rather as a bridging substituent (such as e.g. the $X^4$ definition of "—NR$^4$(CH$_2$)—"), the definition is preferably used in terms of the structure of a compound of the present invention as from left to right in the overall structure. This means e.g.

for "—NR$^4$(CH$_2$)—" that the nitrogen is attached to the benzimidazole-moiety, whereas the —CH$_2$— is attached to substituent Y$^1$.

If a point of attachment on a heterocycle is defined, this refers to an atom in the heterocycle, to which the remaining moiety of the compound is attached to. In most cases of the present invention, this may e.g. refer to the attachment of X$^4$ to a heterocycle or, alternatively, if X$^4$ is not present, to the attachment of the benzimidazole-moiety at position 2 to the heterocycle (direct bond).

The compounds disclosed herein may contain one or more asymmetric centers and may thus lead to enantiomers, diastereomers, and other stereoisomeric forms. The present invention is also meant to encompass all such possible forms as well as their racemic and resolved forms and mixtures thereof, unless specified otherwise. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers). The term "chiral center" refers to a carbon atom to which four different groups are attached. The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction. The term "racemic" refers to a mixture of equal parts of enantiomers and which is optically inactive. The term "resolution" refers to the separation or concentration or depletion of one of the two enantiomeric forms of a molecule.

"Pharmaceutically active agent" as used herein means that a compound is potent of modulating a response in a human or animal being in vivo. When reference is made to a compound as "the only pharmaceutically active agent", this is meant to describe that the activity of a corresponding pharmaceutical composition is due to said active agent only.

The term "pharmaceutically acceptable excipient" as used herein refers to compounds commonly comprised in pharmaceutical compositions, which are known to the skilled person. Such compounds or excipients are exemplary listed below. In view of the definition "pharmaceutically active agent" as given above, a pharmaceutically acceptable excipient can be defined as being pharmaceutically inactive.

In the following, the pharmaceutical compositions according to the present invention are described in more detail.

A pharmaceutical composition according to the present invention may be formulated for oral, buccal, nasal, rectal, topical, transdermal or parenteral application. Oral application may be preferred. Parenteral application can also be preferred and includes intravenous, intramuscular or subcutaneous administration. The compound according to formula (I) should be applied in pharmaceutically effective amounts, for example in the amounts as set out herein below.

A pharmaceutical composition of the present invention may also be designated as formulation or dosage form. A compound of formula (I) may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, salt solutions, alcohols, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethyl-cellulose, polyvinylpyrrolidone and the like. The pharmaceutical compositions can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compounds of formula (I) in water-soluble form. Additionally, suspensions of the compounds of formula (I) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a compound of formula (I). Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluant or solvent. Among the acceptable vehicles and solvents that can be used are water and isotonic sodium chloride solution. Sterile oils are also conventionally used as solvent or suspending medium.

Suppositories for rectal administration of a compound of formula (I) can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the compound according to formula (I) from said suppositories.

For administration by inhalation, the compounds according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the compound of formula (I) or a sustained release of the compound of formula (I).

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

As regards human patients, the compound of formula (I) may be administered to a patient in an amount of about 0.001 mg to about 1000 mg per day, preferably of about 0.01 mg to about 10 mg per day, more preferably of about 0.1 mg to about 5 mg per day.

A pharmaceutical composition according to the present invention may particularly be used in the treatment of cancer, autoimmune and inflammatory diseases. Brief definitions of the most relevant terms in this respect are introduced in the following. It is noted that the treatment of cancer includes the treatment of metastatic cancers and/or of metastastes and thus also refers to the inhibition of the process of metastasis during cancer treatment (particularly for colon cancer as shown in example 3.17. of the present application).

The term "cancer" refers to a group of diseases in which cells are aggressive (grow and divide without respect to normal limits), invasive (invade and destroy adjacent tissues), and sometimes metastatic (spread to other locations in the body). These three malignant properties of cancers differentiate them from benign tumors, which are self-limited in their growth and don't invade or metastasize (although some benign tumor types are capable of becoming malignant). A particular type of cancer is a cancer forming solid tumours. Such cancer forming solid tumours can be breast cancer, colorectal cancer, lung cancer, prostate carcinoma or oral squamous carcinoma. Other cancer forming solid tumours for which the compositions of the invention would be well suited can be selected from the group consisting of adrenal cortical carcinomas, angiomatoid fibrous histiocytomas (AFH), squamous cell bladder carcinomas, urothelial carcinomas, bone tumours, e.g. adamantinomas, aneurysmal bone cysts, chondroblastomas, chondromas, chondromyxoid fibromas, chondrosarcomas, fibrous dysplasias of the bone, giant cell tumours, osteochondromas or osteosarcomas, breast tumours, e.g. secretory ductal carcinomas, chordomas, clear cell hidradenomas of the skin (CCH), colorectal adenocarcinomas, carcinomas of the gallbladder and extrahepatic bile ducts, combined hepatocellular and cholangiocarcinomas, fibrogenesis imperfecta ossium, pleomorphic salivary gland adenomas head and neck squamous cell carcinomas, chromophobe renal cell carcinomas, clear cell renal cell carcinomas, nephroblastomas (Wilms tumor), papillary renal cell carcinomas, primary renal ASPSCR1-TFE3 t(X;17)(p11;q25) tumors, renal cell carcinomas, laryngeal squamous cell carcinomas, liver adenomas, hepatoblastomas, hepatocellular carcinomas, non-small cell lung carcinomas, small cell lung cancers, malignant melanoma of soft parts, medulloblastomas, meningiomas, neuroblastomas, astrocytic tumours, ependymomas, peripheral nerve sheath tumours, neuroendocrine tumours, e.g. phaeochromocytomas, neurofibromas, oral squamous cell carcinomas, ovarian tumours, e.g. epithelial ovarian tumours, germ cell tumours or sex cord-stromal tumours, pericytomas, pituitary adenomas, posterior uveal melanomas, rhabdoid tumours, skin melanomas, cutaneous benign fibrous histiocytomas, intravenous leiomyomatosis, aggressive angiomyxomas, liposarcomas, myxoid liposarcomas, low grade fibromyxoid sarcomas, soft tissue leiomyosarcomas, biphasic synovial sarcomas, soft tissue chondromas, alveolar soft part sarcomas, clear cell sarcomas, desmoplastic small round cell tumours, elastofibromas, Ewing's tumours, extraskeletal myxoid chondrosarcomas, inflammatory myofibroblastic tumours, lipoblastomas, lipoma, benign lipomatous tumours, liposarcomas, malignant lipomatous tumours, malignant myoepitheliomas, rhabdomyosarcomas, synovial sarcomas, squamous cell cancers, subungual exostosis, germ cell tumours in the testis, spermatocytic seminomas, anaplastic (undifferentiated) carcinomas, oncocytic tumours, papillary carcinomas, carcinomas of the cervix, endometrial carcinomas, leiomyoma as well as vulva and/or vagina tumours. In an embodiment of the invention, the cancer is a cancer of the gastrointestinal trackt (for example colon and rectum), of the lung or a melanoma.

The term "CDK8-related cancer" refers to the cancer where a CDK8 has become an essential gene. CDK8-dependent cancers can be easily identified by depleting the cells of CDK8 expression, and identifying the cancers that are at least partially repressed in the absence of it. Due to the structural and functional similarities between CDK8 and CDK19, the term CDK8-related cancers may also applied to the cancer where CDK19 plays similar role to CDK8.

The term "CDK8-related autoimmune and inflammatory disorders" refers to the conditions where the expression of pro-inflammatory cytokines is at least partially dependent on the activity of CDK8. These conditions could be easily identified by depleting the cells of CDK8 expression, and identifying the cells expressing lower levels of proinflammatory cytokines in the absence of it.

The term "autoimmune" refers to the process by which immune system components such as antibodies or lymphocytes attack or harm molecules, cells, or tissues of the organism producing them. The term "autoimmune disorders" refers to diseases where damage, such as tissue damage, or pathogenesis is, at least partially, a result of an autoimmune process arising from an inappropriate immune response of the body against substances and tissues normally present in the body. By way of example, the term "autoimmune disease" includes those diseases that are mediated at least partially by a Th1 response and refers to differentiation of T helper cells from precursors into distinct populations of Th1 effector cells, and includes secretion of cytokines from Th1 cells, such as IFN-gamma, IL-2, and TNF-beta or $CD8^{+}$cytotoxic T-lymphocytes. Autoimmune diseases include allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

The term "inflammatory disorders" refers to pathological conditions mediated by T and B cells function, such as rheumatoid arthritis, lupus, multiple sclerosis, and inflammatory bowel disease.

The phrase "effective amount" means an amount of compound that, when administered to a mammal in need of such treatment, is sufficient to treat or prevent a particular disease, condition.

In a preferred embodiment relating to the pharmaceutical compositions of the present invention, said pharmaceutical composition comprises said compound as the only pharmaceutically active agent.

Alternatively, said pharmaceutical composition comprises at least one further independent pharmaceutically active agent in addition to said compound. As outlined above, the pharmaceutical composition according to the present invention may particularly be used in the treatment of a cancer, an autoimmune or an inflammatory disease such that at least one further independent pharmaceutically active agents directed to the treatment of such a particular disease may be additionally present.

Thus, Compounds of the present invention may also be useful as adjuvants to cancer treatment, that is, they can be used in combination with one or more additional drugs, for example a chemotherapeutic that works by the same or by a different mechanism of action.

Further, Compounds of the present invention may also be used in combination with one or more additional drugs, for example an anti-inflammatory compound, an immunosuppressive compound or an immunodepleting agent that works by the same or a different mechanism of action.

2. ALTERNATIVE FORMULATIONS

The subject matter of the present invention may also be referred to as follows:

Method of administering to a subject in need thereof an effective amount of a compound according to formula (I) or a pharmaceutically acceptable salt thereof as defined above (including the preferred embodiments).

Method of treating a disease selected from the disease as disclosed herein by administering to a subject in need thereof an effective amount of a compound according to formula (I) or a pharmaceutically acceptable salt thereof as defined above (including the preferred embodiments).

Method for treating a CDK8-related disorder, said method comprising the step of administering to a patient in need thereof a therapeutic amount of a compound according to formula (I) or a pharmaceutically acceptable salt thereof as defined above (including the preferred embodiments).

Method for treating a CDK8-related cancer, said method comprising the step of administering to a patient in need thereof a therapeutic amount of a compound according to formula (I) or a pharmaceutically acceptable salt thereof as defined above (including the preferred embodiments).

Method for treating a CDK8-related autoimmune or inflammatory disorder, said method comprising the step of administering to a patient in need thereof a therapeutic amount of a compound according to formula (I) or a pharmaceutically acceptable salt thereof as defined above (including the preferred embodiments).

In the following, examples of embodiments of the present invention are outlined. However, said examples should not be construed as limiting the scope of the present invention.

3. EXAMPLES

3.1. Example 1

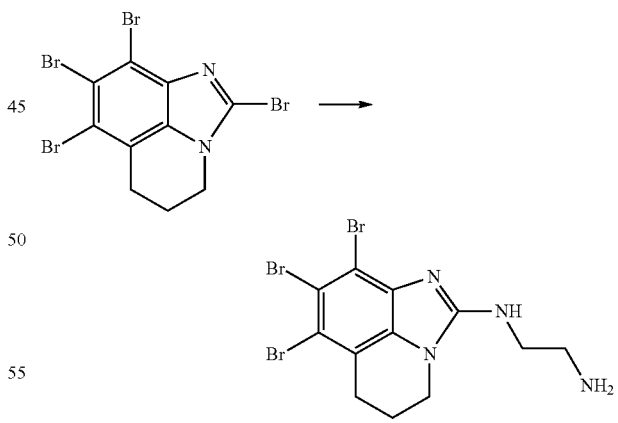

N-(7,8,9-tribromo-5,6-dihydro-4H-imidazo[4,5,1-ij] quinolin-2-yl)ethane-1,2-diamine hydrochloride Example 1A A mixture of 2,7,8,9-tetrabromo-5,6-dihydro-4H-imidazo [4,5,1-ij]quinoline (Method 1A) (0.475 g, 1 mmol) and N-Boc-ethylenediamine (0.32 g, 2 mmol) in ethanol (3 mL) was heated in sealed tube at 120° C. for 18 hrs. Reaction mixture was cooled down to the ambient temperature and solvent was removed under reduced pressure. The residue was dissolved in dichloromethane and washed with water. The organic layer was separated, dried over anhydrous sodium sulfate and concentrated under reduced pressure. The crude material was purified by column chromatography (silica gel, dichloromethane/methanol 20:1). Purified product was dissolved in methanol (1 mL) then 4M HCl in dioxane (3 mL) was added and reaction was stirred at room temperature overnight. Precipitated white product was collected by filtration, washed with diethyl ether and air dried to give 0.25 g of N-(7,8,9-tribromo-5,6-dihydro-4H-imidazo[4,5,1-ij]quinolin-2-yl)ethane-1,2-diamine as hydrochloride salt; yield 51%. LC-MS (m/z) 454.9 (M+1). $^1$H NMR (600 MHz, DMSO) δ 8.40 (s, 2H), 8.32 (s, 1H), 4.05 (t, 2H), 3.81-3.79 (m, 2H), 3.16-3.13 (m, 2H), 2.82 (t, 2H), 2.17-2.13 (m, 2H).

The following compounds were prepared by the procedure of Example 1A, using the appropriate starting materials:

| Ex. | Product | $^1$H NMR | m/z | RT [min] | Starting materials |
|---|---|---|---|---|---|
| 1B | (1R,2R)-N-(7,8,9-tribromo-5,6-dihydro-4H-imidazo[4,5,1-ij]quinolin-2-yl)cyclohexane-1,2-diamine hydrochloride 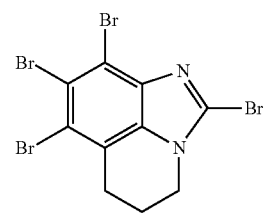 | $^1$H NMR (600 MHz, DMSO) δ 8.40 (s, 2H), 4.23-4.14 (m, 1H), 4.11 (s, 1H), 4.00-3.95 (m, 1H), 3.38-3.17 (m, 1H), 2.89-2.77 (m, 2H), 2.29-2.15 (m, 1H), 2.21-2.09 (m, 2H), 2.12-2.01 (m, 2H), 1.75 (t, J = 12.0 Hz, 2H), 1.62-1.43 (m, 2H), 1.45-1.32 (m, 1H), 1.35-1.21 (m, 1H) | 507.1 | 2.8 | 2,7,8,9-tetrabromo-5,6-dihydro-4H-imidazo[4,5,1-ij]quinoline<br>Method 1A and (1S,2R)-(2-amino-cyclohexyl)-carbamic acid tert-butyl ester (commercial) |
| 1C | N-(7,8,9-tribromo-5,6-dihydro-4H-imidazo[4,5,1-ij]quinolin-2-yl)propane-1,3-diamine hydrochloride 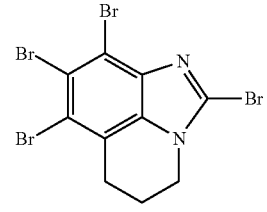 | $^1$H NMR (600 MHz, DMSO) δ 8.17 (bs, 2H), 4.02 (t, J = 5.4 Hz, 2H), 3.65-3.63 (m, 3H), 2.97-2.91 (m, 2H), 2.81 (t, 2H), 2.17-2.13 (m, 2H), 1.98-1.93 (m, 2H) | 467.0 | 2.4 | 2,7,8,9-tetrabromo-5,6-dihydro-4H-imidazo[4,5,1-ij]quinoline<br>Method 1A and tert-butyl (3-aminopropyl)carbamate (commercial) |
| 1D | 1-amino-3-[(7,8,9-tribromo-5,6-dihydro-4H-imidazo[4,5,1-ij]quinolin-2-yl)amino]propan-2-ol hydrochloride 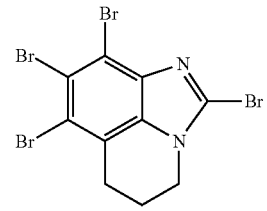 | $^1$H NMR (300 MHz, DMSO) δ 9.26 (s, 1H), 8.13 (s, 2H), 4.07-3.96 (m, 2H), 3.95-3.70 (m, 2H), 3.69-3.54 (m, 2H), 3.08-2.95 (m, J = 14.6, 5.8 Hz, 1H), 2.79 (t, J = 5.9 Hz, 2H), 2.27-2.01 (m, 2H) | 483.0 | 2.2 | 2,7,8,9-tetrabromo-5,6-dihydro-4H-imidazo[4,5,1--ij]quinoline<br>Method 1A and tert-butyl N-(3-amino-2-hydroxypropyl)carbate (commercial) |

| Ex. | Product | ¹H NMR | m/z | RT [min] | Starting materials |
|---|---|---|---|---|---|
| 1E | 7,8,9-tribromo-2-(2-methylpiperazin-1-yl)-5,6-dihydro-4H-imidazo[4,5,1-ij]quinoline hydrochloride | | 493.0 | 2.7 | 2,7,8,9-tetrabromo-5,6-dihydro-4H-imidazo[4,5,1-ij]quinoline<br><br>Method 1A and tert-butyl 3-methylpiperazine-1-carboxylate (commercial) |
| 1F | 7,8,9-tribromo-N-(pyrrolidin-2-ylmethyl)-5,6-dihydro-4H-imidazo[4,5,1-ij]quinolin-2-amine hydrochloride | ¹H NMR (300 MHz, DMSO) δ 9.72 (bs, 1H), 9.44 (bs, 1H), 8.32 (bs, 1H), 4.08-3.99 (m, 2H), 3.84 (s, 2H), 3.30-3.08 (m, 2H), 2.80 (t, J = 6.0 Hz, 2H), 2.20-2.02 (m, 3H), 2.02-1.78 (m, 2H), 1.79-1.66 (m, 1H). | 493.0 | 2.8 | 2,7,8,9-tetrabromo-5,6-dihydro-4H-imidazo[4,5,1-ij]quinoline<br><br>Method 1A and tert-butyl 2-(aminomethyl)pyrrolidine-1-carboxylate (commercial) |
| 1G | (3S)-1-(7,8,9-tribromo-5,6-dihydro-4H-imidazo[4,5,1-ij]quinolin-2-yl)pyrrolidin-3-amine hydrochloride | ¹H NMR (300 MHz, DMSO) δ 8.48 (s, 2H), 4.28 (t, J = 5.5 Hz, 2H), 4.03-3.87 (m, 5H), 2.80 (t, J = 5.5 Hz, 2H), 2.33-2.08 (m, 4H) | 479.0 | 2.5 | 2,7,8,9-tetrabromo-5,6-dihydro-4H-imidazo[4,5,1-ij]quinoline<br><br>Method 1A and (S)-tert-butyl pyrrolidin-3-ylcarbamate (commercial) |

-continued

| Ex. | Product | ¹H NMR | m/z | RT [min] | Starting materials |
|---|---|---|---|---|---|
| 1H | 1-[1-(7,8,9-tribromo-5,6-dihydro-4H-imidazo[4,5,1-ij]quinolin-2-yl)pyrrolidin-2-yl]methanamine hydrochloride | | 493.0 | 2.9 | 2,7,8,9-tetrabromo-5,6-dihydro-4H-imidazo[4,5,1-ij]quinoline<br><br>Method 1A and tert-butyl (pyrrolidin-2-yl)methylcarbamate (commercial) |
| 1I | 1-(7,8,9-tribromo-5,6-dihydro-4H-imidazo[4,5,1-ij]quinolin-2-yl)piperidin-3-amine hydrochloride | ¹H NMR (600 MHz, DMSO) δ 8.65-8.29 (m, 2H), 4.44-3.80 (m, 4H), 3.61-3.26 (m, 3H), 3.21 (bs, 1H), 2.96-2.72 (m, 2H), 2.18-1.97 (m, 2H), 1.95-1.83 (m, 1H), 1.78-1.54 (m, 2H) | 493.0 | 2.6 | 2,7,8,9-tetrabromo-5,6-dihydro-4H-imidazo[4,5,1-ij]quinoline<br><br>Method 1A and tert-butyl N-(3-piperidinyl)carbamate (commercial) |
| 1J | 7,8,9-tribromo-N-(piperidin-4-yl)-5,6-dihydro-4H-imidazo[4,5,1-ij]quinolin-2-amine hydrochloride | ¹H NMR (600 MHz, DMSO) δ 9.18 (s, 1H), 9.07 (s, 1H), 4.25 (bs, 1H), 4.05-4.03 (m, 2H), 3.44-3.30 (m, 2H), 3.02-2.91 (m, 2H), 2.81 (t, J = 6.1 Hz, 2H), 2.20-2.04 (m, 4H), 2.00-1.88 (m, 2H) | 493.0 | 2.4 | 2,7,8,9-tetrabromo-5,6-dihydro-4H-imidazo[4,5,1-ij] quinoline<br><br>Method 1A and tert-butyl 4-aminopiperidine-1-carboxylate (commercial) |

-continued

| Ex. | Product | ¹H NMR | m/z | RT [min] | Starting materials |
|---|---|---|---|---|---|
| 1K | 7,8-dibromo-9-methyl-2-(piperazin-1-yl)-5,6-dihydro-4H-imidazo[4,5,1-ij]quinoline hydrochloride | ¹H NMR (600 MHz, DMSO) δ 9.74 (bs, 1H), 4.15 (t, J = 5.7 Hz, 2H), 3.92-3.90 (m, 4H), 3.30-3.28 (m, 4H), 2.86 (t, J = 5.9 Hz, 2H), 2.65 (s, 3H), 2.12-2.06 (m, 2H) | 414.1 | 2.2 | 7,8-dibromo-2-chloro-9-methyl-5,6-dihydro-4H-imidazo[4,5,1-ij]quinoline<br><br>Method 2A and t-butyl piperazine-1-carboxylate (commercial) |
| 1L | 7,8,9-tribromo-N-(pyrrolidin-3-yl)-5,6-dihydro-4H-imidazo[4,5,1-ij]quinolin-2-amine hydrochloride | ¹H NMR (600 MHz, DMSO) δ 9.54-9.30 (m, 2H), 4.73-4.64 (m, 1H), 4.03 (t, J = 4.7 Hz, 2H), 3.52-3.25 (m, 4H), 2.81 (t, J = 6.1 Hz, 2H), 2.34-2.25 (m, 1H), 2.21-2.07 (m, 3H) | 479.0 | 2.6 | 2,7,8,9-tetrabromo-5,6-dihydro-4H-imidazo[4,5,1-ij]quinoline<br><br>Method 1A and tert-butyl 3-aminopyrrolidine-1-carboxylate (commercial) |
| 1M | 1-(7,8,9-tribromo-5,6-dihydro-4H-imidazo[4,5,1-ij]quinolin-2-yl)azepan-4-amine hydrochloride | | 507.1 | 2.4 | 2,7,8,9-tetrabromo-5,6-dihydro-4H-imidazo[4,5,1-ij]quinoline<br><br>Method 1A and tert-butyl 4-azepananylcarbamate (commercial) |

-continued

| Ex. | Product | ¹H NMR | m/z | RT [min] | Starting materials |
|-----|---------|--------|-----|----------|--------------------|
| 1N | 7,8-dibromo-2-(piperazin-1-yl)-5,6-dihydro-4H-imidazo[4,5,1-ij]quinoline hydrochloride | | 400.1 | 2.1 | 7,8-dibromo-2-chloro-5,6-dihydro-4H-imidazo[4,5,1-ij]quinoline<br><br>Method 14F and t-butyl piperazine-1-carboxylatte (commercial) |
| 1O | N-(7,8-dibromo-9-methyl-5,6-dihydro-4H-imidazo[4,5,1-ij]quinolin-2-yl)ethane-1,2-diamine hydrochloride | | 388.1 | 2.1 | 7,8-dibromo-2-chloro-9-methyl-5,6-dihydro-4H-imidazo[4,5,1-ij]quinoline<br><br>Method 2A and tert-butyl 2-aminoethylcarbamate (commercial) |
| 1P | N-(7,9-dibromo-8-methyl-5,6-dihydro-4H-imidazo[4,5,1-ij]quinolin-2-yl)ethane-1,2-diamine hydrochloride | ¹H NMR (300 MHz, DMSO) δ 8.22 (s, 2H), 4.05-3.97 (m, 2H), 3.80-3.73 (m, 2H), 3.11 (d, J = 5.2 Hz, 2H), 2.77 (t, J = 6.0 Hz, 2H), 2.56 (s, 3H), 2.18-2.09 (m, 2H) | 388.1 | 2.1 | 7,9-dibromo-2-chloro-8-methyl-5,6-dihydro-4H-imidazo[4,5,1-ij]quinoline<br><br>Method 9 and tert-butyl 2-aminoethylcarbamate (commercial) |

-continued

| Ex. | Product | ¹H NMR | m/z | RT [min] | Starting materials |
|---|---|---|---|---|---|
| 1S | 8,9-dibromo-7-methyl-2-(piperazin-1-yl)-5,6-dihydro-4H-imidazo[4,5,1-ij]quinoline hydrochloride | ¹H NMR (300 MHz, DMSO) δ 9.56 (s, 1H), 4.12-4.07 (m, 2H), 3.75-3.69 (m, 4H), 3.27-3.25 (m, 4H), 2.83 (t, J = 5.9 Hz, 2H), 2.41 (s, 3H), 2.09-2.01 (m, 2H) | 414.1 | 2.3 | 2,8,9-tribromo-7-methyl-5,6-dihydro-4H-imidazo[4,5,1-ij]quinoline<br><br>Method 1B and t-butyl piperazine-1-carboxylate (commercial) |
| 1T | N-(8,9-dibromo-7-methyl-5,6-dihydro-4H-imidazo[4,5,1-ij]quinolin-2-yl)ethane-1,2-diamine hydrochloride | | 388.1 | 2.0 | 2,8,9-tribromo-7-methyl-5,6-dihydro-4H-imidazo[4,5,1-ij]quinoline<br><br>Method 1B and tert-butyl 2-aminoethylcarbamate (commercial) |
| 1U | N-(7,8-dibromo-9-nitro-5,6-dihydro-4H-imidazo[4,5,1-ij]quinolin-2-yl)ethane-1,2-diamine hydrochloride | ¹H NMR (300 MHz, DMSO) δ 8.25 (t, 1H), 8.14 (bs, 2H), 3.98 (t, J = 5.7 Hz, 2H), 3.67-3.58 (m, 2H), 3.05 (t, J = 8.6 Hz, 2H), 2.84 (t, J = 6.0 Hz, 2H), 2.19-2.05 (m, 2H) | 419.1 | 2.5 | 7,8-dibromo-2-chloro-9-nitro-5,6-dihydro-4H-imidazo[4,5,1-ij]quinoline<br><br>Method 4 and tert-butyl 2-aminoethylcarbamate (commercial) |

-continued

| Ex. | Product | ¹H NMR | m/z | RT [min] | Starting materials |
|---|---|---|---|---|---|
| 1W | N-(7,8-dibromo-9-iodo-5,6-dihydro-4H-imidazo[4,5,1-ij]quinolin-2-yl)ethane-1,2-diamine hydrochloride | | 500.0 | 3.6 | 7,8-dibromo-2-chloro-9-iodo-5,6-dihydro-4H-imidazo[4,5,1-ij]quinoline<br><br>Method 6 and tert-butyl 2-aminoethylcarbamate (commercial) |
| 1X | 7,8-dibromo-9-nitro-2-(piperazin-1-yl)-5,6-dihydro-4H-imidazo[4,5,1-ij]quinoline hydrochloride | ¹H NMR (300 MHz, DMSO) δ 9.52 (s, 1H), 4.12 (t, J = 5.6 Hz, 2H), 3.72-3.64 (m, 4H), 3.22-3.20 (m, 4H), 2.88 (t, J = 5.8 Hz, 2H), 2.15-2.07 (m, 2H) | 445.1 | 2.5 | 7,8-dibromo-2-chloro-9-nitro-5,6-dihydro-4H-imidazo[4,5,1-ij]quinoline<br><br>Method 4 and t-butyl piperazine-1-carboxylate commercial |
| 1Y | 7,8-dibromo-9-iodo-2-(piperazin-1-yl)-5,6-dihydro-4H-imidazo[4,5,1-ij]quinoline hydrochloride | | 526.0 | 2.7 | 7,8-dibromo-2-chloro-9-iodo-5,6-dihydro-4H-imidazo[4,5,1-ij]quinoline<br><br>Method 6 and t-butyl piperazine-1-carboxylate (commercial) |

| Ex. | Product | ¹H NMR | m/z | RT [min] | Starting materials |
|---|---|---|---|---|---|
| 1Z | 7,8-dibromo-2-(piperazin-1-yl)-5,6-dihydro-4H-imidazo[4,5,1-ij]quinolin-9-amine hydrochloride | ¹H NMR (300 MHz, DMSO) δ 9.35 (s, 2H), 4.12-4.06 (m, 2H), 3.81-3.79 (m, 4H), 3.32-3.30 (m, 4H), 2.78-2.71 (m, 2H), 2.08-2.01 (m, 2H) | 415.1 | 2.4 | 7,8-dibromo-2-chloro-5,6-dihydro-4H-imidazo[4,5,1-ij]quinolin-9-amine; Method 5 and t-butyl piperazine-1-carboxylate (commercial) |
| 1AA | N2-(2-aminoethyl)-7,8-dibromo-5,6-dihydro-4H-imidazo[4,5,1-ij]quinoline-2,9-diamine hydrochloride | | 389.1 | 2.0 | 7,8-dibromo-2-chloro-5,6-dihydro-4H-imidazo[4,5,1-ij]quinolin-9-amine; Method 5 and tert-butyl 2-aminoethylcarbamate (commercial) |
| 1AB | N-(7,8-dibromo-5,6-dihydro-4H-imidazo[4,5,1-ij]quinolin-2-yl)ethane-1,2-diamine hydrochloride | ¹H NMR (300 MHz, DMSO) δ 9.62 (bs, 1H), 8.28 (bs, 2H), 7.60 (s, 1H), 4.05 (t, J = 5.6 Hz, 2H), 3.75 (dd, J = 11.0, 5.5 Hz, 2H), 3.14 (d, J = 4.8 Hz, 2H), 2.85 (t, J = 5.9 Hz, 2H), 2.20-2.10 (m, 2H) | 374.1 | 2.0 | 7,8-dibromo-2-chloro-5,6-dihydro-4H-imidazo[4,5,1-ij]quinoline; Method 14F and tert-butyl 2-aminoethylcarbamate (commercial) |

-continued

| Ex. | Product | ¹H NMR | m/z | RT [min] | Starting materials |
|---|---|---|---|---|---|
| 1AC | N-(7,8-dibromo-5,6-dihydro-4H-imidazo[4,5,1-ij]quinolin-2-yl)propane-1,3-diamine hydrochloride | ¹H NMR (300 MHz, DMSO) δ 9.61 (bs, 1H), 8.08 (bs, 2H), 7.58 (s, 1H), 4.01 (t, J = 5.6 Hz, 2H), 3.56 (dd, J = 12.4 6.3 Hz, 2H), 2.94 (dd, J = 11.8, 5.5 Hz, 2H), 2.83 (t, J = 5.9 Hz, 2H), 2.20-2.09 (m, 2H), 1.99-1.88 (m, 2H) | 388.1 | 2.1 | 7,8-dibromo-2-chloro-5,6-dihydro-4H-imidazo[4,5,1-ij]quinoline<br><br>Method 3 and tert-butyl (3-aminopropyl)carbamate (commercial) |
| 1AD | 1-[1-(7,8,9-tribromo-5,6-dihydro-4H-imidazo[4,5,1-ij]quinolin-2-yl)piperidin-4-yl]methanamine hydrochloride | ¹H NMR (300 MHz, DMSO) δ 8.09 (bs, 2H), 4.10-4.05 (m, 2H), 3.94-3.92 (m, 3H), 3.08 (t, J = 12.0 Hz, 2H), 2.82 (t, J = 5.9 Hz, 2H), 2.75 (dd, J = 11.7, 5.9 Hz, 2H), 2.07 (dd, J = 5.1, 2.4 Hz, 2H), 1.85 (d, J = 10.2 Hz, 2H), 1.45-1.28 (m, 2H) | 507.1 | 2.4 | 2,7,8,9-tetrabromo-5,6-dihydro-4H-imidazo[4,5,1-ij]quinoline<br><br>Method 1A and tert-butyl (piperidin-4-yl)methylcarbamate (commercial) |
| 1AE | (3S)-1-(7,8,9-tribromo-5,6-dihydro-4H-imidazo[4,5,1-ij]quinolin-2-yl)pyrrolidin-3-amine hydrochloride | ¹H NMR (300 MHz, DMSO) δ 8.61 (bs, 2H), 4.31 (t, J = 5.7 Hz, 2H), 4.13-4.04 (m, 2H), 3.97-3.90 (m, 3H), 2.80 (t, J = 6.0 Hz, 2H), 2.38-2.21 (m, 2H), 2.17-2.07 (m, 2H) | 479.0 | 2.5 | 2,7,8,9-tetrabromo-5,6-dihydro-4H-imidazo[4,5,1-ij]quinoline<br><br>Method 1A and tert-butyl (S)-pyrrolidin-3-ylcarbamate (commercial) |

-continued

| Ex. | Product | ¹H NMR | m/z | RT [min] | Starting materials |
|---|---|---|---|---|---|
| 1AF | 1-[4-(7,8,9-tribromo-5,6-dihydro-4H-imidazo[4,5,1-ij]quinolin-2-yl)morpholin-2-yl]methanamine hydrochloride | ¹H NMR (300 MHz, DMSO) δ 8.16 (bs, 2H), 4.09 (t, J = 6.2 Hz, 2H), 4.04-3.95 (m, 1H), 4.04-3.82 (m, 3H), 3.95-3.82 (m, 1H), 3.83-3.75 (m, 1H), 3.73 (s, 1H), 3.71-3.67 (m, 1H), 3.20-3.03 (m, 2H), 3.02-2.92 (m, 1H), 2.84 (t, J = 5.7 Hz, 2H) | 509.0 | 2.7 | 2,7,8,9-tetrabromo-5,6-dihydro-4H-imidazo[4,5,1-ij]quinoline. Method 1A and tert-butyl (morpholin-2-ylmethyl)carbamate (commercial) |
| 1AG | 1-(7,8,9-tribromo-5,6-dihydro-4H-imidazo[4,5,1-ij]quinolin-2-yl)piperidin-4-amine hydrochloride | ¹H NMR (300 MHz, DMSO) δ 8.20 (s, 2H), 4.05 (t, J = 5.6 Hz, 2H), 3.93-3.91 (m, 2H), 3.25-3.21 (m, 1H), 3.13 (t, J = 11.9 Hz, 2H), 2.83 (t, J = 5.9 Hz, 2H), 2.13-1.94 (m, 4H), 1.79-1.63 (m, 2H) | 493.0 | 2.7 | 2,7,8,9-tetrabromo-5,6-dihydro-4H-imidazo[4,5,1-ij]quinoline. Method 1A and tert-butyl N-piperidin-4-ylcarbamate (commercial) |
| 1AH | 7,8,9-tribromo-N-[3-(piperazin-1-yl)propyl]-5,6-dihydro-4H-imidazo[4,5,1-ij]quinolin-2-amine hydrochloride | ¹H NMR (300 MHz, DMSO) δ 9.83-9.81 (m, 2H), 4.04-3.97 (m, 4H), 3.65-3.60 (m, 4H), 3.32-3.25 (m, 4H), 2.80 (t, J = 5.9 Hz, 2H), 2.16-2.05 (m, 6H) | 536.1 | 2.1 | 2,7,8,9-tetrabromo-5,6-dihydro-4H-imidazo[4,5,1-ij]quinoline. Method 1A and tert-butyl 4-(3-aminopropyl)piperazine-1-carboxylate (commercial) |

| Ex. | Product | ¹H NMR | m/z | RT [min] | Starting materials |
|---|---|---|---|---|---|
| 1AI | 1-[4-(7,8-dibromo-9-methyl-5,6-dihydro-4H-imidazo[4,5,1-ij]quinolin-2-yl)morpholin-2-yl]methanamine hydrochloride | ¹H NMR (600 MHz, DMSO) δ 8.21 (bs, 2H), 4.21-4.13 (m, 2H), 4.05-4.00 (m, 1H), 3.99-3.93 (m, 1H), 3.81-3.71 (m, 2H), 3.20-3.08 (m, 2H), 2.95-2.86 (m, 4H), 2.66 (s, 3H), 2.11 (s, 2H) | 444.2 | 2.4 | 7,8-dibromo-2-chloro-9-methyl-5,6-dihydro-4H-imidazo[4,5,1-ij]quinoline<br><br>Method 2A and tert-butyl (morpholin-2-ylmethyl)carbamate (commercial) |
| 1AJ | 7,8,9-tribromo-N-[2-(piperazin-1-yl)ethyl]-5,6-dihydro-4H-imidazo[4,5,1-ij]quinolin-2-amine hydrochloride | | 522.1 | 3.0 | 2,7,8,9-tetrabromo-5,6-dihydro-4H-imidazo[4,5,1-ij]quinoline<br><br>Method 1A and tert-butyl 4-(2-aminoethyl)piperazine-1-carboxylate (commercial) |
| 1AK | (3R)-1-(7,8-dibromo-9-methyl-5,6-dihydro-4H-imidazo[4,5,1-ij]quinolin-2-yl)pyrrolidin-3-amine hydrochloride | ¹H NMR (600 MHz, DMSO) δ 8.63 (bs, 2H), 4.43-4.33 (m, 2H), 4.23-4.16 (m, 1H), 4.15-4.08 (m, 1H), 4.05-3.98 (m, 3H), 2.86 (t, J = 6.1 Hz, 2H), 2.66-2.64 (m, 3H), 2.40-2.32 (m, 1H), 2.30-2.23 (m, 1H), 2.22-2.10 (m, 2H) | 414.1 | 2.1 | 7,8-dibromo-2-chloro-9-methyl-5,6-dihydro-4H-imidazo[4,5,1-ij]quinoline<br><br>Method 2A and tert-butyl (R)-pyrrolidin-3-ylcarbamate (commercial) |

-continued

| Ex. | Product | ¹H NMR | m/z | RT [min] | Starting materials |
|---|---|---|---|---|---|
| 1AL | 7,8-dibromo-9-methyl-N-[(3S)-pyrrolidin-3-yl]-5,6-dihydro-4H-imidazo[4,5,1-ij]quinolin-2-amine hydrochloride | ¹H NMR (600 MHz, DMSO) δ 9.53 (bs, 1H), 9.51 (bs, 1H), 4.96 (s, 1H), 4.11 (t, J = 4.8 Hz, 2H), 3.58-3.48 (m, 2H), 3.50-3.47 (m, 1H), 2.84 (t, J = 6.0 Hz, 2H), 2.68 (s, 3H), 2.42-2.34 (m, 1H), 2.20-2.10 (m, 4H) | 414.1 | 2.0 | 7,8-dibromo-2-chloro-9-methyl-5,6-dihydro-4H-imidazo[4,5,1-ij]quinoline; Method 2A and (S)-tert-butyl 3-aminopyrrolidine-1-carboxylate (commercial) |
| 1AM | 7,8-dibromo-9-methyl-N-[(3R)-pyrrolidin-3-yl]-5,6-dihydro-4H-imidazo[4,5,1-ij]quinolin-2-amine hydrochloride | ¹H NMR (600 MHz, DMSO) δ 9.58 (bs, 2H), 4.99 (bs, 1H), 4.12 (t, J = 4.8 Hz, 2H), 3.58-3.50 (m, 2H), 3.50-3.47 (m, 1H), 2.84 (t, J = 6.0 Hz, 2H), 2.66-2.64 (m, 3H), 2.38 (td, J = 14.8, 8.0 Hz, 1H), 2.21-2.10 (m, 4H) | 414.1 | 1.9 | 7,8-dibromo-2-chloro-9-methyl-5,6-dihydro-4H-imidazo[4,5,1-ij]quinoline; Method 2A and (R)-tert-butyl 3-aminopyrrolidine-1-carboxylate (commercial) |
| 1AN | 7,9-dibromo-8-methoxy-2-(piperazin-1-yl)-5,6-dihydro-4H-imidazo[4,5,1-ij]quinoline hydrochloride | ¹H NMR (600 MHz, DMSO) δ 9.37 (bs, 1H), 4.10-4.07 (m, 2H), 3.78-7.75 (m, 3H), 3.67-3.65 (s, 4H), 3.28-3.25 (s, 4H), 2.81 (t, J = 5.7 Hz, 2H), 2.13-2.07 (m, 2H) | 430.1 | 2.2 | 2,7,9-tribromo-8-methoxy-5,6-dihydro-4H-imidazo[4,5,1-ij]quinoline; Method 1C and t-butyl piperazine-1-carboxylate (commercial) |

-continued

| Ex. | Product | ¹H NMR | m/z | RT [min] | Starting materials |
|---|---|---|---|---|---|
| 1AO | 7,8,9-tribromo-N-[(3S)-pyrrolidin-3-yl]-5,6-dihydro-4H-imidazo[4,5,1-ij]quinolin-2-amine hydrochloride 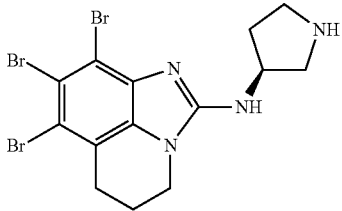 | | 479.0 | 2.4 | 2,7,8,9-tetrabromo-5,6-dihydro-4H-imidazo[4,5,1-ij]quinoline 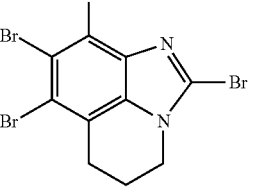  Method 1A and (S)-tert-butyl 3-aminopyrrolidine-1-carboxylate (commercial) |
| 1AP | 1-(7,8-dibromo-9-methyl-5,6-dihydro-4H-imidazo[4,5,1-ij]quinolin-2-yl)piperidin-4-amine hydrochloride 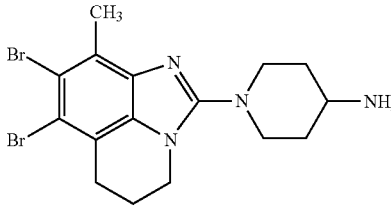 | ¹H NMR (600 MHz, DMSO) δ 8.45 (bs, 2H), 4.21-4.10 (m, 4H), 3.42-3.36 (m, 3H), 2.89-2.84 (m, 2H), 2.69-2.67 (m, 3H), 2.15-2.06 (m, 4H), 1.86-1.75 (m, 2H) | 428.2 | 2.1 | 7,8-dibromo-2-chloro-9-methyl-5,6-dihydro-4H-imidazo[4,5,1-ij]quinoline 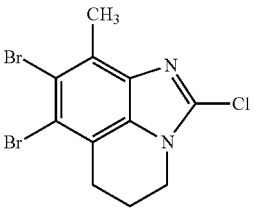  Method 2A and tert-butyl N-piperidin-4-ylcarbamate (commercial) |
| 1AR | 1-[1-(7,8-dibromo-9-methyl-5,6-dihydro-4H-imidazo[4,5,1-ij]quinolin-2-yl)piperidin-4-yl]methanamine hydrochloride 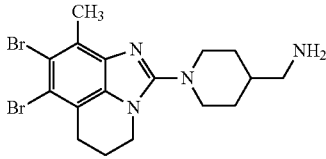 | | 442.2 | 2.5 | 7,8-dibromo-2-chloro-9-methyl-5,6-dihydro-4H-imidazo[4,5,1-ij]quinoline 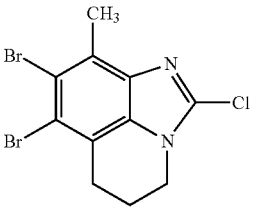  Method 2A and tert-butyl (piperidin-4-yl)methylcarbamate (commercial) |

-continued

| Ex. | Product | ¹H NMR | m/z | RT [min] | Starting materials |
|---|---|---|---|---|---|
| 1AS | trans-N-(7,8-dibromo-9-methyl-5,6-dihydro-4H-imidazo[4,5,1-ij]quinolin-2-yl)cyclohexane-1,4-diamine hydrochloride | | 442.2 | 2.4 | 7,8-dibromo-2-chloro-9-methyl-5,6-dihydro-4H-imidazo[4,5,1-ij]quinoline<br><br>Method 2A and N-boc-trans-1,4-cyclohexanediamine (commercial) |
| 1AT | (3S)-1-(7,8-dibromo-9-methyl-5,6-dihydro-4H-imidazo[4,5,1-ij]quinolin-2-yl)pyrrolidin-3-amine hydrochloride | ¹H NMR (600 MHz, DMSO) δ 8.65 (bs, 2H), 4.43-4.33 (m, 2H), 4.23-4.16 (m, 1H), 4.15-4.08 (m, 1H), 4.07-3.98 (m, 3H), 2.86 (t, J = 6.1 Hz, 2H), 2.67 (s, 3H), 2.35 (dt, J = 14.3, 8.9 Hz, 1H), 2.29-2.23 (m, 1H), 2.22-2.09 (m, 2H) | 414.1 | 2.0 | 7,8-dibromo-2-chloro-9-methyl-5,6-dihydro-4H-imidazo[4,5,1-ij]quinoline<br><br>Method 2A and tert-butyl (S)-pyrrolidin-3-ylcarbamate (commercial) |
| 1AU | 7,8,9-tribromo-4-methyl-2-(piperazin-1-yl)-5,6-dihydro-4H-imidazo[4,5,1-ij]quinoline hydrochloride | | 493.0 | 5.7 | 7,8,9-tribromo-2-chloro-4-methyl-5,6-dihydro-4H-imidazo[4,5,1-ij]quinoline<br><br>Method 2B and t-butyl piperazine-1-carboxylate (commercial) |

-continued

| Ex. | Product | ¹H NMR | m/z | RT [min] | Starting materials |
|---|---|---|---|---|---|
| 1AW | 7,8,9-tribromo-N-[(3S)-piperidin-3-yl]-5,6-dihydro-4H-imidazo[4,5,1-ij]quinolin-2-amine | | 493.0 | 2.7 | 2,7,8,9-tetrabromo-5,6-dihydro-4H-imidazo[4,5,1-ij]quinoline<br><br>Method 1A and (S)-N-boc-3-aminopiperidine (commercial) |
| 1AX | 7,9-dibromo-8-methyl-2-(piperazin-1-yl)-5,6-dihydro-4H-imidazo[4,5,1-ij]quinoline hydrochloride | ¹H NMR (300 MHz, DMSO) δ 9.61 (bs, 1H), 4.13-4.08 (m, 2H), 3.78-3.70 (m, 4H), 3.29-3.21 (m, 4H), 2.81 (t, J = 5.9 Hz, 2H), 2.57 (s, 3H), 2.14-2.04 (m, 2H) | 414.1 | 4.6 | Method 9 and t-butyl piperazine-1-carboxylate (commercial) |
| 1AY | 7,8-dibromo-9-methyl-N-[(3R)-piperidin-3-yl]-5,6-dihydro-4H-imidazo[4,5,1-ij]quinolin-2-amine hydrochloride | | 428.2 | 11.9 | 7,8-dibromo-2-chloro-9-methyl-5,6-dihydro-4H-imidazo[4,5,1-ij]quinoline<br><br>Method 2A and (R)-tert-butyl 3-aminopiperidine-1-carboxylate (commercial) |

-continued

| Ex. | Product | ¹H NMR | m/z | RT [min] | Starting materials |
|---|---|---|---|---|---|
| 1AZ | 7,8-dibromo-2-(1,4-diazepan-1-yl)-9-methyl-5,6-dihydro-4H-imidazo[4,5,1-ij]quinoline hydrochloride | ¹H NMR (300 MHz, DMSO) δ 9.40 (bs, 1H), 4.29-4.19 (m, 2H), 4.15-4.03 (m, 2H), 3.96-3.82 (m, 2H), 3.35-3.20 (m, 4H), 2.90-2.79 (m, 2H), 2.64 (s, 3H), 2.26-2.02 (m, 4H) | 428.2 | 2.1 | 7,8-dibromo-2-chloro-9-methyl-5,6-dihydro-4H-imidazo[4,5,1-ij]quinoline<br><br>Method 2A and tert-butyl 1,4-diazepane-1-carboxylate (commercial) |
| 1BA | 7,8-dibromo-9-cyclopropyl-2-(piperazin-1-yl)-5,6-dihydro-4H-imidazo[4,5,1-ij]quinoline hydrochloride | | 440.2 | 4.6 | tert-butyl 4-(7,8-dibromo-9-iodo-5,6-dihydro-4H-imidazo[4,5,1-ij]quinolin-2-yl)piperazine-1-carboxylate<br><br>Method 7B |
| 1BB | N-(azetidin-3-yl)-7,8-dibromo-9-methyl-5,6-dihydro-4H-imidazo[4,5,1-ij]quinolin-2-amine hydrochloride | | 400.1 | 2.3 | 7,8-dibromo-2-chloro-9-methyl-5,6-dihydro-4H-imidazo[4,5,1-ij]quinoline<br><br>Method 2A and tert-butyl 3-aminoazetadine-1-carboxylate (commercial) |

-continued

| Ex. | Product | ¹H NMR | m/z | RT [min] | Starting materials |
|---|---|---|---|---|---|
| 1BC | 7,8-dibromo-9-methyl-N-(morpholin-2-ylmethyl)-5,6-dihydro-4H-imidazo[4,5,1-ij]quinolin-2-amine hydrochloride | | 444.2 | 2.1 | 7,8-dibromo-2-chloro-9-methyl-5,6-dihydro-4H-imidazo[4,5,1-ij]quinoline<br><br>Method 2A and tert-butyl 2-(aminomethyl)morpholine-4-carboxylate |
| 1BD | 1-(7,8-dibromo-9-methyl-5,6-dihydro-4H-imidazo[4,5,1-ij]quinolin-2-yl)azetidin-3-amine hydrochloride | | 400.1 | 9.6 | 7,8-dibromo-2-chloro-9-methyl-5,6-dihydro-4H-imidazo[4,5,1-ij]quinoline<br><br>Method 2A and tert-butyl azetidin-3-ylcarbamate (commercial) |
| 1BE | (3S)-1-(7,8-dibromo-9-methyl-5,6-dihydro-4H-imidazo[4,5,1-ij]quinolin-2-yl)pyrrolidin-3-amine hydrochloride | ¹H NMR (300 MHz, DMSO) δ 8.41 (bs, 2H), 4.30 (t, J = 5.5 Hz, 2H), 4.06-3.86 (m, 5H), 2.78 (t, J = 6.0 Hz, 2H), 2.57 (s, 3H), 2.37-2.23 (m, 2H), 2.13 (dd, J = 12.0, 5.9 Hz, 2H) | 414.1 | 1.9 | 7,8-dibromo-2-chloro-9-methyl-5,6-dihydro-4H-imidazo[4,5,1-ij]quinoline<br><br>Method 2A and tert-butyl (S)-pyrrolidin-3-ylcarbamate (commercial) |

| Ex. | Product | ¹H NMR | m/z | RT [min] | Starting materials |
|---|---|---|---|---|---|
| 1BF | (3R)-1-(7,8-dibromo-9-methyl-5,6-dihydro-4H-imidazo[4,5,1-ij]quinolin-2-yl)piperidin-3-amine hydrochloride 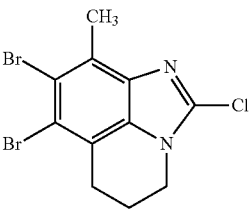 | | 428.2 | 2.6 | 7,8-dibromo-2-chloro-9-methyl-5,6-dihydro-4H-imidazo[4,5,1-ij]quinoline- 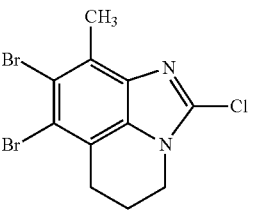<br>Method 2A and (R)-tert-butyl piperidin-3-ylcarbamate (commercial) |
| 1BG | (3S)-1-(7,8-dibromo-9-methyl-5,6-dihydro-4H-imidazo[4,5,1-ij]quinolin-2-yl)piperidin-3-amine hydrochloride | ¹H NMR (300 MHz, DMSO) δ 8.55 (bs, 2H), 4.31-4.24 (m, 1H), 4.18-4.03 (m, 2H), 3.73-3.65 (m, 2H), 3.50-3.47 (m, 2H), 2.88-2.86 (m, 2H), 2.65 (s, 3H), 2.14-1.89 (m, 4H), 1.79-1.66 (m, 2H). | 428.2 | 2.5 | 7,8-dibromo-2-chloro-9-methyl-5,6-dihydro-4H-imidazo[4,5,1-ij]quinoline<br>Method 2A and (S)-tert-butyl piperidin-3-ylcarbamate (commercial) |

3.2. Example 2

7,8,9-tribromo-N-[2-(morpholin-4-yl)ethyl]-5,6-dihydro-4H-imidazo[4,5,1-ij]quinolin-2-amine hydrochloride

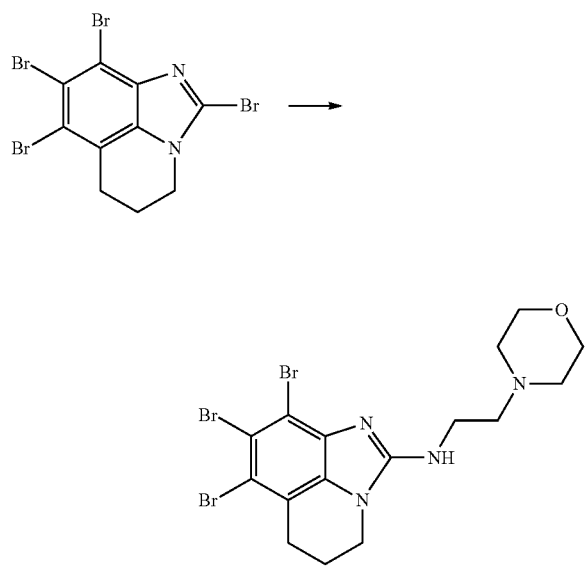

Example 2A

A 2,7,8,9-tetrabromo-5,6-dihydro-4H-imidazo[4,5,1-ij] quinoline (Method 1A) (0.14 g, 0.3 mmol), N-(2-aminoethyl)morpholine (0.18 g, 0.9 mmol) in ethanol (2 mL) were heated at 170° C. under microwave irradiation until the reaction is complete. The reaction mixture was allowed to cool to ambient temperature, then solvent was evaporated under reduced pressure. Crude product was purified by column chromatography (silica gel, dichloromethane/methanol 99:1). The product was dissolved in methanol (1 mL) then 4M HCl in dioxane (1 mL) was added dropwise. The reaction was stirred at room temperature overnight. The precipitated product was collected by filtration to gave 0.13 g of 7,8,9-tribromo-N-[2-(morpholin-4-yl)ethyl]-5,6-dihydro-4H-imidazo[4,5,1-ij]quinolin-2-amine hydrochloride; yield 60%. LC-MS (m/z) (M+1). ¹H NMR (300 MHz, DMSO) 7.07 (t, J=5.5 Hz, 1H), 3.84 (t, J=5.5 Hz, 2H), 3.60-3.53 (m, 4H), 3.49 (dd, J=12.7, 6.6 Hz, 2H), 2.75 (t, J=6.0 Hz, 2H), 2.57-2.51 (m, 2H), 2.44-2.43 (m, 4H), 2.13-2.02 (m, 2H).

The following compounds were prepared by the procedure of Example 2A, using the appropriate starting materials:

| Ex. | Product | ¹H NMR | m/z | RT [min] | Starting materials |
|---|---|---|---|---|---|
| 2B | 7,8,9-tribromo-N-[2-(pyrrolidin-1-yl)ethyl]-5,6-dihydro-4H-imidazo[4,5,1-ij]quinolin-2-amine hydrochloride | ¹H NMR (300 MHz, DMSO) δ 10.88 (bs, 1H), 4.09-4.00 (m, 2H), 3.87 (d, J = 4.9 Hz, 2H), 3.43 (d, J = 3.9 Hz, 2H), 3.07-3.05 (m, 4H), 2.80 (t, J = 5.9 Hz, 2H), 2.18-2.07 (m, 2H), 1.95 (d, J = 0.5 Hz, 4H) | 507.1 | 2.9 | 2,7,8,9-tetrabromo-5,6-dihydro-4H-imidazo[4,5,1-ij]quinoline<br><br>Method 1A and N-(2-aminoethyl)pyrrolidine (commercial) |
| 2C | (1R,2R)-N,N′-dimethyl-N-(7,8,9-tribromo-5,6-dihydro-4H-imidazo[4,5,1-ij]quinolin-2-yl)cyclohexane-1,2-diamine hydrochloride |  | 535.1 | 3.5 | 2,7,8,9-tetrabromo-5,6-dihydro-4H-imidazo[4,5,1-ij]quinoline<br><br>Method 1A and trans-N,N′-dimethylcyclohexane-1,2-diamine (commercial) |

3.3. Example 3

1-(7,8,9-tribromo-5,6-dihydro-4H-imidazo[4,5,1-ij]quinolin-2-yl)piperidin-4-ol

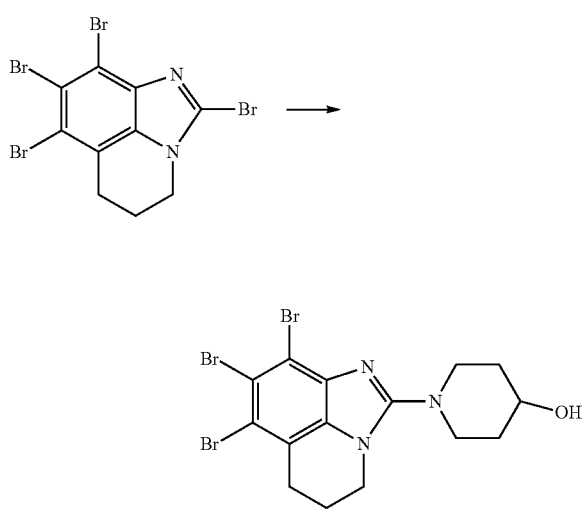

Example 3A

A 2,7,8,9-tetrabromo-5,6-dihydro-4H-imidazo[4,5,1-ij]quinoline (Method 1A) (0.1 g, 0.2 mmol), 4-hydroxypiperidine (0.06 g, 0.6 mmol) in ethanol (1 mL) were heated at 170° C. under microwave irradiation until the reaction was complete. The reaction mixture was allowed to cool to ambient temperature, then solvent was evaporated under reduced pressure. Crude product was purified by column chromatography (silica gel, dichloromethane/methanol 99:1) to gave 0.05 g of 1-(7,8,9-tribromo-5,6-dihydro-4H-imidazo[4,5,1-ij]quinolin-2-yl)piperidin-4-ol; yield 50%. LC-MS (m/z) (M+1). ¹H NMR (300 MHz, DMSO) δ 4.77 (d, J=4.2 Hz, 1H), 4.02 (t, J=5.7 Hz, 2H), 3.73-3.55 (m, 3H), 3.17-3.05 (m, 2H), 2.81 (t, J=6.0 Hz, 2H), 2.10-1.99 (m, 2H), 1.90-1.79 (m, 2H), 1.60-1.45 (m, 2H).

The following compounds were prepared by the procedure of Example 3A, using the appropriate starting materials:

| Ex. | Product | ¹HNMR | m/z | RT [min] | Starting materials |
|---|---|---|---|---|---|
| 3B | 7,8,9-tribromo-N-(pyridin-4-yl)-5,6-dihydro-4H-imidazo[4,5,1-ij]quinolin-2-amine | ¹H NMR (600 MHz, DMSO) δ 9.03 (bs, 1H), 8.58 (d, J = 6.8 Hz, 2H), 7.06 (d, J = 6.7 Hz, 2H), 4.26-4.25 (m, 2H), 2.97-2.95 (m, 2H), 2.22-2.20 (m, 2H) | 490.0 | 2.4 | 2,7,8,9-tetrabromo-5,6-dihydro-4H-imidazo[4,5,1-ij]quinoline<br><br>Method 1A and 4-amino-pyridine (commercial) |
| 3C | 7,8,9-tribromo-N-phenyl-5,6-dihydro-4H-imidazo[4,5,1-ij]quinolin-2-amine | ¹H NMR (600 MHz, DMSO) δ 9.32 (bs, 1H), 7.91 (d, J = 8.6 Hz, 2H), 7.37-7.33 (m, 2H), 7.02-6.98 (m, 1H), 4.13-4.10 (m, 2H), 2.85 (t, J = 6.1 Hz, 2H), 2.21-2.16 (m, 2H) | 486.0 | 4.0 | 2,7,8,9-tetrabromo-5,6-dihydro-4H-imidazo[4,5,1-ij]quinoline<br><br>Method 1A and aniline (commercial) |
| 3D | 7,8,9-tribromo-2-(piperidin-1-yl)-5,6-dihydro-4H-imidazo[4,5,1-ij]quinoline | ¹H NMR (600 MHz, DMSO) δ 4.03 (t, J = 5.7 Hz, 2H), 3.40-3.34 (m, 4H), 2.83 (t, J = 6.0 Hz, 2H), 2.13-2.03 (m, 2H), 1.66 (d, J = 4.0 Hz, 4H), 1.62 (d, J = 4.4 Hz, 2H) | 478.0 | 3.4 | 2,7,8,9-tetrabromo-5,6-dihydro-4H-imidazo[4,5,1-ij]quinoline<br><br>Method 1A and piperidine (commercial) |

| Ex. | Product | ¹HNMR | m/z | RT [min] | Starting materials |
|---|---|---|---|---|---|
| 3E | 7,8,9-tribromo-N-cyclohexyl-5,6-dihydro-4H-imidazo[4,5,1-ij]quinolin-2-amine 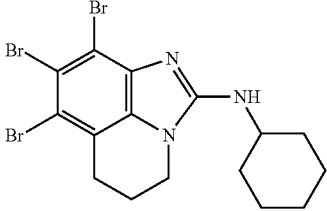 | ¹H NMR (600 MHz, DMSO) δ 6.88 (d, J = 7.9 Hz, 1H), 3.90-3.85 (m, 2H), 3.79-3.73 (m, 1H), 2.77 (t, J = 6.1 Hz, 2H), 2.12-2.06 (m, 2H), 1.99 (d, J = 10.6 Hz, 2H), 1.78-1.73 (m, 2H), 1.65-1.60 (m, 1H), 1.39-1.26 (m, 4H), 1.19-1.11 (m, 1H) | 492.1 | 2.9 | 2,7,8,9-tetrabromo-5,6-dihydro-4H-imidazo[4,5,1-ij]quinoline 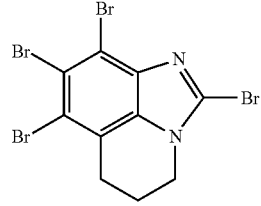<br><br>Method 1A and cyclohexanamine (commercial) |
| 3F | 3-[(7,8,9-tribromo-5,6-dihydro-4H-imidazo[4,5,1-ij]quinolin-2-yl)amino]propan-1-ol 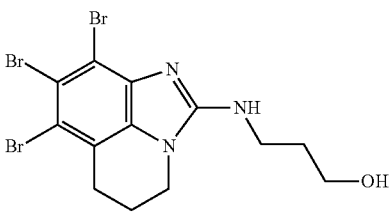 | ¹H NMR (600 MHz, DMSO) δ 7.14 (t, J = 5.6 Hz, 1H), 3.88-3.85 (m, 2H), 3.49 (q, J = 6.0 Hz, 2H), 3.47-3.44 (m, 2H), 2.77 (t, J = 6.1 Hz, 2H), 2.13-2.07 (m, 2H), 1.75 (q, J = 6.5 Hz, 2H) | 468.0 | 2.3 | 2,7,8,9-tetrabromo-5,6-dihydro-4H-imidazo[4,5,1-ij]quinoline 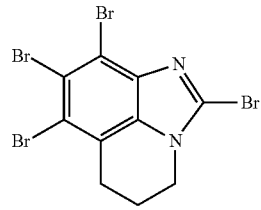<br><br>Method 1A and 3-aminopropanol (commercial) |
| 3G | 7,8,9-tribromo-2-(morpholin-4-yl)-5,6-dihydro-4H-imidazo[4,5,1-ij]quinoline 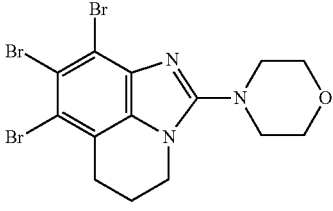 | ¹H NMR (600 MHz, DMSO) δ 4.07 (t, J = 5.8 Hz, 2H), 3.78-3.74 (m, 4H), 3.42-3.39 (m, 4H), 2.86-2.82 (m, 2H), 2.13-2.06 (m, 2H) | 480.0 | 3.3 | 2,7,8,9-tetrabromo-5,6-dihydro-4H-imidazo[4,5,1-ij]quinoline 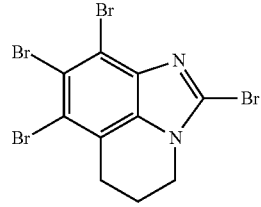<br><br>Method 1A and morpholine (commercial) |

| Ex. | Product | ¹HNMR | m/z | RT [min] | Starting materials |
|---|---|---|---|---|---|
| 3H | N-(7,8,9-tribromo-5,6-dihydro-4H-imidazo[4,5,1-ij]quinolin-2-yl)butane-1,4-diamine 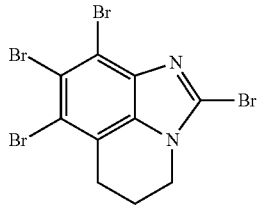 | ¹H NMR (600 MHz, DMSO) δ 7.66 (s, 2H), 7.25 (t, J = 5.4 Hz, 1H), 3.90-3.84 (m, 2H), 3.41 (q, J = 11.9, 6.1 Hz, 2H), 2.87 (t, J = 7.1 Hz, 2H), 2.78 (t, J = 6.0 Hz, 2H), 2.13-2.08 (m, 2H), 1.65 (m, 4H) | 481.0 | 2.0 | 2,7,8,9-tetrabromo-5,6-dihydro-4H-imidazo[4,5,1-ij]quinoline<br><br>Method 1A and butane-1,4-diamine (commercial) |
| 3I | 7,8,9-tribromo-N,N-diethyl-5,6-dihydro-4H-imidazo[4,5,1-ij]quinolin-2-amine 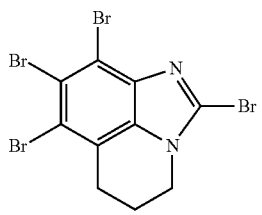 | ¹H NMR (300 MHz, DMSO) δ 4.06 (t, J = 5.7 Hz, 2H), 3.45 (q, J = 7.1 Hz, 4H), 2.79 (t, J = 6.1 Hz, 2H), 2.12-2.03 (m, 2H), 1.16 (t, J = 7.0 Hz, 6H) | 466.0 | 3.3 | 2,7,8,9-tetrabromo-5,6-dihydro-4H-imidazo[4,5,1-ij]quinoline<br><br>Method 1A and diethylamine (commercial) |
| 3J | 7,8,9-tribromo-5,6-dihydro-4H-imidazo[4,5,1-ij]quinolin-2-amine 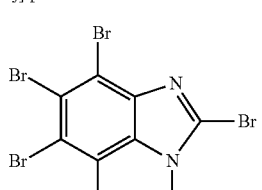 | ¹H NMR (600 MHz, DMSO) δ 6.97 (s, 2H), 3.90-3.84 (m, 2H), 2.77 (t, J = 6.1 Hz, 2H), 2.13-2.07 (m, 2H) | 410.0 | 2.4 | 2,7,8,9-tetrabromo-5,6-dihydro-4H-imidazo[4,5,1-ij]quinoline<br><br>Method 1A and sat. NH₃ in EtOH |

| Ex. | Product | ¹HNMR | m/z | RT [min] | Starting materials |
|---|---|---|---|---|---|
| 3K | N,N-dimethyl-N'-(7,8,9-tribromo-5,6-dihydro-4H-imidazo[4,5,1-ij]quinolin-2-yl)ethane-1,2-diamine | ¹H NMR (300 MHz, DMSO) δ 7.06 (t, J = 5.6 Hz, 1H), 3.84 (t, 2H), 3.46 (q, 2H), 2.75 (t, J = 6.1 Hz, 2H), 2.48-2.47 (m, 2H), 2.18 (s, 6H), 2.07 (q, 2H) | 481.0 | 2.5 | 2,7,8,9-tetrabromo-5,6-dihydro-4H-imidazo[4,5,1-ij]quinoline<br><br>Method 1A and N,N-dimethylethylenediamine (commercial) |
| 3L | 7,8,9-tribromo-N-[3-(pyrrolidin-1-yl)propyl]-5,6-dihydro-4H-imidazo[4,5,1-ij]quinolin-2-amine | ¹H NMR (300 MHz, DMSO) δ 7.17 (t, J = 5.4 Hz, 1H), 3.83 (t, J = 5.7 Hz, 2H), 3.64 (t, J = 6.7 Hz, 1H), 3.43-3.35 (m, 2H), 2.79-2.71 (m, 2H), 2.44-2.39 (m, 4H), 2.12-2.02 (m, 2H), 1.90 (t, J = 3.0 Hz, 1H), 1.82-1.72 (m, 2H), 1.70-1.61 (m, 4H) | 521.1 | 2.8 | 2,7,8,9-tetrabromo-5,6-dihydro-4H-imidazo[4,5,1-ij]quinoline<br><br>Method 1A and 1-(3-aminopropyl)pyrrolidine (commercial) |
| 3M | 7,8,9-tribromo-2-(4-methylpiperazin-1-yl)-5,6-dihydro-4H-imidazo[4,5,1-ij]quinoline | ¹H NMR (300 MHz, DMSO) δ 4.03 (t, J = 5.7 Hz, 2H), 3.41-3.35 (m, 4H), 2.81 (t, J = 6.0 Hz, 2H), 2.47-2.44 (m, 4H), 2.22 (s, 3H), 2.07 (dd, J = 9.9, 6.0 Hz, 2H) | 493.0 | 2.5 | 2,7,8,9-tetrabromo-5,6-dihydro-4H-imidazo[4,5,1-ij]quinoline<br><br>Method 1A and N-methylpiperazine (commercial) |

| Ex. | Product | ¹HNMR | m/z | RT [min] | Starting materials |
|---|---|---|---|---|---|
| 3N | 7,8,9-tribromo-2-(3,3-dimethylpiperazin-1-yl)-5,6-dihydro-4H-imidazo[4,5,1-ij]quinoline | ¹H NMR (300 MHz, DMSO) δ 8.94 (bs, 1H), 4.08 (t, J = 5.6 Hz, 2H), 3.59-3.50 (m, 3H), 3.37-3.29 (m, 6H), 2.83 (t, J = 5.9 Hz, 2H), 2.16-2.03 (m, 2H), 1.39 (s, 6H) | 507.1 | 2.8 | 2,7,8,9-tetrabromo-5,6-dihydro-4H-imidazo[4,5,1-ij]quinoline<br><br>Method 1A and 2,2-dimethylpiperazine (commercial) |
| 3O | 1-(7,8,9-tribromo-5,6-dihydro-4H-imidazo[4,5,1-ij]quinolin-2-yl)piperidin-3-ol | ¹H NMR (300 MHz, DMSO) δ 4.93 (d, J = 4.3 Hz, 1H), 4.03 (t, J = 5.6 Hz, 2H), 3.74-3.64 (m, 2H), 3.59-3.49 (m, 1H), 3.15-3.04 (m, 1H), 2.84-2.77 (m, 2H), 2.11-2.00 (m, 2H), 1.91-1.74 (m, 2H), 1.56 (dt, J = 13.4, 9.9 Hz, 1H), 1.38 (dt, J = 15.2, 4.0 Hz, 1H) | 494.0 | 2.8 | 2,7,8,9-tetrabromo-5,6-dihydro-4H-imidazo[4,5,1-ij]quinoline<br><br>Method 1A and 3-hydroxypiperidine (commercial) |
| 3P | 7,8,9-tribromo-2-(3-methylpiperazin-1-yl)-5,6-dihydro-4H-imidazo[4,5,1-ij]quinoline | | 493.0 | 2.6 | 2,7,8,9-tetrabromo-5,6-dihydro-4H-imidazo[4,5,1-ij]quinoline<br><br>Method 1A and 2-methylpiperazine (commercial) |

-continued

| Ex. | Product | ¹HNMR | m/z | RT [min] | Starting materials |
|---|---|---|---|---|---|
| 3R | 7,8,9-tribromo-2-(2-methylpyrrolidin-1-yl)-5,6-dihydro-4H-imidazo[4,5,1-ij]quinoline 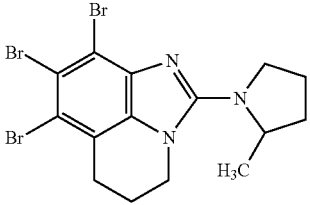 | ¹H NMR (300 MHz, DMSO) δ 4.36-4.07 (m, 3H), 3.84-3.75 (m, 1H), 3.66-3.56 (m, 1H), 2.86-2.67 (m, 2H), 2.17-1.89 (m, 5H), 1.65-1.54 (m, 1H), 1.22 (d, J = 6.2 Hz, 3H) | 478.0 | 3.3 | 2,7,8,9-tetrabromo-5,6-dihydro-4H-imidazo[4,5,1-ij]quinoline<br><br>Method 1A and 2-methylpyrrolidine (commercial) |
| 3S | 7,8-dibromo-9-iodo-2-(2-methylpyrrolidin-1-yl)-5,6-dihydro-4H-imidazo[4,5,1-ij]quinoline 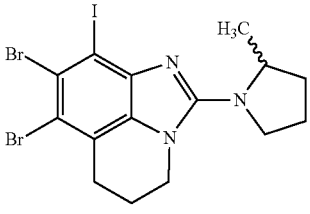 | | 525.0 | 3.3 | 7,8-dibromo-2-chloro-9-iodo-5,6-dihydro-4H-imidazo[4,5,1-ij]quinoline<br><br>Method 6 and 2-methylpyrrolidine (commercial) |
| 3T | 7,8-dibromo-9-iodo-2-[(3R)-3-methylpiperazin-1-yl]-5,6-dihydro-4H-imidazo[4,5,1-ij]quinoline 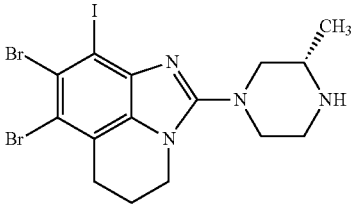 | ¹H NMR (300 MHz, DMSO) δ 4.01 (t, J = 5.7 Hz, 2H), 3.68-3.58 (m, 2H), 2.94-2.87 (m, 2H), 2.86-2.78 (m, 4H), 2.53 (d, J = 10.4 Hz, 1H), 2.08-2.03 (m, 2H), 1.00 (d, J = 6.3 Hz, 3H) | 540.0 | 2.7 | 7,8-dibromo-2-chloro-9-iodo-5,6-dihydro-4H-imidazo[4,5,1-ij]quinoline<br><br>Method 6 and (R)-2-methylpiperazine (commercial) |

-continued

| Ex. | Product | ¹HNMR | m/z | RT [min] | Starting materials |
|---|---|---|---|---|---|
| 3U | [1-(7,8,9-tribromo-5,6-dihydro-4H-imidazo[4,5,1-ij]quinolin-2-yl)piperidin-3-yl]methanol | ¹H NMR (300 MHz, DMSO) δ 4.63 (t, J = 5.3 Hz, 1H), 4.06-3.98 (m, 2H), 3.83-3.75 (m, 1H), 3.73-3.63 (m, 1H), 3.46-3.33 (m, 2H), 3.02-2.91 (m, 1H), 2.84-2.79 (m, 2H), 2.13-1.98 (m, 2H), 1.83-1.52 (m, 4H), 1.25-1.08 (m, 1H) | 508.1 | 2.8 | 2,7,8,9-tetrabromo-5,6-dihydro-4H-imidazo[4,5,1-ij]quinoline; Method 1A and 3-piperidinemethanol (commercial) |
| 3W | 7,8-dibromo-2-(3,3-dimethylpiperazin-1-yl)-9-iodo-5,6-dihydro-4H-imidazo[4,5,1-ij]quinoline | ¹H NMR (300 MHz, dmso) δ 9.30 (bs, 1H), 4.05 (t, J = 5.5 Hz, 2H), 3.57-3.55 (m, 2H), 3.39-3.37 (m, 2H), 3.33-3.30 (m, 2H), 2.83 (t, J = 5.7 Hz, 2H), 2.16-2.02 (m, 2H), 1.41 (s, 6H) | 554.1 | 3.1 | 7,8-dibromo-2-chloro-9-iodo-5,6-dihydro-4H-imidazo[4,5,1-ij]quinoline; Method 6 and 2,2-dimethylpiperazine (commercial) |
| 3X | 7,8-dibromo-N,N-diethyl-9-iodo-5,6-dihydro-4H-imidazo[4,5,1-ij]quinolin-2-amine | | 513.0 | 3.7 | 7,8-dibromo-2-chloro-9-iodo-5,6-dihydro-4H-imidazo[4,5,1-ij]quinoline; Method 6 and diethylamine (commercial) |

-continued

| Ex. | Product | ¹HNMR | m/z | RT [min] | Starting materials |
|---|---|---|---|---|---|
| 3Y | 7,8-dibromo-9-iodo-5,6-dihydro-4H-imidazo[4,5,1-ij]quinolin-2-amine | | 456.9 | 2.9 | 7,8-dibromo-2-chloro-9-iodo-5,6-dihydro-4H-imidazo[4,5,1-ij]quinoline<br><br>Method 6 and sat. NH₃ in EtOH |
| 3Z | 7,8,9-tribromo-N-(tetrahydro-2H-pyran-4-yl)-5,6-dihydro-4H-imidazo[4,5,1-ij]quinolin-2-amine | ¹H NMR (300 MHz, DMSO) δ 7.01 (d, J = 7.7 Hz, 1H), 4.00-3.83 (m, 5H), 3.48-3.36 (m, 2H), 2.75 (t, J = 6.0 Hz, 2H), 2.14-2.02 (m, 2H), 1.92 (dd, J = 12.5, 2.3 Hz, 2H), 1.62-1.44 (m, 2H) | 494.0 | 2.7 | 2,7,8,9-tetrabromo-5,6-dihydro-4H-imidazo[4,5,1-ij]quinoline<br><br>Method 1A and 4-aminotetrahydropyran (commercial) |
| 3AA | 7,8,9-tribromo-2-[(3S)-3-methylpiperazin-1-yl]-5,6-dihydro-4H-imidazo[4,5,1-ij]quinoline | ¹H NMR (300 MHz, DMSO) δ 4.03 (t, J = 5.7 Hz, 2H), 3.69-3.59 (m, 2H), 2.95-2.87 (m, 2H), 2.87-2.78 (m, 4H), 2.55 (dd, J = 12.0, 10.3 Hz, 1H), 2.11-1.99 (m, 2H), 1.00 (d, J = 6.3 Hz, 3H) | 493.0 | 2.6 | 2,7,8,9-tetrabromo-5,6-dihydro-4H-imidazo[4,5,1-ij]quinoline<br><br>Method 1A and (S)-2-methylpiperazine (commercial) |

-continued

| Ex. | Product | ¹HNMR | m/z | RT [min] | Starting materials |
|---|---|---|---|---|---|
| 3AB | 7,8,9-tribromo-2-[(3R)-3-methylpiperazin-1-yl]-5,6-dihydro-4H-imidazo[4,5,1-ij]quinoline | ¹H NMR (300 MHz, DMSO) δ 8.46 (s, 1H), 4.07 (t, J = 5.7 Hz, 2H), 3.90-3.78 (m, 2H), 3.37-3.29 (m, 4H), 3.06 (dd, J = 10.5, 3.1 Hz, 1H), 2.83 (t, J = 6.0 Hz, 2H), 2.17-1.99 (m, 2H), 1.24 (d, J = 6.5 Hz, 3H) | 493.0 | 2.7 | 2,7,8,9-tetrabromo-5,6-dihydro-4H-imidazo[4,5,1-ij]quinoline<br><br>Method 1A and (R)-2-methylpiperazine (commercial) |
| 3AC | (3R)-1-(7,8,9-tribromo-5,6-dihydro-4H-imidazo[4,5,1-ij]quinolin-2-yl)pyrrolidin-3-ol | ¹H NMR (300 MHz, DMSO) δ 5.04 (s, 1H), 4.36 (s, 1H), 4.31-4.15 (m, 2H), 3.77-3.71 (m, 2H), 3.53 (d, J = 10.6 Hz, 1H), 2.82-2.69 (m, 2H), 2.19-1.80 (m, 4H) | 480.0 | 2.6 | 2,7,8,9-tetrabromo-5,6-dihydro-4H-imidazo[4,5,1-ij]quinoline<br><br>Method 1A and (3R)-3-hydroxypyrrolidine (commercial) |
| 3AD | 7,8-dibromo-9-iodo-2-[(3R)-3-methylpiperazin-1-yl]-5,6-dihydro-4H-imidazo[4,5,1-ij]quinoline | ¹H NMR (300 MHz, DMSO) δ 8.50 (s, 1H), 4.04 (t, J = 5.6 Hz, 2H), 3.79 (d, J = 13.2 Hz, 2H), 3.28-3.10 (m, 4H), 3.02-3.0 (m, 1H), 2.82 (t, J = 6.0 Hz, 2H), 2.17-2.01 (m, 2H), 1.23 (d, J = 6.4 Hz, 3H) | 540.0 | 2.9 | 7,8-dibromo-2-chloro-9-iodo-5,6-dihydro-4H-imidazo[4,5,1-ij]quinoline<br><br>Method 6 and (R)-2-methylpiperazine (commercial) |

| Ex. | Product | ¹HNMR | m/z | RT [min] | Starting materials |
|---|---|---|---|---|---|
| 3AE | 7,8-dibromo-9-methyl-2-(2-methylpyrrolidin-1-yl)-5,6-dihydro-4H-imidazo[4,5,1-ij]quinoline | | 413.2 | 3.1 | 7,8-dibromo-2-chloro-9-methyl-5,6-dihydro-4H-imidazo[4,5,1-ij]quinoline<br><br>Method 2A and 2-methylpyrrolidine (commercial) |
| 3AF | 7,8,9-tribromo-N-[2-(4-methylpiperazin-1-yl)ethyl]-5,6-dihydro-4H-imidazo[4,5,1-ij]quinolin-2-amine | ¹H NMR (300 MHz, DMSO) δ 7.07 (t, J = 5.5 Hz, 1H), 3.84 (t, J = 5.6 Hz, 2H), 3.48 (dd, J = 12.6, 6.6 Hz, 2H), 2.75 (t, J = 6.0 Hz, 2H), 2.58-2.49 (m, 6H), 2.41-2.39 (m, 4H), 2.20-2.18 (m, 3H), 2.13-2.03 (m, 2H) | 536.1 | 12.3 | 2,7,8,9-tetrabromo-5,6-dihydro-4H-imidazo[4,5,1-ij]quinoline<br><br>Method 1A and 2-(4-methylpiperazin-1-yl)ethanamine (commercial) |
| 3AG | 7,8-dibromo-2-[(3R,5S)-3,5-dimethylpiperazin-1-yl]-9-methyl-5,6-dihydro-4H-imidazo[4,5,1-ij]quinoline | ¹H NMR (600 MHz, DMSO) δ 4.08 (t, J = 5.8 Hz, 2H), 3.67-3.63 (m, 2H), 3.00-2.94 (m, 2H), 2.88 (t, J = 6.0 Hz, 2H), 2.58 (s, 3H), 2.53-2.49 (m, 2H), 2.14-2.09 (m, 2H), 1.07 (s, 3H), 1.06 (s, 3H) | 442.2 | 2.5 | 7,8-dibromo-2-chloro-9-methyl-5,6-dihydro-4H-imidazo[4,5,1-ij]quinoline<br><br>Method 2A and (2R,6S)-2,6-dimethylpiperazine (commercial) |

-continued

| Ex. | Product | ¹HNMR | m/z | RT [min] | Starting materials |
|---|---|---|---|---|---|
| 3AH | 7,8-dibromo-9-methyl-2-(3-methylpiperazin-1-yl)-5,6-dihydro-4H-imidazo[4,5,1-ij]quinoline | ¹H NMR (600 MHz, DMSO) δ 4.02 (t, J = 5.0 Hz, 2H), 3.60-3.56 (m, 2H), 2.93 (dd, J = 7.4, 2.4 Hz, 1H), 2.90-2.84 (m, 4H), 2.83 (t, J = 6.1 Hz, 3H), 2.53 (s, 3H), 2.11-2.01 (m, 2H), 1.02 (d, J = 6.3 Hz, 3H) | 428.2 | 2.3 | 7,8-dibromo-2-chloro-9-methyl-5,6-dihydro-4H-imidazo[4,5,1-ij]quinoline<br><br>Method 2A and 2-methylpiperazine (commercial) |
| 3AI | 7,8-dibromo-2-(3,3-dimethylpiperazin-1-yl)-9-methyl-5,6-dihydro-4H-imidazo[4,5,1-ij]quinoline | ¹H NMR (600 MHz, DMSO) δ 4.01 (t, J = 5.8 Hz, 2H), 3.23-3.20 (m, 2H), 3.03 (s, 2H), 2.94-2.91 (m, 2H), 2.84 (t, J = 6.0 Hz, 2H), 2.52 (s, 3H), 2.10-2.05 (m, 2H), 1.14 (s, 6H) | 442.2 | 2.4 | 7,8-dibromo-2-chloro-9-methyl-5,6-dihydro-4H-imidazo[4,5,1-ij]quinoline<br><br>Method 2A and 2,2-dimethylpiperazine (commercial) |
| 3AJ | 7,8,9-tribromo-N-[3-(morpholin-4-yl)propyl]-5,6-dihydro-4H-imidazo[4,5,1-ij]quinolin-2-amine | ¹H NMR (600 MHz, DMSO) δ 7.13 (t, J = 5.5 Hz, 1H), 3.88-3.84 (m, 2H), 3.59 (t, J = 4.6 Hz, 4H), 3.42 (dd, J = 12.9, 6.8 Hz, 2H), 2.77 (t, J = 6.1 Hz, 2H), 2.40-2.35 (m, 6H), 2.13-2.07 (m, 2H), 1.81-1.75 (m, 2H) | 537.1 | 2.8 | 2,7,8,9-tetrabromo-5,6-dihydro-4H-imidazo[4,5,1-ij]quinoline<br><br>Method 1A and N-(3-aminopropyl)morpholine (commercial) |

| Ex. | Product | ¹HNMR | m/z | RT [min] | Starting materials |
|---|---|---|---|---|---|
| 3AK | 7,8-dibromo-9-methyl-2-(4-methylpiperazin-1-yl)-5,6-dihydro-4H-imidazo[4,5,1-ij]quinoline 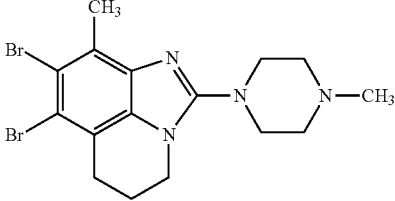 | | 428.2 | 2.4 | 7,8-dibromo-2-chloro-9-methyl-5,6-dihydro-4H-imidazo[4,5,1-ij]quinoline<br><br>Method 2A and N-methylpiperazine (commercial) |
| 3AL | N,N-dimethyl-1-(7,8,9-tribromo-5,6-dihydro-4H-imidazo[4,5,1-ij]quinolin-2-yl)pyrrolidin-3-amine 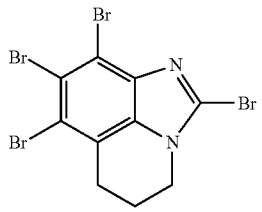 | ¹H NMR (300 MHz, DMSO) δ 4.23 (t, J = 5.4 Hz, 2H), 3.90-3.75 (m, 2H), 3.69-3.59 (m, 1H), 2.85-2.66 (m, 4H), 2.19 (s, 6H), 2.14-1.95 (m, 3H), 1.84-1.70 (m, 1H) | 507.1 | 3.8 | 2,7,8,9-tetrabromo-5,6-dihydro-4H-imidazo[4,5,1-ij]quinoline<br><br>Method 1A and N,N-dimethylpyrrolidin-3-amine (commercial) |
| 3AM | 7,8-dibromo-9-iodo-2-(4-methylpiperazin-1-yl)-5,6-dihydro-4H-imidazo[4,5,1-ij]quinoline 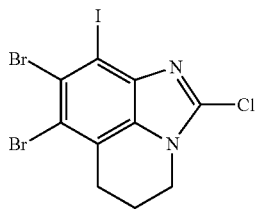 | ¹H NMR (300 MHz, DMSO) δ 4.01 (t, J = 5.7 Hz, 2H), 3.41-3.33 (m, 4H), 2.81 (t, J = 6.0 Hz, 2H), 2.48-2.43 (m, 4H), 2.22 (s, 3H), 2.05 (dt, J = 11.6, 6.0 Hz, 2H) | 540.0 | 2.8 | 7,8-dibromo-2-chloro-9-iodo-5,6-dihydro-4H-imidazo[4,5,1-ij]quinoline<br><br>Method 6 and N-methylpiperazine (commercial) |

| Ex. | Product | ¹HNMR | m/z | RT [min] | Starting materials |
|---|---|---|---|---|---|
| 3AN | (3S)-1-(7,8,9-tribromo-5,6-dihydro-4H-imidazo[4,5,1-ij]quinolin-2-yl)pyrrolidin-3-ol 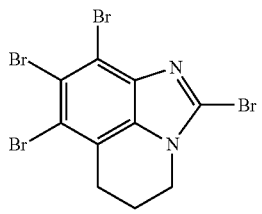 | ¹H NMR (300 MHz, DMSO) δ 5.03 (s, 1H), 4.35 (s, 1H), 4.26-4.18 (m, 2H), 3.77-3.70 (m, 3H), 3.53 (d, J = 10.6 Hz, 1H), 2.81-2.71 (m, 2H), 2.09-1.82 (m, 4H) | 480.0 | 2.7 | 2,7,8,9-tetrabromo-5,6-dihydro-4H-imidazo[4,5,1-ij]quinoline<br><br>Method 1A and (S)-3-hydroxypyrrolidine (commercial) |
| 3AO | 1-(7,8-dibromo-9-iodo-5,6-dihydro-4H-imidazo[4,5,1-ij]quinolin-2-yl)piperidin-4-ol 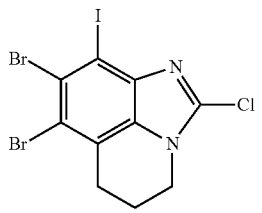 | ¹H NMR (300 MHz, DMSO) δ 4.77 (d, J = 4.2 Hz, 1H), 4.00 (t, J = 5.7 Hz, 2H), 3.74-3.59 (m, 4H), 3.16-3.05 (m, 2H), 2.80 (t, J = 5.9 Hz, 2H), 2.05 (dt, J = 11.6, 5.7 Hz, 2H), 1.89-1.80 (m, 2H), 1.52 (qd, J = 9.7, 3.7 Hz, 2H) | 541.0 | 2.8 | 7,8-dibromo-2-chloro-9-iodo-5,6-dihydro-4H-imidazo[4,5,1-ij]quinoline<br><br>Method 6 and 4-hydroxypiperidine (commercial) |
| 3AP | 7,8-dibromo-N,N-diethyl-9-methyl-5,6-dihydro-4H-imidazo[4,5,1-ij]quinolin-2-amine 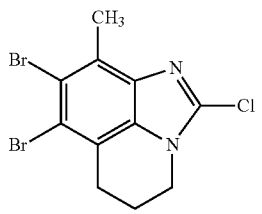 | ¹H NMR (600 MHz, CDCl₃) δ 4.14-4.11 (m, 2H), 3.73 (q, J = 7.2 Hz, 4H), 2.98 (t, J = 6.1 Hz, 2H), 2.70 (s, 3H), 2.29-2.24 (m, 2H), 1.35 (t, J = 7.2 Hz, 6H) | 401.1 | 2.9 | 7,8-dibromo-2-chloro-9-methyl-5,6-dihydro-4H-imidazo[4,5,1-ij]quinoline<br><br>Method 2A and diethylamine (commercial) |

| Ex. | Product | ¹HNMR | m/z | RT [min] | Starting materials |
|---|---|---|---|---|---|
| 3AR | (3S)-1-(7,8-dibromo-9-methyl-5,6-dihydro-4H-imidazo[4,5,1-ij]quinolin-2-yl)pyrrolidin-3-amine | ¹H NMR (300 MHz, dmso) δ 3.98 (t, J = 5.7 Hz, 2H), 3.63-3.56 (m, 4H), 2.82 (t, J = 5.9 Hz, 2H), 2.78-2.74 (m, 4H), 2.51 (s, 3H), 2.09-2.00 (m, 2H) | 431.2 | 7.6 | 7,8-dibromo-2-chloro-9-methyl-5,6-dihydro-4H-imidazo[4,5,1-ij]quinoline<br><br>Method 2A and 4-thiomorpholine (commercial) |
| 3AS | 7,8-dibromo-9-methyl-2-[(2S)-2-methylpiperazin-1-yl]-5,6-dihydro-4H-imidazo[4,5,1-ij]quinoline | | 428.2 | 3.6 | 7,8-dibromo-2-chloro-9-methyl-5,6-dihydro-4H-imidazo[4,5,1-ij]quinoline<br><br>Method 2A and (S)-tert-butyl 3-methylpiperazine-1-carboxylate (commercial) |
| 3AT | 7,8-dibromo-9-methyl-2-[(3R)-3-methylpiperazin-1-yl]-5,6-dihydro-4H-imidazo[4,5,1-ij]quinoline | ¹H NMR (300 MHz, DMSO) δ 4.00 (t, J = 5.7 Hz, 2H), 3.60-3.52 (m, 2H), 2.95-2.78 (m, 6H), 2.50 (s, 1H), 2.10-1.98 (m, 2H), 1.00 (d, J = 6.3 Hz, 3H) | 428.2 | 3.5 | 7,8-dibromo-2-chloro-9-methyl-5,6-dihydro-4H-imidazo[4,5,1-ij]quinoline<br><br>Method 2A and (R)-2-methylpiperazine (commercial) |

-continued

| Ex. | Product | ¹HNMR | m/z | RT [min] | Starting materials |
|---|---|---|---|---|---|
| 3AU | 7,8-dibromo-9-methyl-2-(morpholin-4-yl)-5,6-dihydro-4H-imidazo[4,5,1-ij]quinoline 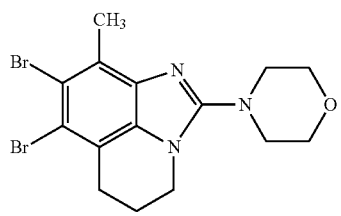 | | 415.1 | 5.9 | 7,8-dibromo-2-chloro-9-methyl-5,6-dihydro-4H-imidazo[4,5,1-ij]quinoline 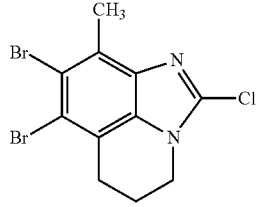<br><br>Method 2A and morpholine (commercial) |

3.4. Example 4

7,8,9-tribromo-2-(4-methoxypiperidin-1-yl)-5,6-dihydro-4H-imidazo[4,5,1-ij]quinoline

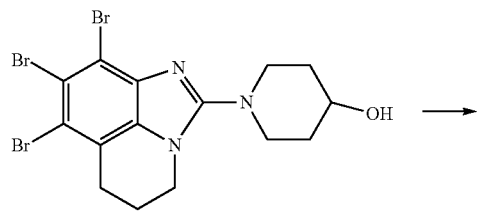

Example 4A

To a solution of 1-(7,8,9-tribromo-5,6-dihydro-4H-imidazo[4,5,1-ij]quinolin-2-yl)piperidin-4-ol (Example 2A) (0.1 g, 0.2 mmol) in acetonitrile (3 mL) cooled to 0° C. NaH (0.02 g, 0.4 mmol) was added. The reaction mixture was stirred for next 30 minutes at 0° C. and then iodomethane (0.03 mL, 0.4 mmol) was added. Next the mixture was stirred at room temperature overnight and solvent was evaporated under reduced pressure. The crude product was purified by flash chromatography (dichloromethane/methanol 9:1) to gave 0.04 g of 7,8,9-tribromo-2-(4-methoxypiperidin-1-yl)-5,6-dihydro-4H-imidazo[4,5,1-]quinoline; yield 39%; LC-MS (m/z) (M+1).

The following compounds were prepared by the procedure of Example 4A, using the appropriate starting materials:

| Ex. | Product | ¹H NMR | m/z | RT [min] | Starting materials |
|---|---|---|---|---|---|
| 4B | 7,8,9-tribromo-2-(4-ethoxypiperidin-1-yl)-5,6-dihydro-4H-imidazo[4,5,1-ij]quinoline 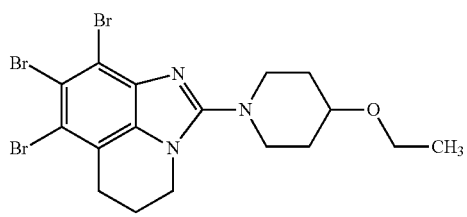 | | 522.1 | 3.5 | 1-(7,8,9-tribromo-5,6-dihydro-4H-imidazo[4,5,1-ij]quinolin-2-yl)piperidin-4-ol 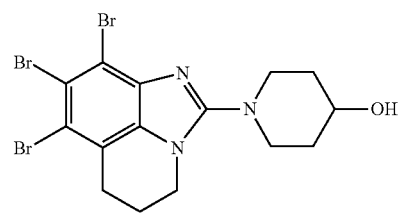<br><br>Example 2A and iodoethane (commercial) |

3.5. Example 5

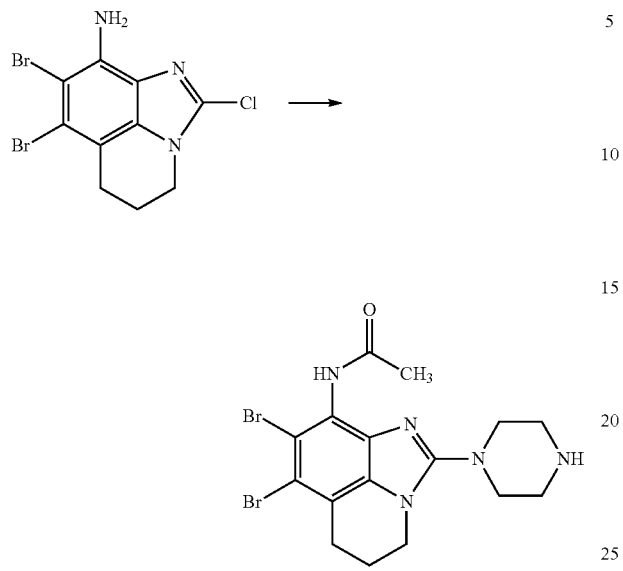

N-[7,8-dibromo-2-(piperazin-1-yl)-5,6-dihydro-4H-imidazo[4,5,1-ij]quinolin-9-yl]acetamide To a solution of acetyl chloride (0.18 mL, 2.5 mmol) in dichloromethane (5 mL) cooled to 0° C. suspension of 7,8-dibromo-2-chloro-5,6-dihydro-4H-imidazo[4,5,1-ij]quinolin-9-amine (Method 5) (0.2 g, 0.6 mmol) in dichloromethane (3 mL) was added portionwise. The reaction mixture was stirred for next 30 minutes at 0° C. then at room temperature overnight. To the reaction mixture water was added and organic phase was washed with saturated solution of sodium hydrogen carbonate. Organic layer was separated, dried over anhydrous sodium sulfate and concentrated under reduced pressure. The product was purified by column chromatography (silica gel, dichloromethane). The obtained product (0.07 g, 0.2 mmol) and t-butyl piperazine-1-carboxylate (0.1 g, 0.6 mmol) in ethanol (1.5 mL) were heated at 170° C. under microwave irradiation until the reaction was complete. The reaction mixture was allowed to cool to ambient temperature, then solvent was evaporated under reduced pressure. Crude product was purified by column chromatography (silica gel, dichloromethane/methanol 98:2). The obtained product (0.08 g, 0.14 mmol) was dissolved in methanol (0.5 mL) and 4M HCl in dioxane (1 mL) was added. The reaction mixture was stirred at room temperature overnight. The precipitated product was collected by filtration, purified by preparative HPLC and extracted with sodium hydrogen carbonate to gave 0.014 g of N-[7,8-dibromo-2-(piperazin-1-yl)-5,6-dihydro-4H-imidazo[4,5,1-ij]quinolin-9-yl]acetamide; yield 20% yield. LC-MS (m/z) 457.9 (M+1). $^1$H NMR (600 MHz, DMSO) δ 9.31 (s, 1H), 9.04 (s, 1H), 4.32-4.28 (m, 2H), 3.11-3.02 (m, 2H), 2.94 (t, J=6.0 Hz, 2H), 2.72 (s, 3H), 2.27-2.18 (m, 4H), 2.16-2.10 (m, J=12.0 Hz, 2H).

3.6. Example 6

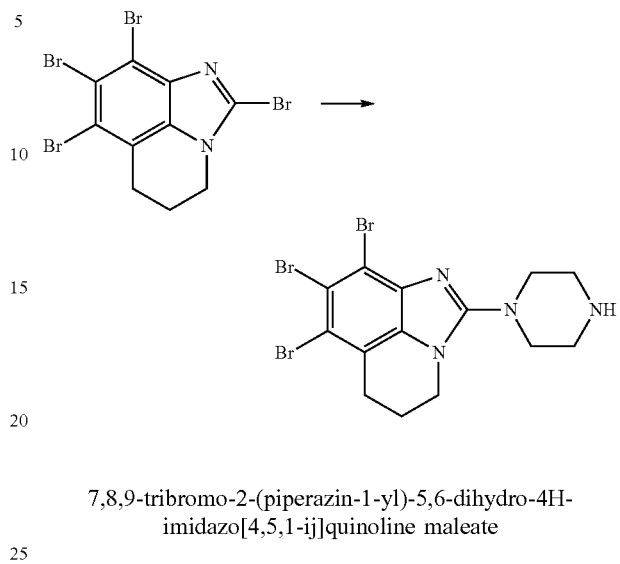

7,8,9-tribromo-2-(piperazin-1-yl)-5,6-dihydro-4H-imidazo[4,5,1-ij]quinoline maleate A mixture of 2,7,8,9-tetrabromo-5,6-dihydro-4H-imidazo[4,5,1-ij]quinoline (Method 1) (3 g, 6 mmol) and piperazine (2.7 g, 32 mmol) in ethanol (30 mL) was heated in sealed tube at 120° C. for 18 hrs. Reaction mixture was cooled down to the ambient temperature and solvent was removed under reduced pressure. The residue was dissolved in dichloromethane and washed with water. The organic layer was separated, dried over anhydrous sodium sulfate and concentrated under reduced pressure. The product (0.5 g, 1 mmol) was dissolved in methanol (600 mL) and maleic acid (0.2 g, 2 mmol) was added. The reaction mixture was stirred at room temperature for 1.5 hours than half of volume of solvent was removed under reduced pressure and the suspension was stirred at room temperature overnight. Precipitated white product was collected by filtration, washed with methanol, water and diethyl ether to gave 0.51 g of 7,8,9-tribromo-2-(piperazin-1-yl)-5,6-dihydro-4H-imidazo[4,5,1-ij]quinoline maleate; yield 82%. LC-MS (m/z) 478.8 (M+1). $^1$H NMR (600 MHz, DMSO) δ 8.64 (s, 1H), 6.02 (s, 2H), 4.08 (t, J=5.8 Hz, 2H), 3.61-3.57 (m, 4H), 3.28-3.25 (m, 4H), 2.85 (t, J=6.1 Hz, 2H), 2.13-2.08 (m, 2H).

3.7. Example 7

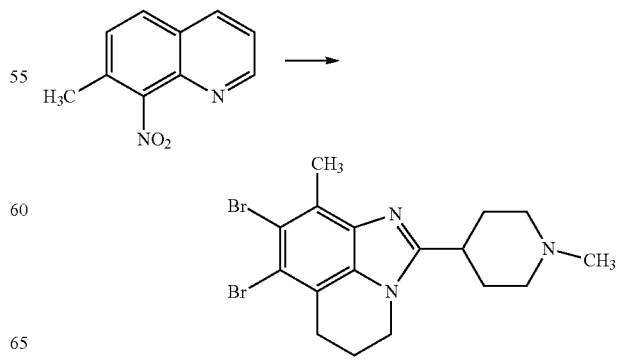

7,8-dibromo-9-methyl-2-(1-methylpiperidin-4-yl)-5,6-dihydro-4H-imidazo[4,5,1-ij]quinoline hydrochloride

Example 7A

To a 7-methyl-8-nitroquinoline (5 g, 26.6 mmol) suspended in ethanol (100 mL) Raney Nickel was added follow by hydrazine monohydrate (2.5 mL, 79.7 mmol). The reaction mixture was stirred at room temperature for 72 hrs. Then reaction mixture was filtered through Celite, washed by methanol and solvents were concentrated under reduced pressure. The crude was purified by column chromatography (silica gel, dichloromethane/methanol 9:1). 7-Methyl-8-aminoquinoline (1.6 g, 10.3 mmol) and 2-chloro-4,6-dimethoxy-1,3,5-triazine (CDMT) (3.6 g, 20.6 mmol) were added to the suspension of 1-methyl-4-piperidine carboxylic acid hydrochloride (1.8 g, 10.3 mmol) and N-methyl morpholine (3.4 mL, 30.1 mmol) in acetonitrile (80 mL). The reaction mixture was stirred at 40° C. for 24 hours. After cooled down to the ambient temperature the solvent was removed under reduced pressure. The residue was purified by column chromatography (silica gel, dichloromethane/methanol/triethylamine 8:2:0.1) to gave amide as a white solid. To the amide (1.9 g, 6.7 mmol) dissolved in acetic acid (15 mL) platinum oxide (0.15 g, 0.67 mmol) was added. The reaction was carried out in Parr apparatus under hydrogen atmosphere for 72 hours. Next the reaction mixture was filtered through Celite and washed with methanol. The filtrate was concentrated under reduced pressure. The product was purified by flash chromatography (silica gel, dichloromethane/methanol/triethylamine 9:1:0.2). To the suspension of obtained product (1.6 g, 5.8 mmol) in acetonitrile (70 mL)N-bromosuccinimide (2.3 g, 12.9 mmol) was added. The reaction mixture was stirred at room temperature for 15 minutes. The solvent was concentrated under reduced pressure and residue was purified by preparative HPLC. Then the product was dissolved in methanol and 4M HCl in dioxane was added. The reaction was stirred at room temperature overnight. The white precipitate was filtered off and washed by diethyl ether. The 7,8,9-tribromo-2-(1-methylpiperidin-4-yl)-5,6-dihydro-4H-imidazo[4,5,1-ij]quinoline hydrochloride (1.3 g) was obtained as a white solid; yield 52%. LC-MS (m/z) 491.8 (M+1); $^1$H NMR (600 MHz, DMSO) δ 10.70 (s, 1H), 4.31-4.25 (m, 2H), 3.55 (d, J=11.5 Hz, 2H), 3.11 (q, J=12.4 Hz, 2H), 2.95-2.91 (m, 2H), 2.77 (d, J=4.7 Hz, 3H), 2.69 (s, 3H), 2.33-2.25 (m, 2H), 2.24-2.20 (m, 2H), 2.18 (d, J=13.9 Hz, 2H).

The following compounds were prepared by the procedure of Example 7A, using the appropriate starting materials:

| Ex. | Product | $^1$H NMR | m/z | RT [min] | Starting materials |
| --- | --- | --- | --- | --- | --- |
| 7B | 7,8,9-tribromo-2-(1-methylpiperidin-4-yl)-5,6-dihydro-4H-imidazo[4,5,1-ij]quinoline hydrochloride | | 492.0 | 2.8 | 8-nitroquinoline (commercial) and 1-methylpiperidine-4-carboxylic acid (commercial) |
| 7C | 7,8-dibromo-9-methyl-2-(piperidin-4-yl)-5,6-dihydro-4H-imidazo[4,5,1-ij]quinoline hydrochloride | $^1$H NMR (600 MHz, DMSO) δ 9.31 (s, 1H), 9.04 (s, 1H), 4.32-4.28 (m, 2H), 3.11-3.02 (m, 2H), 2.94 (t, J = 6.0 Hz, 2H), 2.72 (s, 3H), 2.27-2.18 (m, 4H), 2.16-2.10 (m, J = 12.0 Hz, 2H) | 413.2 | 3.8 | 7-methyl-8-nitroquinoline (commercial) and 1-(trifluoroacetyl)piperidine-4-carboxylic acid |

| Ex. | Product | ¹H NMR | m/z | RT [min] | Starting materials |
|---|---|---|---|---|---|
| 7D | 7,8-dibromo-9-methyl-2-[1-(propan-2-yl)piperidin-4-yl]-5,6-dihydro-4H-imidazo[4,5,1-ij]quinoline hydrochloride | | 455.2 | 4.7 | 7-methyl-8-nitroquinoline (commercial) and 1-isopropylpiperidine-4-carboxylic acid (commercial) |
| 7E | 7,8,9-tribromo-2-(piperidin-4-yl)-5,6-dihydro-4H-imidazo[4,5,1-ij]quinoline hydrochloride | ¹H NMR (600 MHz, DMSO) δ 9.22 (d, J = 8.8 Hz, 1H), 8.85 (d, J = 8.6 Hz, 1H), 4.22-4.18 (m, 2H), 3.41-3.38 (m, 2H), 3.08-3.00 (m, 2H), 2.90 (t, J = 6.1 Hz, 2H), 2.23-2.17 (m, 2H), 2.13-2.03 (m, 4H) | 478.0 | 2.5 | 8-nitroquinoline (commercial) and 1-(trifluoroacetyl)piperidine-4-carboxylic acid |
| 7F | 7,8-dibromo-9-methyl-2-(piperidin-3-yl)-5,6-dihydro-4H-imidazo[4,5,1-ij]quinoline hydrochloride | ¹H NMR (300 MHz, DMSO) δ 9.13 (s, 1H), 4.20 (t, J = 5.7 Hz, 2H), 3.47-3.23 (m, 5H), 2.91 (t, J = 6.0 Hz, 2H), 2.66 (s, 3H), 2.23-2.07 (m, 4H), 1.87 (t, J = 6.4 Hz, 2H) | 413.2 | 4.9 | 7-methyl-8-nitroquinoline (commercial) and 1-(tert-butoxycarbonyl)piperidine-3-carboxylic acid (commercial) |

-continued

| Ex. | Product | ¹H NMR | m/z | RT [min] | Starting materials |
|---|---|---|---|---|---|
| 7G | 7,8-dibromo-9-methyl-2-[1-(propan-2-yl)piperidin-4-yl]-5,6-dihydro-4H-imidazo[4,5,1-ij]quinoline hydrochloride 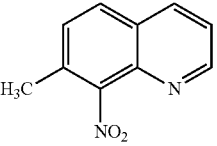 | | 414.1 | 3.7 | 7-methyl-8-nitroquinoline (commercial) 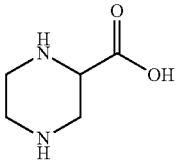 and piperizine-2-carboxylic acid dihydrochloride (commercial) 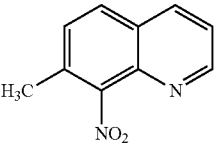 |
| 7H | 7,8-dibromo-2-(4-fluoro-piperidin-4-yl)-9-methyl-5,6-dihydro-4H-imidazo[4,5,1-ij]quinoline hydrochloride 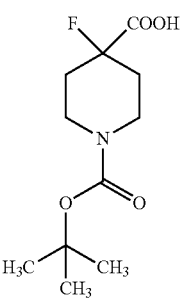 | | | | 7-methyl-8-nitroquinoline (commercial) 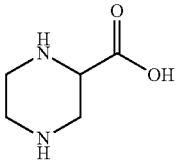 and 1-Boc-4-fluoro-4-piperidinecarboxylic acid (commercial) 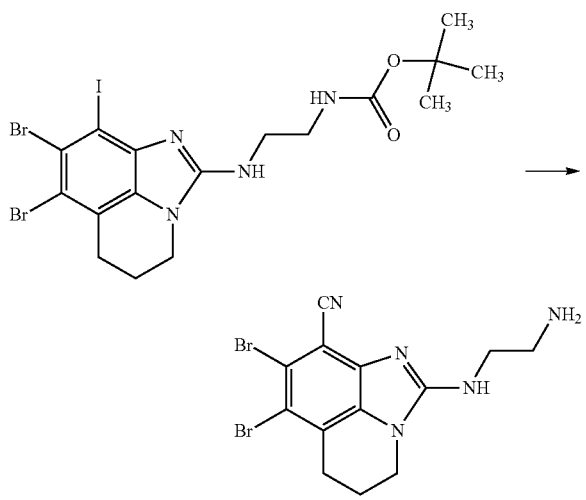 |

3.8. Example 8

2-[(2-aminoethyl)amino]-7,8-dibromo-5,6-dihydro-4H-imidazo[4,5,1-ij]quinoline-9-carbonitrile hydrochloride

Example 8A

A tert-butyl {2-[(7,8-dibromo-9-iodo-5,6-dihydro-4H-imidazo[4,5,1-ij]quinolin-2-yl)amino]ethyl}carbamate (Method 7A) (0.06 g, 0.1 mmol), copper (I) cyanide (0.02 g, 0.15 mmol) in acetonitrile (2 mL) were heated at 160° C. under microwave irradiation until the reaction was complete. The reaction mixture was allowed to cool to ambient temperature and then solvent was evaporated under reduced pressure. Crude product was purified by column chromatography (silica gel, dichloromethane/methanol 95:5). The obtained product (0.1 g, 0.17 mmol) was dissolved in methanol (0.5 mL) and 4M HCl in dioxane (1 mL) was added. The reaction mixture was stirred at room temperature overnight. The precipitated product was collected by filtration, washed with diethyl ether and dried to gave 0.016 g of 2-[(2-aminoethyl)amino]-7,8-dibromo-5,6-dihydro-4H-imidazo[4,5,1-ij]quinoline-9-carbonitrile hydrochloride; yield 25%; LC-MS (m/z) 425.8 (M+1).

The following compounds were prepared by the procedure of Example 8A, using the appropriate starting materials:

| Ex. | Product | ¹H NMR | m/z | RT [min] | Starting materials |
|---|---|---|---|---|---|
| 8B | 7,8-dibromo-9-cyano-2-(piperazin-1-yl)-5,6-dihydro-4H-imidazo[4,5,1-ij]quinoline hydrochloride 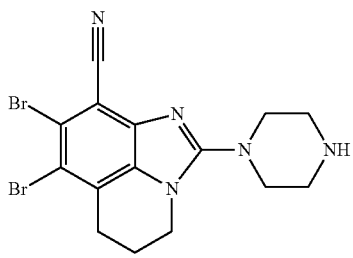 | | 425.1 | 2.5 | tert-butyl 4-(7,8-dibromo-9-iodo-5,6-dihydro-4H-imidazo[4,5,1-ij]quinolin-2-yl)piperizine-1-carboxylate 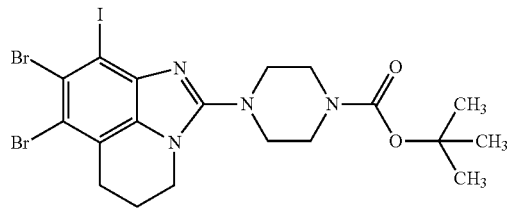<br>Method 7B |

3.9. Example 9

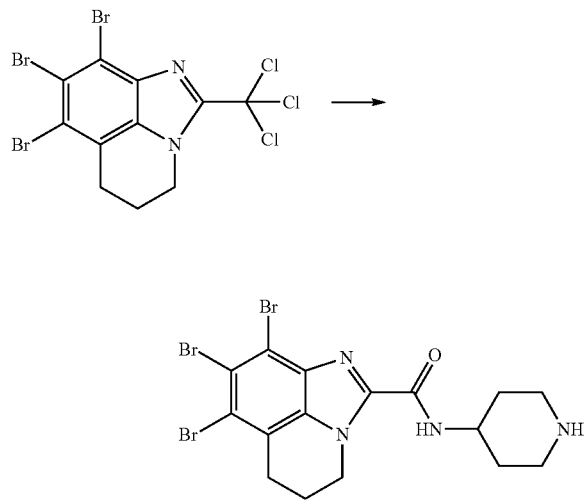

7,8,9-tribromo-N-(piperidin-4-yl)-5,6-dihydro-4H-imidazo[4,5,1-ij]quinoline-2-carboxamide hydrochloride (Example 9A)

A mixture of 2,2,2-trichloro-1-(7,8,9-tribromo-5,6-dihydro-4H-imidazo[4,5,1-ij]quinolin-2-yl)ethanone (Method 12) (0.29 g, 0.6 mmol), tert-butyl 4-aminopiperidine-1-carboxylate (0.23 g, 1.1 mmol) and potassium carbonate (0.23 g, 1.7 mmol) in mixture of acetonitrile (2 mL) and water (1 mL) were heated at 90° C. for 15 hrs. Organic layer was separated, dried over anhydrous sodium sulfate and solvent was evaporated under reduced pressure. The obtained product was dissolved in methanol (0.5 mL) and 4M HCl in dioxane (1 mL) was added. The reaction mixture was stirred at room temperature overnight. The precipitated product was collected by filtration, washed with diethyl ether and dried to gave 0.1 g of; yield 34%; LC-MS (m/z) 522.9 (M+1). ¹H NMR (300 MHz, DMSO) δ 9.08 (d, J=8.1 Hz, 1H), 8.73 (s, 1H), 4.56-4.47 (m, 2H), 4.09 (dd, J=12.8, 5.1 Hz, 1H), 3.07-2.93 (m, 2H), 2.94-2.86 (m, 2H), 2.23-2.11 (m, 2H), 1.97-1.83 (m, 4H).

The following examples were prepared by the procedure of Example 9A, using the appropriate starting materials:

| Ex. | Product | ¹H NMR | m/z | RT [min] | Starting materials |
|---|---|---|---|---|---|
| 9B | piperazin-1-yl(7,8,9-tribromo-5,6-dihydro-4H-imidazo[4,5,1-ij]quinolin-2-yl)methanone hydrochloride 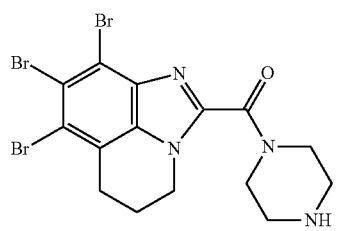 | ¹H NMR (300 MHz, DMSO) δ 9.15 (s, 1H), 4.37-4.30 (m, 2H), 4.26-4.19 (m, 2H), 3.93-3.85 (m, 2H), 3.26-3.18 (m, 4H), 2.92 (t, J = 6.0 Hz, 2H), 2.22-2.11 (m, 2H) | 507.0 | | 2,2,2-trichloro-1-(7,8,9-tribromo-5,6-dihydro-4H-imidazo[4,5,1-ij]quinolin-2-yl)ethanone 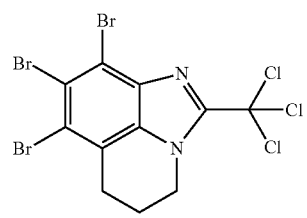<br>Method 12 and tert-butyl piperazine-1-carboxylate (commercial) |

| Ex. | Product | ¹H NMR | m/z | RT [min] | Starting materials |
|---|---|---|---|---|---|
| 9C | N-(2-aminoethyl)-7,8,9-tribromo-5,6-dihydro-4H-imidazo[4,5,1-ij]quinoline-2-carboxamide hydrochloride | ¹H NMR (300 MHz, DMSO) δ 9.04 (t, J = 6.0 Hz, 1H), 7.91 (s, 2H), 4.59-4.52 (m, 2H), 3.55 (dd, J = 12.0, 6.0 Hz, 2H), 3.00 (t, J = 6.0 Hz, 2H), 2.91 (t, J = 6.0 Hz, 2H), 2.24-2.12 (m, 2H) | 480.9 | | 2,2,2-trichloro-1-(7,8,9-tribromo-5,6-dihydro-4H-imidazo[4,5,1-ij]quinolin-2-yl)ethanone<br><br>Method 12 and tert-butyl 2-aminoethylcarbamate (commercial) |
| 9D | 7,8,9-tribromo-N-(2-hydroxyethyl)-5,6-dihydro-4H-imidazo[4,5,1-ij]quinoline-2-carboxamide hydrochloride | ¹H NMR (300 MHz, DMSO) δ 8.71 (t, J = 5.9 Hz, 1H), 4.82 (t, J = 5.5 Hz, 1H), 4.60-4.50 (m, 2H), 3.53 (dd, J = 11.6, 5.9 Hz, 2H), 3.41-3.34 (m, 2H), 2.89 (t, J = 6.0 Hz, 2H), 2.17 (dt, J = 11.4, 5.9 Hz, 2H) | 481.9 | | 2,2,2-trichloro-1-(7,8,9-tribromo-5,6-dihydro-4H-imidazo[4,5,1-ij]quinolin-2-yl)ethanone<br><br>Method 12 and 2-aminoethanol (commercial) |

3.10. Methods in Order to Prepare Compounds According to the Present Invention

3.10.1. Method 1

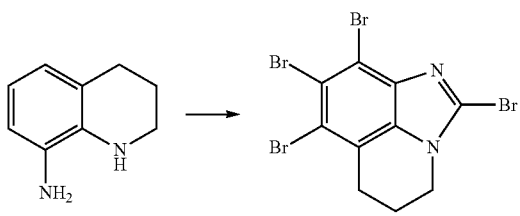 [SMILES: Nc1cccc2c1NCCC2 ; Brc1c(Br)c2c3c(nc(Br)n3CCC2)c1Br]

2,7,8,9-tetrabromo-5,6-dihydro-4H-imidazo[4,5,1-ij]quinoline (Method 1A)

1,2,3,4-Tetrahydroquinolin-8-amine (10 g, 67.5 mmol) (Method 11C) and potassium ethyl xanthogenate (11.9 g, 74.2 mmol) were dissolved in mixture of ethanol (50 mL) and water (5 mL) and the solution was refluxed for 16 h. Charcoal (4 g) was added, refluxed for 10 minutes and filtered. To the filtrate water (100 mL) was added followed by acetic acid (6 mL) and precipitated product was collected by filtration. The product was washed with water and dried on air. To the obtained product (4.4 g, 23.1 mmol) suspended in pre-cooled (0-5° C.) mixture of MeOH (100 mL) and hydrobromic acid (10 mL) bromine (4.74 mL, 92.5 mmol) was added portionswise within 45 min while temperature is maintained at 0-5° C. The reaction mixture was stirred at this temperature for additional 5 hours and then overnight at ambient temperature. Methanol was partially evaporated and yellow solid was precipitated by addition of water. The product was collected by filtration and re-suspended in water (150 mL). Bromine (8.8 mL, 172 mmol) was added and the reaction mixture was stirred overnight at 95° C. Pale yellow product was filtered off, washed with saturated solution of sodium sulfite, then water, and dried on air to gave 8.8 g of 2,7,8,9-tetrabromo-5,6-dihydro-4H-imidazo[4,5,1-ij]quinoline; yield 80%; LC-MS (m/z) 474.7 (M+1). ¹H NMR (600 MHz, DMSO) δ 4.19-4.02 (m, 2H), 2.89 (t, J=6.1 Hz, 2H), 2.30-2.15 (m, 2H).

The following starting compounds were prepared by the procedure of Method 1A, using the appropriate starting materials:

| Method | Product | ¹H NMR | m/z | RT [min] | Starting materials |
|---|---|---|---|---|---|
| 1B | 2,8,9-tribromo-7-methyl-5,6-dihydro-4H-imidazo[4,5,1-ij]quinoline | | 408.9 | 3.4 | 5-methyl-1,2,3,4-tetrahydroquinoline-8-amine<br><br>Method 10 |
| 1C | 2,7,9-tribromo-8-methoxy-5,6-dihydro-4H-imidazo[4,5,1-ij]quinoline | ¹H NMR (300 MHz, DMSO) δ 4.19-3.97 (m, 2H), 3.78 (s, 3H), 2.82 (t, J = 6.1 Hz, 2H), 2.29-2.03 (m, 2H) | 424.9 | 3.2 | 6-methoxy-8-amine-1,2,3,4-tetrahydroquinoline<br><br>Method 11A |

3.10.2. Method 2

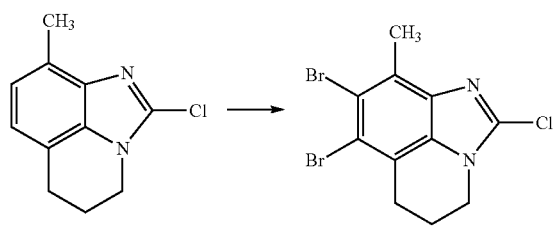 [SMILES: Cc1ccc2c3c1nc(Cl)n3CCC2 ; Cc1c(Br)c(Br)c2c3c1nc(Cl)n3CCC2]

7,8-dibromo-2-chloro-9-methyl-5,6-dihydro-4H-imidazo[4,5,1-ij]quinoline (Method 2A)

A 2-chloro-9-methyl-5,6-dihydro-4H-imidazo[4,5,1-ij]quinoline (11.7 g, 56 mmol) (Method 14A) was dissolved in acetonitrile (250 mL) cooled to 0° C. and next N-bromosuccinimide (50.0 g, 282 mmol) was added portion-wise over 1 h. The reaction mixture was stirred at 0° C. for 30 minutes then at room temperature for 48 hours. The solvent was evaporated under reduced pressure and residue was dissolved in dichloromethane and washed with saturated aqueous solution of sodium hydrogen carbonate. The organic layer was dried over anhydrous sodium sulfate, filtered and the filtrate was concentrated to gave 18.6 g of 7,8-dibromo-2-chloro-9-methyl-5,6-dihydro-4H-imidazo[4,5,1-ij]quinoline; yield 90%; LC-MS (m/z) 364.8 (M+1). ¹H NMR (600 MHz, DMSO) δ 4.12 (t, 2H, CH₂), 2.88 (t, 2H, CH₂), 2.57 (s, 3H, CH₃), 2.22-2.18 (m, 2H, CH₂).

The following starting compounds were prepared by the procedure of Method 2A, using the appropriate starting materials:

| Method | Product | ¹H NMR | m/z | RT [min] | Starting material |
|---|---|---|---|---|---|
| 2B | 7,8,9-tribromo-2-chloro-4-methyl-5,6-dihydro-4H-imidazo[4,5,1-ij]quinoline | | 443.4 | 3.7 | 2-chloro-4-methyl-5,6-dihydro-4H-imidazo[4,5,1-ij]quinoline<br><br>Method 14G |

3.10.3. Method 3

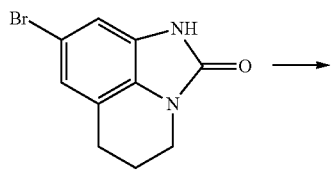

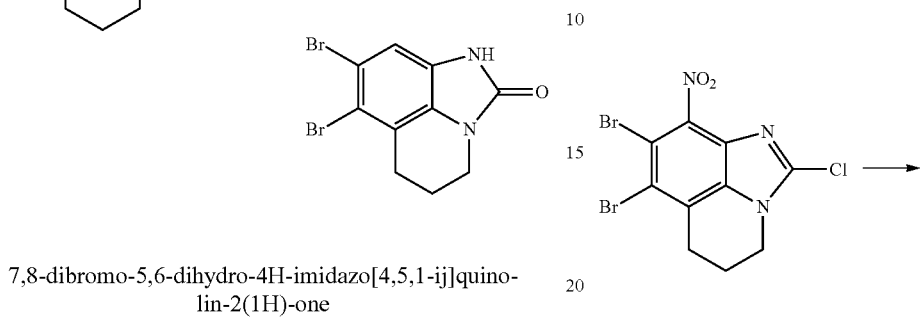

7,8-dibromo-5,6-dihydro-4H-imidazo[4,5,1-ij]quinolin-2(1H)-one

To a stirred solution of 8-bromo-5,6-dihydro-4H-imidazo[4,5,1-ij]quinolin-2-(1H)-one (prepared by the method described in EP1719761) (14.3 g, 56 mmol) in N,N-dimethylformamide (80 mL) cooled to 0° C. N-bromosuccinimide (10 g, 56 mmol) was added portionwise over 1 h. The reaction mixture was stirred at 0° C. for 4 hrs. Water was added to the reaction mixture, and the precipitated product was collected by filtration, washed with water and air dried to gave 17.4 g of 7,8-dibromo-5,6-dihydro-4H-imidazo[4,5,1-ij]quinolin-2(1H)-one; yield 93%; LC-MS (m/z) 332.8 (M+1). $^1$H NMR (600 MHz, DMSO) δ 10.90 (s, 1H), 7.18 (s, 1H), 3.76 3.57 (m, 2H), 2.77 (t, J=6.1 Hz, 2H), 2.13-1.98 (m, 2H).

3.10.5. Method 4

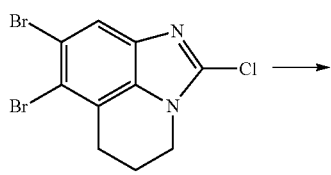

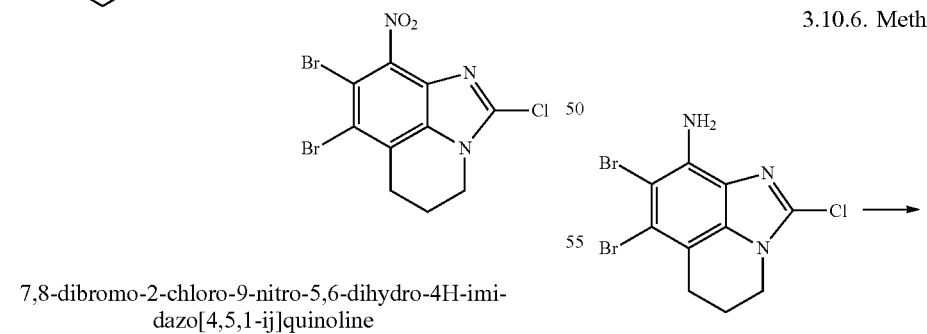

7,8-dibromo-2-chloro-9-nitro-5,6-dihydro-4H-imidazo[4,5,1-ij]quinoline

To a solution of 7,8-dibromo-2-chloro-5,6-dihydro-4H-imidazo[4,5,1-]quinoline (Method 3) (2.0 g, 5.7 mmol) in concentrated sulfuric acid (10 mL) cooled to 0° C. potassium nitrate (0.6 g, 6.3 mmol) was added. The reaction mixture was stirred at 0° C. for 3 hrs then slowly allowed to reach ambient temperature at which it was stirred overnight. To the reaction mixture water was added and the precipitated product was collected by filtration and washed with water.

The crude product was purified by column chromatography (silica gel, dichloromethane) to gave 1.27 g of 7,8-dibromo-2-chloro-9-nitro-5,6-dihydro-4H-imidazo[4,5,1-]quinoline; yield 70%; LC-MS (m/z) 395.8 (M+1). $^1$H NMR (600 MHz, DMSO) δ 4.18 (t, J=5.7 Hz, 2H), 2.97 (t, J=6.1 Hz, 2H), 2.29-2.22 (m, 2H).

3.10.5. Method 5

7,8-dibromo-2-chloro-5,6-dihydro-4H-imidazo[4,5,1-ij]quinolin-9-amine

A 7,8-dibromo-2-chloro-9-nitro-5,6-dihydro-4H-imidazo[4,5,1-ij]quinoline (Method 4) (1.0 g, 2.5 mmol) and SnCl$_2$ (0.96 g, 5 mmol) were suspended in concentrated hydrochloric acid (5 mL) and stirred at room temperature overnight. Then the reaction mixture was poured into ice and precipitated product was filtered off, washed with water and air dried to gave 5.16 g of 7,8-dibromo-2-chloro-5,6-dihydro-4H-imidazo[4,5,1-ij]quinolin-9-amine; yield 90%; LC-MS (m/z) 365.8 (M+1). $^1$H NMR (600 MHz, DMSO) δ 5.67 (s, 1H), 4.09-4.06 (m, 2H), 2.79-2.76 (m, 2H), 2.18-2.12 (m, 2H).

3.10.6. Method 6

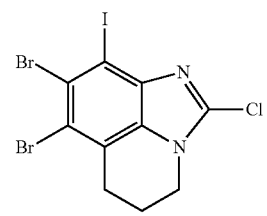

7,8-dibromo-2-chloro-9-iodo-5,6-dihydro-4H-imidazo[4,5,1-]quinoline

A 7,8-dibromo-2-chloro-5,6-dihydro-4H-imidazo[4,5,1-ij]quinolin-9-amine (Method 5) (4.3 g, 11.8 mmol) was suspended in a mixture of concentrated hydrochloric acid (12 mL) and water (3 mL). The suspension was cooled to −15° C. and sodium nitrite (0.9 g, 12.9 mmol) dissolved in water (15 mL) was added dropwise over 20 minutes. The mixture was stirred for 30 minutes at 0° C. and added dropwise over 10 minutes to a stirred solution of potassium iodide (17.6 g, 105.9 mmol) in water (150 mL). The reaction mixture was stirred overnight at room temperature and then treated with aqueous saturated solution of sodium sulfite. Product was extracted with dichloromethane and purified by column chromatography (silica gel, dichloromethane) to ethylenediamine (0.2 g, 1.3 mmol) in ethanol (2 mL) were heated at 170° C. under microwave irradiation until the reaction was complete. The reaction mixture was allowed to cool to ambient temperature, then solvent was evaporated under reduced pressure. Crude product was purified by column chromatography (silica gel, dichloromethane/methanol 98:2) to give 0.12 g of tert-butyl {2-[(7,8-dibromo-9-iodo-5,6-dihydro-4H-imidazo[4,5,1-ij]quinolin-2-yl)amino]ethyl}carbamate; yield 47%; LC-MS (m/z) 600.8 (M+1).

The following starting compounds were prepared by the procedure of Method 7A, using the appropriate starting materials:

| Method | Product | $^1$H NMR | m/z | RT [min] | Starting materials |
|---|---|---|---|---|---|
| 7B | tert-butyl 4-(7,8-dibromo-9-iodo-5,6-dihydro-4H-imidazo[4,5,1-ij]quinolin-2-yl)piperizine-1-carboxylate | | 626.1 | 4.3 | 7,8-dibromo-2-chloro-9-iodo-5,6-dihydro-4H-imidazo[4,5,1-ij]quinoline |

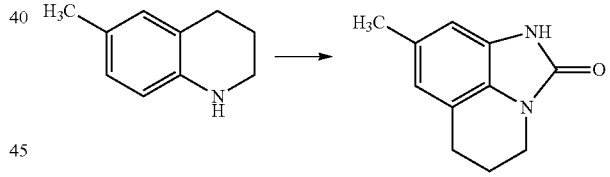

Method 6 and t-butyl piperazine-1-carboxylate (commercial)

gave 3.3 g of 7,8-dibromo-2-chloro-9-iodo-5,6-dihydro-4H-imidazo[4,5,1-ij]quinoline; yield 58%; LC-MS (m/z) 476.6 (M+1). $^1$H NMR (600 MHz, DMSO) δ 4.11 (t, 2H, CH$_2$), 2.88 (t, 2H, CH$_2$), 2.23-2.18 (m, 2H, CH$_2$).

3.10.7. Method 7

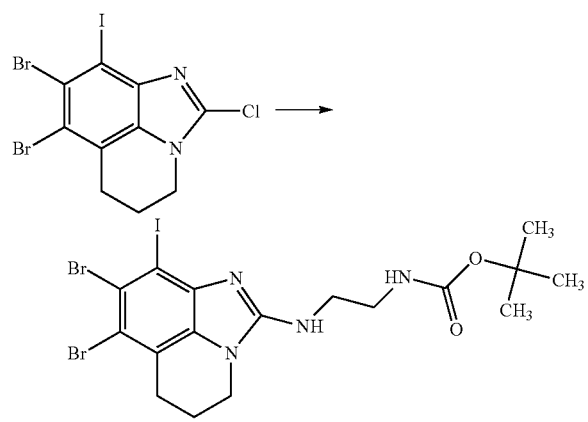

tert-butyl {2-[(7,8-dibromo-9-iodo-5,6-dihydro-4H-imidazo[4,5,1-ij]quinolin-2-yl)amino]ethyl}carbamate (Method 7A)

A 7,8-dibromo-2-chloro-9-iodo-5,6-dihydro-4H-imidazo[4,5,1-ij]quinoline (Method 6) (0.2 g, 0.4 mmol), boc-

3.10.8. Method 8

8-methyl-5,6-dihydro-4H-imidazo[4,5,1-ij]quinolin-2(1H)-one

To a solution of p-methyl tetrahydroquinoline (1 g, 6.8 mmol) in DMF (50 mL) potassium carbonate (3.7 g, 27.2 mmol) was added. The reaction mixture was cooled to 0° C. and methyl chloroformate was added dropwise. Then reaction mixture was stirred at 60° C. for 6 hrs. After cooled to the ambient temperature water was added and obtained solution was extracted with toluene/ethyl acetate 1:1. Combined organic phases were washed with 2M HCl, saturated NaHCO$_3$, brine, dried over anhydrous sodium sulfate and solvents were evaporated under reduced pressure. Obtained product (0.5 g, 2.4 mmol) was dissolved in acetic anhydride (15 mL) and solution was cooled to 0°. Then solution of HNO$_3$ (0.1 mL, 2.4 mmol) in acetic acid (1 mL) was added dropwise. After 10 minutes reaction was poured into saturated solution of NaHCO$_3$ and extracted with ethyl acetate. The organic phase was dried over sodium sulfate and solvent was concentrated under reduced pressure. The obtained product (0.8 g, 3.2 mmol) was dissolved in acetic acid and adds over 30 minutes to the suspension of iron (1.2 g, 22.4 mmol) in acetic acid heated to 70° C. Then reaction mixture was stirred at 80° C. over 2 hrs. After cooled to the ambient temperature ethyl acetate and Celite were added and stirred 30 minutes at room temperature. Then reaction mixture was filtered through Celite. To the filtrate 1M HCl was added and mixture was stirred at room temperature another 30 minutes. Next reaction mixture was extracted with ethyl acetate and separated organic phase was washed with water and brine, dried over sodium sulfate and concentrated under reduced pressure to gave 0.54 g of 8-methyl-5,6-dihydro-4H-imidazo[4,5,1-ij]quinolin-2(1H)-one as a white solid; yield 90%. LC-MS (m/z) 188.9 (M+1). $^1$H NMR (300 MHz, DMSO) δ 10.47 (s, 1H), 6.57 (s, 2H), 3.67-3.61 (m, 2H), 2.69 (t, J=6.0 Hz, 2H), 2.25 (s, 3H), 2.00-1.89 (m, 2H).

3.10.9. Method 9

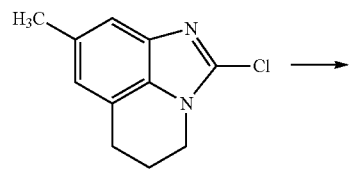

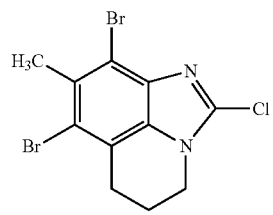

7,9-dibromo-2-chloro-8-methyl-5,6-dihydro-4H-imidazo[4,5,1-ij]quinoline

A 2-chloro-8-methyl-5,6-dihydro-4H-imidazo[4,5,1-ij]quinoline (0.2 g, 1 mmol) (Method 14D) was suspended in water and then bromine (0.2 mL, 3.8 mmol) was added. The reaction mixture was heated at 95° C. for 2 hrs. After cooled to the ambient temperature reaction mixture was quenched by saturated solution of sodium sulfite. The precipitated product—7,9-dibromo-2-chloro-8-methyl-5,6-dihydro-4H-imidazo[4,5,1-ij]quinoline (0.2 g) was collected by filtration, washed with water and air dried. LC-MS (m/z) 364.8 (M+1).

3.10.10. Method 10

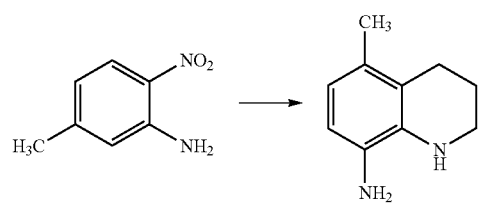

5-methyl-1,2,3,4-tetrahydroquinolin-8-amine

To the solution of 5-methyl-2-niroaniline (3.5 g, 23 mmol), glycerin (1.7 mL, 23 mmol) in nitrobenzene H$_2$SO$_4$ (5 mL) was added very slowly. The reaction mixture was heated at 80° C. for 16 hrs and then nitrobenzene was removed by steam distillation. Aqueous phase was alkalized by addition of NaHCO$_3$ and extracted with ethyl acetate. The organic phase was dried over sodium sulfate and solvent was concentrated under reduced pressure. The crude product was purified by column chromatography (silica gel, hexane/ethyl acetate 9:1). The obtained product (0.5 g, 2.7 mmol) was dissolved in acetic acid (10 mL) then PtO$_2$ (0.05 g, 0.27 mmol) was added. The reaction mixture was hydrogenated in Parr apparatus for 48 h. The acetic acid was removed in vacuum and resulting oil was dissolved in water, alkalized and extracted with ethyl acetate. Combined organic extracts were dried over magnesium sulfate and solvent was concentrated under reduced pressure. The 0.3 g of 5-methyl-1,2,3,4-tetrahydroquinolin-8-amine was obtained as a red oil; yield 75%. LC-MS (m/z) 162.9 (M+1).

3.10.11. Method 11

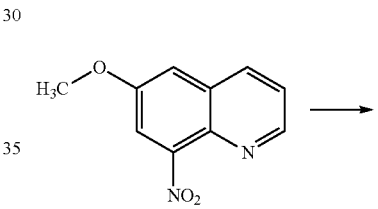

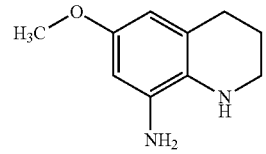

6-methoxy-1,2,3,4-tetrahydroquinolin-8-amine
(Method 11A)

A 6-methoxy-8-nitroquinoline (1 g, 4.9 mmol) was dissolved in acetic acid (10 mL) then PtO$_2$ (0.1 g, 0.5 mmol) was added. The reaction mixture was hydrogenated in Parr apparatus overnight. Then reaction mixture was filtered through Celite, washed by methanol and solvents were concentrated under reduced pressure. The 0.8 g of 6-methoxy-1,2,3,4-tetrahydroquinolin-8-amine was obtained as a red oil; yield 92%. LC-MS (m/z) 178.9 (M+1).

The following starting compounds were prepared by the procedure of Method 11A, using the appropriate starting material:

| Method | Product | ¹H NMR | m/z | RT [min] | Starting materials |
|---|---|---|---|---|---|
| 11B | 7-methyl-1,2,3,4-tetrahydroquinolin-8-amine | | 162.9 | 1.5 | 7-methyl-8-nitroquinoline (commercial) |
| 11C | 8-amino-1,2,3,4-tetrahydroquinoline | | 148.2 | | 8-aminoquinoline (commercial) |
| 11D | 2-methyl-1,2,3,4-tetrahydroquinolin-8-amine | | 162.9 | 1.6 | 2-methyl-8-nitroquinoline (commercial) |
| 11E | 5-bromo-1,2,3,4-tetrahydroquinolin-8-amine | | 227.1 | 2.9 | 8-amino-5-bromoquinoline (prepared by the method described in WO2010/30722 A1) |

3.10.12. Method 12

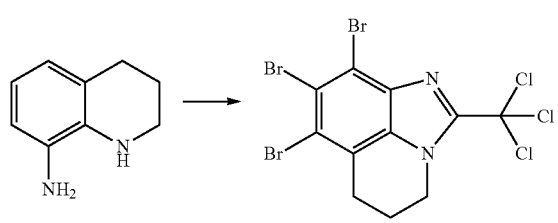 [SMILES: Nc1cccc2c1NCCC2 ; ClC(Cl)(Cl)c1nc2c(Br)c(Br)c(Br)c3c2n1CCC3]

2,2,2-trichloro-1-(7,8,9-tribromo-5,6-dihydro-4H-imidazo[4,5,1-ij]quinolin-2-yl)ethanone To a solution of 8-amino-1,2,3,4-tetrahydroquinoline (2.1 g, 14 mmol) (Method 11C) in acetic acid (25 mL) cooled to 0° C. methyl 2,2,2-trichloroacetimidate (2.6 mL, 21 mmol) was added dropwise. The reaction was allowed to reach ambient temperature and stirred overnight. Next solvent was removed under reduced pressure and the residue was washed with alkaline water. The crude (3.7 g, 13 mmol) was suspended in water (25 mL) and then bromine (2.8 mL, 54 mmol) was added. The reaction mixture was heated at 90° C. for 3 hrs. The reaction was quenched by saturated solution of sodium thiosulphate. The precipitated product was collected by filtration, dried and yellowish product was recrystallized from chloroform. LC-MS (m/z) 512.7 (M+1).

3.10.13. Method 13

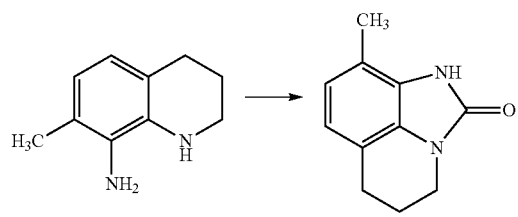

9-methyl-5,6-dihydro-4H-imidazo[4,5,1-ij]quinolin-2(1H)-one (Method 13A)

A mixture of 7-methyl-1,2,3,4-tetrahydroquinolin-8-amine (17 g, 74 mmol) (Method 11B), urea (7.6 g, 89 mmol) in xylene (500 mL) were heated at 150° C. for 48 hours. Then xylene was evaporated under reduced pressure. To the residue water (100 mL) was added and the mixture was stirred for 10 minutes. Product was extracted with dichloromethane. The extract was dried over anhydrous sodium sulfate, concentrated, and precipitated white product was collected by filtration. LC-MS (m/z) 188.9 (M+1).

The following starting compounds were prepared by the procedure of Method 13A, using the appropriate starting material:

| Method | Product | $^1$H NMR | m/z | RT [min] | Starting materials |
|---|---|---|---|---|---|
| 13B | 5,6-dihydro-4H-imidazo[4,5,1-ij]quinolin-2(1H)-one | | 174.2 | | 8-amino-1,2,3,4-tetrahydroquinoline Method 11C |
| 13C | 7-bromo-5,6-dihydro-4H-imidazo[4,5,1-ij]quinolin-2(1H)-one | | 174.2 | | 5-bromo-1,2,3,4-tetrahydroquinolin-8-amine Method 11E |
| 13D | 4-methyl-5,6-dihydro-4H-imidazo[4,5,1-ij]quinolin-2(1H)-one | | 188.2 | | 2-methyl-1,2,3,4-tetrahydroquinolin-8-amine Method 11D |

3.10.14. Method 14

2-chloro-5,6-dihydro-4H-imidazo[4,5,1-ij]quinoline (Method 14A)

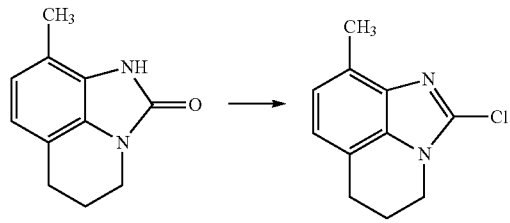

A 9-methyl-5,6-dihydro-4H-imidazo[4,5,1-ij]quinolin-2(1H)-one (20 g, 106 mmol) (Method 13A) was suspended in $POCl_3$ (500 mL) and heated at 105° C. overnight. The reaction mixture was cooled down to ambient temperature, poured into ice and alkalized with 20% NaOH. The water phase was extracted with dichloromethane, then combined organic layers were dried over anhydrous sodium sulfate and solvent was evaporated under reduced pressure. The crude product was purified by column chromatography (silica gel, dichloromethane/methanol 99:1) to give 11.7 g of 2-chloro-5,6-dihydro-4H-imidazo[4,5,1-ij]quinoline; yield 53%. LC-MS (m/z) 206.8 (M+1).

The following starting compounds were prepared by the procedure of Method 14A, using the appropriate starting material:

| Method | Product | ¹H NMR | m/z | RT [min] | Starting materials |
|---|---|---|---|---|---|
| 14B | 2-chloro-5,6-dihydro-4H-imidazo[4,5,1-ij]quinoline | | 192.8 | 2.4 | 5,6-dihydro-4H-imidazo[4,5,1-ij]quinolin-2(1H)-one Method 13B |
| 14C | 7-bromo-2-chloro-5,6-dihydro-4H-imidazo[4,5,1-ij]quinoline | | 271.5 | 3.0 | 7-bromo-5,6-dihydro-4H-imidazo[4,5,1-ij]quinolin-2(1H)-one Method 13C |
| 14D | 2-chloro-8-methyl-5,6-dihydro-4H-imidazo[4,5,1-ij]quinoline | | 206.9 | 2.7 | 8-methyl-5,6-dihydro-4H-imidazo[4,5,1-ij]quinolin-2(1H)-one Method 8 |
| 14E | 8-bromo-2-chloro-5,6-dihydro-4H-imidazo[4,5,1-ij]quinoline | | 272.7 | 3.1 | 8-bromo-5,6-dihydro-4H-imidazo[4,5,1-ij]quinolin-2(1H)-one (prepared by the method described in EP1719761) |

-continued

| Method | Product | ¹H NMR | m/z | RT [min] | Starting materials |
|---|---|---|---|---|---|
| 14F | 7,8-dibromo-2-chloro-5,6-dihydro-4H-imidazo[4,5,1-ij]quinoline 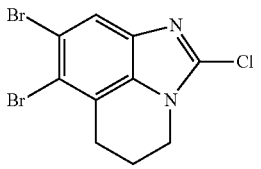 | ¹H NMR (600 MHz, DMSO) δ 7.89 (s, 1H), 4.46-3.97 (m, 2H), 2.91 (t, J = 6.0 Hz, 2H), 2.34-2.12 (m, 2H) | 350.8 | 3.5 | 7,8-dibromo-5,6-dihydro-4H-imidazo[4,5,1-ij]quinolin-2(1H)-one 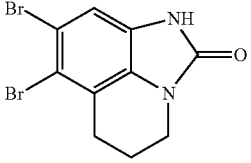<br>Method 3 |
| 14G | 2-chloro-4-methyl-5,6-dihydro-4H-imidazo[4,5,1-ij]quinoline 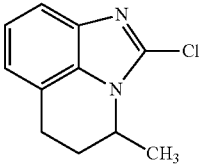 | | 206.8 | 2.7 | 4-methyl-5,6-dihydro-4H-imidazo[4,5,1-ij]quinolin-2(1H)-one 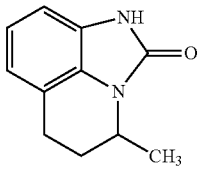<br>Method 13D |

3.11. Determination of Protein Kinase Inhibitory Activity

Representative compounds of formula (I) were screened for activity against CDK8, CDK9, CDK1, CDK2, CDK5 and CDK7 kinases in standard pharmacological test procedures. Based on the activity shown in the standard test procedures, the compounds of the present invention can be useful as potent and selective inhibitors of CDK8. Representative compounds according to claim 1 inhibited CDK8 kinase activity >50% when tested at 1 μM concentration in the kinase reaction as can be derived from Table 2 below.

Testing of the compounds described in this invention was carried out using the ADP-Glo™ Kinase Assay from Promega Corporation (Madison, Wis., USA). Percent inhibition at 1 μM concentration was determined for the compounds and pan-CDK inhibitor flavopyridol used as a positive control, and the results are shown in Table 2.

The ADP-Glo™ Kinase Assay is a luminescent ADP detection assay to measure kinase activity by quantifying the amount of ADP produced during a kinase reaction. The kinase assay is performed in kinase assay buffer (5 mM MOPS, pH 7.5, 5 mM $MgCl_2$, 0.4 mM EDTA, 1.5 mM DTT). Test samples initially dissolved in DMSO at 10 mM were diluted with the assay buffer to 1000 nM. A 30 μL volume/well of a mixture of substrates containing ATP (final ATP concentration in each kinase assay was equal to its apparent ATP Km).

CDK8/CyclinC (ProQinase, Freiburg, Germany) was used at the concentration 130 ng/well and MBP was used as a substrate at the concentration 10 μM (Millipore, Billerica, Mass., USA), determined Km ATP was 53 μM.

CDK9/CyclinT (Proqinase, Freiburg, Germany) was used at the concentration 100 ng/well and the peptide YSPTSPSYSPTSPSYSPTSPSKKKK (Lipopharm, Gdańsk, Poland) was used as a substrate at the concentration of 30 μM, determined Km ATP was 26 μM.

CDK1/CyclinB (Millipore, Billerica, Mass., USA) was used at concentration 40 ng/well and the peptide PKTPKKAKKL (Lipopharm, Gdańsk, Poland) was used as a substrate at the concentration of 80 μM, determined Km ATP was 20 μM.

CDK2/CyclinE (Millipore, Billerica, Mass., USA) was used at concentration 20 ng/well and the peptide PKTPKKAKKL (Lipopharm, Gdańsk, Poland) was used as a substrate at the concentration of 100 μM, determined Km ATP was 130 μM.

CDK5/p25 (Millipore, Billerica, Mass., USA) was used at concentration 30 ng/well and the peptide PKTPKKAKKL (Lipopharm, Gdansk, Poland) was used as a substrate at the concentration of 120 μM, determined Km ATP was 12 μM.

CDK7/CyclinH/MAT1 (Millipore, Billerica, Mass., USA) was used at concentration 40 ng/well and the peptide YSPTSPSYSPTSPSYSPTSPSKKKK (Lipopharm, Gdansk, Poland) was used as a substrate at the concentration of 30 μM, determined Km ATP was 130 μM.

The assay was performed in two steps: first, after the kinase reaction, an equal volume of ADP-Glo™ Reagent was added to terminate the kinase reaction and deplete the remaining ATP. Second, the Kinase Detection Reagent was added to simultaneously convert ADP to ATP and allowed the newly synthesized ATP to be measured using a luciferase/luciferin reaction. The luminescent signal generated was proportional to the ADP concentration produced and was correlated with kinase activity.

TABLE 2

Inhibition of kinase activity by representative compounds at 1 µM

% inhibition at 1 µM

| Example | CDK8/ CyclinC | CDK9/ CyclinT | CDK1/ CyclinB | CDK2/ CyclinE | CDK5/ p25 | CDK7/ CyclinH/ MAT1 |
|---|---|---|---|---|---|---|
| 6 | 96 | 55 | 38 | 0 | 39 | 21 |
| 1C | 52 | 9 | 0 | 8 | | |
| 3C | 59 | | | | | |
| 3B | 45 | | | | | |
| 3D | 87 | 20 | 2 | 0 | 0 | 11 |
| 3E | 64 | 3 | | 3 | | |
| 3F | 67 | | | | | |
| 3G | 80 | | | | | |
| 3J | 58 | 34 | 0 | 1 | 53 | 0 |
| 1K | 76 | 3 | 0 | 0 | 13 | 0 |
| 3I | 85 | 14 | 0 | 0 | 14 | 0 |
| 1N | 49 | | | | | |
| 1A | 52 | 33 | 0 | 0 | 0 | 0 |
| 1S | 54 | 4 | | | | |
| 3L | 54 | 6 | | | | |
| 1W | 100 | 13 | 7 | 0 | 2 | 0 |
| 1X | 71 | 9 | 15 | 8 | 27 | 0 |
| 1Y | 100 | 39 | 32 | 11 | 4 | 0 |
| 3M | 75 | 17 | 7 | 2 | 36 | 0 |
| 3N | 58 | 18 | | | | |
| 7E | 94 | 39 | 43 | 22 | 5 | 15 |
| 3A | 61 | 1 | 0 | 4 | 0 | 3 |
| 3P | 88 | 22 | 8 | 5 | 0 | 16 |
| 3R | 100 | 4 | 0 | 0 | 4 | 36 |
| 1AW | 57 | 41 | | 0 | | |
| 7B | 88 | 6 | | 14 | | |
| 3AL | 76 | 18 | | | | |
| 3AM | 100 | 39 | | 40 | | |
| 3AN | 85 | 21 | | 4 | | |
| 3AO | 93 | 22 | | 16 | | |
| 1E | 89 | 20 | | 2 | | |
| 3S | 89 | 16 | | 7 | | |
| 3T | 90 | 21 | | 17 | | |
| 1G | 96 | 45 | | 29 | | |
| 1H | 67 | 8 | | 0 | | |
| 1L | 81 | 9 | | 19 | | |
| 1M | 59 | 0 | | 6 | | |
| 3U | 92 | 24 | | 9 | | |
| 4A | 75 | 0 | | 8 | | |
| 3W | 92 | 10 | | 8 | | |
| 3X | 92 | 41 | | 9 | | |
| 8B | 90 | 20 | | 0 | | |
| 3Y | 69 | 17 | | 21 | | |
| 3AA | 96 | 21 | | 20 | | |
| 3AB | 84 | 47 | | 27 | | |
| 3AC | 94 | 26 | | 12 | | |
| 3AD | 100 | 42 | | 16 | | |
| 1AE | 97 | 61 | | 44 | | |
| 1AG | 82 | 42 | | 33 | | |
| 3AH | 76 | 0 | | 0 | | |
| 3AK | 75 | −9 | | 0 | | |
| 1AK | 93 | 2 | | 0 | | |
| 7A | 92 | 19 | 0 | 6 | 0 | 0 |
| 7C | 83 | 20 | 0 | 7 | 0 | 0 |
| 1AN | 61 | 10 | | | | |
| 3AP | 81 | 9 | | | | |
| 1AP | 65 | 15 | | | | |
| 1AU | 90 | 12 | | | | |
| 7D | 66 | | | | | |
| 1AX | 70 | 7 | 7 | 1 | | |
| 1AZ | 61 | | | | | |
| 3AR | 75 | | | | | |
| 3AT | 82 | | | | | |
| 3AU | 76 | | | | | |
| Flavopiridol | 93 | 93 | 100 | 68 | 50 | 76 |

3.12. Determination of Growth Inhibitory Activity Against CDK8 Expressing Cells by Cellular Proliferation Assay The viability of CDK8 expressing cells can be evaluated using a tetrazolium salt reduction cell-based assay. In viable cells this colorimetric assay can measure mitochondrial reduction of a tetrazolium component (MTS) into an insoluble formazan product. For MTS viability assay, human colon cancer cell lines were used (SW480 and HCT116 cell lines), containing elevated levels of CDK8 protein and highly dependent on its expression for proliferation [see, Firenstein et al. Nature 455 (25):547-551, (2008)]. These cell lines were used to determine the activity of the compounds provided herein to inhibit CDK8 in intact cells. Human tumor cell lines were obtained from ATCC (Rockville Md. USA). In each case, and by methods known to those practiced in the art of cell culture, vaiability was measured after 72 hour incubation with the compounds provided herein using a standard MTS protocol (CellTiter 96® AQ$_{ueous}$ Non-Radioactive Cell Proliferation Assay).

Briefly, cells were plated at 10,000-20,000 cells per well in DMEM medium supplemented with 10% fetal bovine serum. The compound plate was set up by aliquoting into column 1 of a 96-well plate, the negative control (DMSO), aliquoting into column 12 the positive control, and titrating the test compound in serial dilutions into columns 2-11. An aliquot from each well of the compound plate was transferred to the plated cells and then incubated at 37° C. in 5% $CO_2$. 20 µL of MTS tetrazolium was added to each well of optical plate and the cells were incubated at 37° C. in 5% $CO_2$ for 2 hours. The absorbance was measured at 490 nm using a microplate reader. Cell proliferation values are measured in terms of concentration of test compound that achieve 50% inhibition of cellular proliferation compared to control ($IC_{50}$) and are reported in Table 3.

TABLE 3

Growth inhibitory activity ($IC_{50}$ in µM) on colon cancer cells HCT116 and SW480:

| | IC50 [µM] | |
|---|---|---|
| Example | HCT116 ED50 | SW-480 ED50 |
| 6 | 0.4 | 1.0 |
| 1B | 1.3 | 0.5 |
| 1I | 1.5 | |
| 1J | 0.5 | |
| 1K | 0.7 | 1.1 |
| 3I | 6.8 | 5.0 |
| 3K | 2.2 | |
| 1N | 4.3 | |
| 1A | 1.2 | 1.9 |
| 1O | 1.3 | |
| 1P | 1.4 | |
| 1S | 1.7 | 2.5 |
| 1U | 1.6 | |
| 1X | 6.7 | 1.4 |
| 1Y | 1.3 | 0.7 |
| 3M | 1.2 | 2.3 |
| 7E | 0.3 | 0.6 |
| 3P | 9.3 | 1.4 |
| 7B | 2.6 | 6.3 |
| 3AM | 2.8 | 4.0 |
| 1E | 1.9 | 2.7 |
| 3T | 1.6 | 1.3 |
| 1G | 0.7 | 1.1 |
| 1L | 1.1 | 1.4 |
| 1M | 1.1 | 1.5 |
| 3W | 1.5 | 1.4 |
| 8B | 1.7 | 4.1 |

TABLE 3-continued

Growth inhibitory activity (IC$_{50}$ in μM) on colon cancer cells HCT116 and SW480:

| | IC50 [μM] | |
|---|---|---|
| Example | HCT116 ED50 | SW-480 ED50 |
| 3AA | 0.4 | 1.3 |
| 3AB | 0.4 | 1.4 |
| 3AD | 0.6 | 1.3 |
| 1AE | 0.3 | 1.1 |
| 1AF | 1.3 | 1.8 |
| 1AG | 1.3 | 0.5 |
| 1AK | 1.7 | 1.8 |
| 7A | 1.3 | 1.3 |
| 7C | 1.1 | 0.9 |
| 1AL | 5.3 | 1.8 |
| 1AN | 2.4 | |
| 1AU | 0.2 | 1.1 |
| 1AX | 1.5 | |
| 1AZ | 1.6 | |

Similar results were obtained in other cancer cell lines as well. Thus, the compounds "Example 6" and "Example 1K" showed cytotoxic effects in A549 lung carcinoma, HepG2 hepatocarcinoma, MCF7 breast adenocarcinoma, MV4-11 acute myelocytic leukemia (AML), Rec-1 B-cell lymphoma, SK-MEL5 melanoma and PC-3 adenocarcinoma prostate cell lines.

These assays establish that compounds according to the present invention are effective in inhibiting CDK8 kinase and inhibiting oncogenic cell growth.

3.13. Determination of In Vivo Activity Against Xenograft Tumors Expressing CDK8 Implanted in Immunosuppressed Animals The substituted Tricyclic Benzimidazoles of the present invention are useful as anti-cancer agents due to their ability to reduce tumor growth in vivo in mammals. Various well-accepted animal models exist for cancer. By way of example, antitumor activity can be evaluated in vivo in murine xenograft models. Briefly, female mice, NOD/SCID, 5-6 weeks old, were used for the study. On the 1st experimental day, 5*10$^6$ HCT116 cells were suspended in 0.1 ml 0.9% NaCl+Matrigel® (BD Biosciences) (1:1, v:v) and were injected subcutaneously, on the right side just above the groin. As the tumor growth was progressing, the tumor size was measured every day, and the tumor volume was computed from the formula: TV=(a*a*b)/2 in mm3, where a is the short axis in mm, and b is the long axis in mm. When the average tumor volume reached and exceeded 100 mm3, mice were randomized into uniform groups and subjected to the compound administrations. The administration of the compound was performed and continued according to the experimental schedule.

The tumor volume was monitored throughout the study and the tumor growth inhibition (TGI) was computed using the following formula: TGI [%]=((Av Norm TGC−Av Norm TGT)/Av Norm TGC)×100, where Av Norm TGC is the mean (average) normalized tumor growth of the control group, and Av Norm TGT is the mean (average) normalized tumor growth of the treated group. Norm TG was computed using the formula: Norm TG=Norm TV−100, where Norm TV is the normalized tumor volume. Normalized tumor volume was computed using the formula: Norm TV= (TVDn/TVD1)*100, where TVDn is the tumor volume on the day of tumor measurement, and TVD1 is the tumor volume on the first day of compound administration. Thus, for instance at an orally administered dose of 30 mg/kg, the present compounds elicit the percent of inhibition in mice shown below. TGI Changes in tumor volume in animals treated with substituted tricyclic benzimidazoles and control, vehicle treated animals are reported in the FIG. 1.

This assay establishes that the compounds according to the present invention are capable of inhibiting oncogenic tumor growth in vivo.

3.14. Synergistic and Additive Interactions with Anti-Cancer Agents

Various reports indicated usefulness of strategies based on the inhibition of CDK8 in combination with other drugs. [MacKeigan et al. Nat Cell Biol. 7(6):591-600, (2005); Porter et al., PNAS (34) 109: 13799-13804, (2012)].

Various well-accepted models exist for determination of synergistic and additive effect for two or more drugs in combination. As a matter of example combination index CI can be used as a quantitative measure of the degree of drug interaction in terms of synergism, additive effects and antagonism for a given endpoint of the measurement:
Synergism (C<1) greater than expected additive effect
Additive effect (CI=1) the combined effect predicted by the mass-action law principle in the absence of synergism or antagonism
Antagonism (CI>1) Smaller than expected additive effect In the present example, the drug interactions between compound "Example 6" and Oxaliplatin which is a platinum-based type of anticancer chemotherapy medicine used to treat colorectal cancer were tested in HCT116 cells. Experimental data points in the MTS cell viability assay were spread for Oxaliplatin below and above the ED50 values in HCT116 cells, whereas concentration of the tested compounds was close to the apparent ED50. Chou-Thalay method for quantification of synergy was applied [Chou et al. Cancer Res. 15; 70(2):440-6, (2010)].

Figure 2:
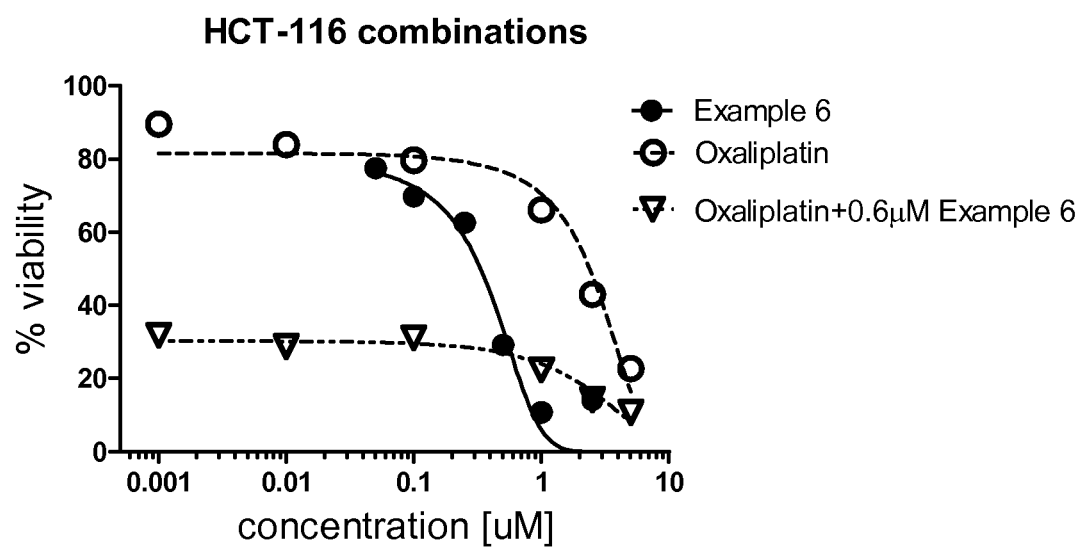
FIG. 2: Viability of HCT116 cells treated with the compound "Example 6", Oxaliplatin or a combination thereof.

The results are depicted in FIG. 2.

TABLE 5

Synergy of the Example 6 and Oxaliplatin in HCT116 cells

| Example 6 (μM) | Oxaliplatin (μM) | % viability | Combination Index (CI) |
|---|---|---|---|
| 0.6 | 0.0010 | 0.32 | 1.15 |
| 0.6 | 0.01 | 0.29 | 0.99 |
| 0.6 | 0.1 | 0.31 | 1.11 |
| 0.6 | 1.0 | 0.22 | 0.69 |
| 0.6 | 2.5 | 0.14 | 0.38 |
| 0.6 | 5.0 | 0.11 | 0.29 |

3.16 Inhibition of Pro-Inflammatory Cytokines

Autoimmune diseases arise from an inappropriate immune response of the body against substances and tissues normally present in the body. This may be restricted to certain organs or may involve a particular tissue in different places. The treatment of autoimmune diseases is typically achieved with immunosuppression—medication which decreases the immune response. In inflammatory diseases, it is the overreaction of the immune system, and its subsequent downstream signaling (TNF, I1-6, etc.), which causes problems. Mitigation of inflammation by activation of anti-inflammatory genes and the suppression of inflammatory genes such as cytokines in immune cells is a promising way of novel therapies.

The LPS assay was used to evaluate ability to respond to an inflammatory stimulus by mounting an acute phase response. The acute phase response is characterized by a dramatic increase in the production of a group of proteins by the liver. Bacterial LPS is an endotoxin, a potent inducer of the acute phase response and systemic inflammation. This response is induced by the production of TNFα, IL-1β, and IL-6 from activated monocytes and neutrophils in response to inflammatory stimuli. Evaluation of the three pro-inflammatory cytokines, TNFα, IL-1β, and IL-6, is the current standard method for evaluation of the ability of the immune system to mount an innate inflammatory immune response. In each case, and by methods known to those practiced in the art, RAW 264.7 Mouse leukaemic monocyte macrophage cells were plated at the density of 40 000 cells per well. Next day, cells were pre-incubated with tested compounds (fconc=10 μM) for 4 h and then stimulated with LPS (fconc=1 μg/ml) for 6 h. In the cell culture media IL-6 and TNFα levels were examined by ELISA using BD OptEIA™ Mouse IL-6 ELISA Set Cat. No 555240 and BD OptEIA™ Mouse TNFα ELISA Set Cat. No 555268 (BD Biosciences Pharmingen, SanDiego, Calif., USA), according to manufacturer's instructions.

Figure 3:
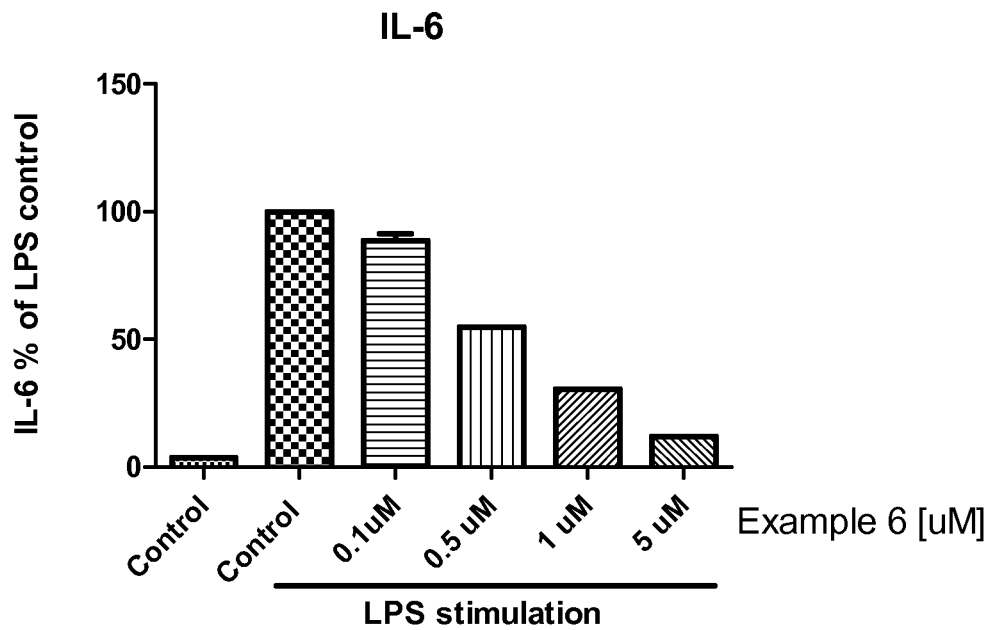
FIG. 3: LPS-induced levels of IL6 and TNFalpha and dose dependent reduction in cytokine IL6 and TNFalpha production by compound "Example 6"-treatment in RAW 264.7.
Figure 3:
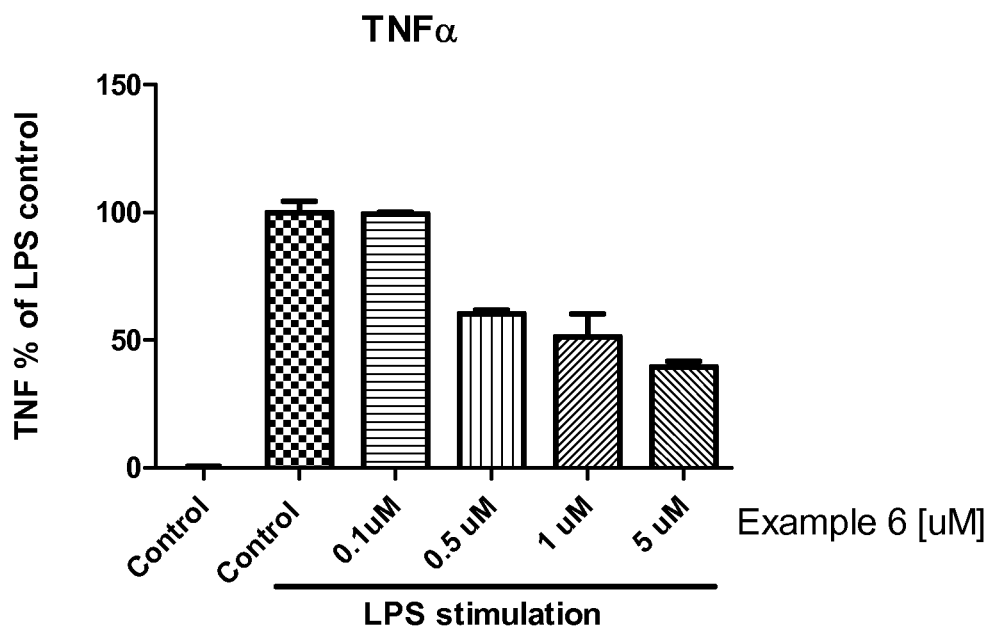

The results shown in FIG. 3 indicate that strong CDK8 inhibitors such as the compound "Example 6" could repress production of pro-inflammatory cytokines

3.17. Regulation of Cell Migration

Cell migration that occurs in response to chemical signals is important in many different functions including wound repair, cell differentiation, embryonic development and as a key event in metastasis of tumors. Cell invasion requires a cell to migrate through an extracellular matrix or basement membrane extract which first has to be enzymatically degraded.

Figure 4:
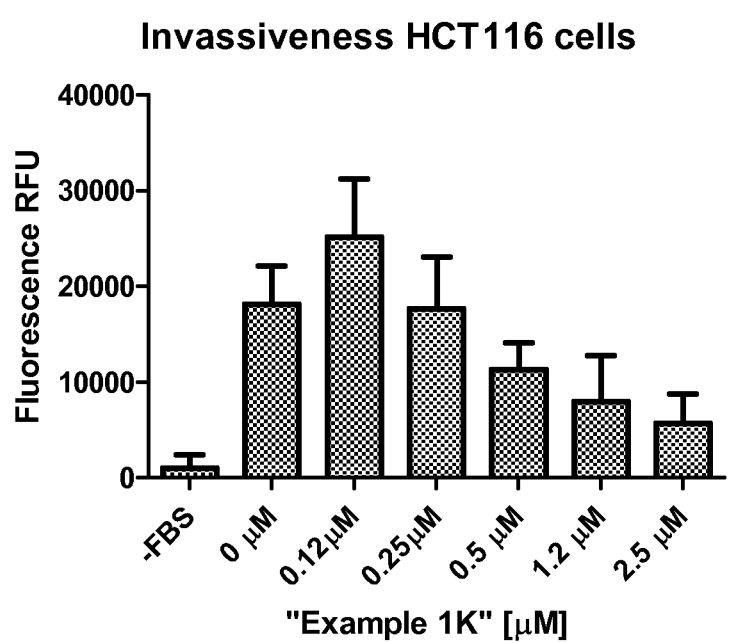
FIG. 4: Repression of the invasiveness of HCT116 cells by compound "Example 1K" present in increasing concentrations in assays carried out in Matrigel Invasion Chambers.

Matrigel Invasion Chambers [catalog number 354480 (BD Biosciences)] are useful to study cell invasion of malignant and normal cells. Matrigel Invasion Chambers can be used to study the mechanisms of invasion and to identify factors that interfere with this process in an in vitro environment. According to standard assays known to the skilled person, $5 \times 10^4$ HCT116 cells/ml were added in each case to the upper chamber of the Matrigel Invasion Chambers in the presence of increasing concentrations of "Example 1K", whereas chemoatractant comprising 10% FBS was added to the lower chamber. The Invasion Chambers were incubated for 22 h in a humidified tissue culture incubator at 37° C., 5% $CO_2$. Non-invading cells were removed by scrubing. The cells on the lower surface of the membrane were then stained with Diff-Quik™ stain. The results shown in FIG. 4 indicate that strong and selective CDK8 inhibitors as the "Example 1K" compound appear to be capable of repressing invasiveness of HCT116 colon cancer cells.

Preferred embodiments of the present invention relate to:
1. A compound of formula (I)

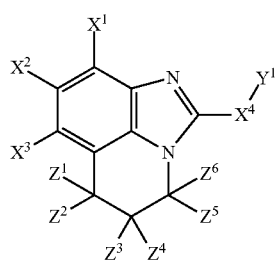

(I)

wherein
$X^1$, $X^2$ and $X^3$ are each independently selected from the group consisting of H, F, Cl, Br, I, —$OT^1$, —$N(T^2)(T^3)$, —NHC(=O)$T^4$, nitro, cyano, cyclopropyl and —$C_{1-3}$alkyl, with the proviso that at least two substituents selected from $X^1$, $X^2$ and $X^3$ are not H;
$Z^1$ and $Z^2$ are either taken together to form an oxo group at the carbon atom to which they are attached; or $Z^1$ and $Z^2$ are each independently selected from the group consisting of H, —$C_{1-6}$alkyl, —$OT^1$ and —$N(T^2)(T^3)$;
$Z^3$ and $Z^4$ are either taken together to form an oxo group at the carbon atom to which they are attached; or $Z^3$ and $Z^4$ are each independently selected from the group consisting of H, —$C_{1-6}$alkyl, —$OT^1$ and —$N(T^2)(T^3)$;
$Z^5$ and $Z^6$ are either taken together to form an oxo group at the carbon atom to which they are attached; or $Z^5$ and $Z^6$ are each independently selected from the group consisting of H, —$C_{1-6}$alkyl, —$OT^1$ and —$N(T^2)(T^3)$;
$X^4$ is either absent or selected from the group consisting of —$NR^4$—, —$N(R^4)(CH_2)$—, —C(=O)NH— and —C(=O)—;
$R^4$ is selected from H and —$C_{1-6}$alkyl;
$Y^1$ is selected from the group consisting of H, —$C_{1-6}$alkyl and a 4- to 7-membered saturated or unsaturated aromatic carbocycle or heterocycle, with the proviso that the point of attachment on said heterocycle is carbon if $X^4$ is —$NR^4$— or —C(=O)NH—, wherein said —$C_{1-6}$alkyl is optionally substituted with one or more substituents independently selected from —$OT^1$, —$ST^1$, —$N(T^2)(T^3)$ and a 5- to 6-membered saturated heterocycle, and wherein said 4- to 7-membered saturated or unsaturated aromatic carbocycle or heterocycle is optionally substituted with one or more substituents independently selected from F, Cl, Br, I, —C(=O)H, —$OT^1$, —$N(T^2)(T^3)$, —C(=O)$N(T^2)(T^3)$, —C(=O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$;
$T^1$, $T^2$ and $T^3$ are each independently selected from H and —$C_{1-6}$alkyl optionally substituted with one or more substituents independently selected from —$N(T^5)(T^6)$, —$OT^7$, —$ST^7$, nitro, cyano, —C(=O)$OT^7$, —C(=O)$N(T^5)(T^6)$, —OC(=O)$N(T^5)(T^6)$, —$S(=O)_2T^7$, —$S(=O)_2OT^8$ and —$S(=O)_2N(T^5)(T^6)$;
$T^4$ is —$C_{1-6}$alkyl optionally substituted with one or more substituents independently selected from —$N(T^5)(T^6)$, —$OT^7$, —$ST^7$, nitro, cyano, —C(=O)$OT^7$, —C(=O)$N(T^5)(T^6)$, —OC(=O)$N(T^5)(T^6)$, —$S(=O)_2T^8$, —$S(=O)_2OT^7$ and —$S(=O)_2N(T^5)(T^6)$;
$T^5$, $T^6$ and $T^7$ are each independently selected from H and —$C_{1-6}$alkyl optionally substituted with one or more substituents independently selected from amino, hydroxyl, thiol, nitro and cyano; and
$T^8$ is selected from —$C_{1-6}$alkyl optionally substituted with one or more substituents independently selected from amino, hydroxyl, thiol, nitro and cyano;
or a pharmaceutically acceptable salt thereof.
2. A compound according to 1, wherein at least two substituents selected from $X^1$, $X^2$ and $X^3$ are each independently selected from the group consisting of F, Cl, Br and I.

3. A compound according to 1 or 2, wherein $Y^1$ is a 4- to 7-membered saturated or unsaturated aromatic carbocycle or heterocycle, with the proviso that the point of attachment on said heterocycle is carbon if $X^4$ is —$NR^4$— or —C(=O)NH—, wherein said 4- to 7-membered saturated or unsaturated aromatic carbocycle or heterocycle is optionally substituted with one or more substituents independently selected from F, Cl, Br, I, —C(=O)H, —$OT^1$, —$N(T^2)(T^3)$, —C(=O)N$(T^2)(T^3)$, —C(=O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$;

4. A compound according to 1 or 2, wherein $X^4$ is —$NR^4$— and $Y^1$ is selected from H and —$C_{1-6}$alkyl, wherein said —$C_{1-6}$alkyl is optionally substituted with one or more substituents independently selected from —$OT^1$, —$ST^1$, —$N(T^2)(T^3)$ and a 5- to 6-membered saturated heterocycle.

5. A compound according to 1 or 2, wherein $X^4$ is —$NR^4$— and $Y^1$ is a 4- to 6-membered saturated or unsaturated aromatic carbocycle or heterocycle, wherein said 4- to 6-membered saturated or unsaturated aromatic carbocycle or heterocycle is optionally substituted with one or more substituents independently selected from F, Cl, Br, I, —C(=O)H, —$OT^1$, —$N(T^2)(T^3)$, —C(=O)$N(T^2)(T^3)$, —C(=O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$.

6. A compound according to 1 or 2, wherein $X^4$ is absent and $Y^1$ is a 4- to 7-membered saturated heterocycle, wherein said 4- to 7-membered saturated heterocycle is optionally substituted with one or more substituents independently selected from F, Cl, Br, I, —C(=O)H, —$OT^1$, —$N(T^2)(T^3)$, —C(=O)$N(T^2)(T^3)$, —C(=O)$OT^1$, —$ST^1$ and —$C_{1-3}$alkyl, wherein said —$C_{1-3}$alkyl is optionally substituted with one or more substituents independently selected from —$OT^1$ and —$N(T^2)(T^3)$.

7. A compound according to 1, wherein said compound is selected from the group consisting of:

(1R,2R)—N-(7,8,9-tribromo-5,6-dihydro-4H-imidazo[4,5,1-ij]quinolin-2-yl)cyclohexane-1,2-diamine hydrochloride
N-(7,8,9-tribromo-5,6-dihydro-4H-imidazo[4,5,1-ij]quinolin-2-yl)propane-1,3-diamine hydrochloride
1-amino-3-[(7,8,9-tribromo-5,6-dihydro-4H-imidazo[4,5,1-ij]quinolin-2-yl)amino]propan-2-ol hydrochloride
7,8,9-tribromo-2-(2-methylpiperazin-1-yl)-5,6-dihydro-4H-imidazo[4,5,1-ij]quinoline hydrochloride
7,8,9-tribromo-N-(pyrrolidin-2-ylmethyl)-5,6-dihydro-4H-imidazo[4,5,1-ij]quinolin-2-amine hydrochloride
(3S)-1-(7,8,9-tribromo-5,6-dihydro-4H-imidazo[4,5,1-ij]quinolin-2-yl)pyrrolidin-3-amine hydrochloride
1-[1-(7,8,9-tribromo-5,6-dihydro-4H-imidazo[4,5,1-ij]quinolin-2-yl)pyrrolidin-2-yl]methanamine hydrochloride
1-(7,8,9-tribromo-5,6-dihydro-4H-imidazo[4,5,1-ij]quinolin-2-yl)piperidin-3-amine hydrochloride
7,8,9-tribromo-N-(piperidin-4-yl)-5,6-dihydro-4H-imidazo[4,5,1-ij]quinolin-2-amine hydrochloride
7,8-dibromo-9-methyl-2-(piperazin-1-yl)-5,6-dihydro-4H-imidazo[4,5,1-ij]quinoline hydrochloride
7,8,9-tribromo-N-(pyrrolidin-3-yl)-5,6-dihydro-4H-imidazo[4,5,1-ij]quinolin-2-amine hydrochloride
1-(7,8,9-tribromo-5,6-dihydro-4H-imidazo[4,5,1-ij]quinolin-2-yl)azepan-4-amine hydrochloride
7,8-dibromo-2-(piperazin-1-yl)-5,6-dihydro-4H-imidazo[4,5,1-ij]quinoline hydrochloride
N-(7,8-dibromo-9-methyl-5,6-dihydro-4H-imidazo[4,5,1-ij]quinolin-2-yl)ethane-1,2-diamine hydrochloride
N-(7,9-dibromo-8-methyl-5,6-dihydro-4H-imidazo[4,5,1-ij]quinolin-2-yl)ethane-1,2-diamine hydrochloride
2-[(7,8,9-tribromo-5,6-dihydro-4H-imidazo[4,5,1-ij]quinolin-2-yl)sulfanyl]ethanamine hydrochloride
8,9-dibromo-7-methyl-2-(piperazin-1-yl)-5,6-dihydro-4H-imidazo[4,5,1-ij]quinoline hydrochloride
N-(8,9-dibromo-7-methyl-5,6-dihydro-4H-imidazo[4,5,1-ij]quinolin-2-yl)ethane-1,2-diamine hydrochloride
N-(7,8-dibromo-9-nitro-5,6-dihydro-4H-imidazo[4,5,1-ij]quinolin-2-yl)ethane-1,2-diamine hydrochloride
N-(7,8-dibromo-9-iodo-5,6-dihydro-4H-imidazo[4,5,1-ij]quinolin-2-yl) ethane-1,2-diamine hydrochloride
7,8-dibromo-9-nitro-2-(piperazin-1-yl)-5,6-dihydro-4H-imidazo[4,5,1-ij]quinoline hydrochloride
7,8-dibromo-9-iodo-2-(piperazin-1-yl)-5,6-dihydro-4H-imidazo[4,5,1-]quinoline hydrochloride
7,8-dibromo-2-(piperazin-1-yl)-5,6-dihydro-4H-imidazo[4,5,1-ij]quinolin-9-amine hydrochloride
N2-(2-aminoethyl)-7,8-dibromo-5,6-dihydro-4H-imidazo[4,5,1-ij]quinoline-2,9-diamine hydrochloride
N-(7,8-dibromo-5,6-dihydro-4H-imidazo[4,5,1-ij]quinolin-2-yl)ethane-1,2-diamine hydrochloride
N-(7,8-dibromo-5,6-dihydro-4H-imidazo[4,5,1-ij]quinolin-2-yl)propane-1,3-diamine hydrochloride
1-[1-(7,8,9-tribromo-5,6-dihydro-4H-imidazo[4,5,1-ij]quinolin-2-yl)piperidin-4-yl]methanamine hydrochloride
(3S)-1-(7,8,9-tribromo-5,6-dihydro-4H-imidazo[4,5,1-ij]quinolin-2-yl)pyrrolidin-3-amine hydrochloride
1-[4-(7,8,9-tribromo-5,6-dihydro-4H-imidazo[4,5,1-ij]quinolin-2-yl)morpholin-2-yl]methanamine hydrochloride
1-(7,8,9-tribromo-5,6-dihydro-4H-imidazo[4,5,1-ij]quinolin-2-yl)piperidin-4-amine hydrochloride
7,8,9-tribromo-N-[3-(piperazin-1-yl)propyl]-5,6-dihydro-4H-imidazo[4,5,1-ij]quinolin-2-amine hydrochloride
1-[4-(7,8-dibromo-9-methyl-5,6-dihydro-4H-imidazo[4,5,1-ij]quinolin-2-yl)morpholin-2-yl]methanamine hydrochloride
7,8,9-tribromo-N-[2-(piperazin-1-yl)ethyl]-5,6-dihydro-4H-imidazo[4,5,1-ij]quinolin-2-amine hydrochloride
(3R)-1-(7,8-dibromo-9-methyl-5,6-dihydro-4H-imidazo[4,5,1-ij]quinolin-2-yl)pyrrolidin-3-amine hydrochloride
7,8-dibromo-9-methyl-N-[(3S)-pyrrolidin-3-yl]-5,6-dihydro-4H-imidazo[4,5,1-ij]quinolin-2-amine hydrochloride
7,8-dibromo-9-methyl-N-[(3R)-pyrrolidin-3-yl]-5,6-dihydro-4H-imidazo[4,5,1-ij]quinolin-2-amine hydrochloride
7,9-dibromo-8-methoxy-2-(piperazin-1-yl)-5,6-dihydro-4H-imidazo[4,5,1-ij]quinoline hydrochloride
7,8,9-tribromo-N-[(3S)-pyrrolidin-3-yl]-5,6-dihydro-4H-imidazo[4,5,1-ij]quinolin-2-amine hydrochloride
1-(7,8-dibromo-9-methyl-5,6-dihydro-4H-imidazo[4,5,1-ij]quinolin-2-yl)piperidin-4-amine hydrochloride
1-[1-(7,8-dibromo-9-methyl-5,6-dihydro-4H-imidazo[4,5,1-ij]quinolin-2-yl)piperidin-4-yl]methanamine hydrochloride
trans-N-(7,8-dibromo-9-methyl-5,6-dihydro-4H-imidazo[4,5,1-ij]quinolin-2-yl)cyclohexane-1,4-diamine hydrochloride
(3S)-1-(7,8-dibromo-9-methyl-5,6-dihydro-4H-imidazo[4,5,1-ij]quinolin-2-yl)pyrrolidin-3-amine hydrochloride
7,8,9-tribromo-4-methyl-2-(piperazin-1-yl)-5,6-dihydro-4H-imidazo[4,5,1-ij]quinoline hydrochloride 7,8,9-tribromo-N-[(3S)-piperidin-3-yl]-5,6-dihydro-4H-imidazo[4,5,1-ij]quinolin-2-amine
7,9-dibromo-8-methyl-2-(piperazin-1-yl)-5,6-dihydro-4H-imidazo[4,5,1-ij]quinoline hydrochloride
7,8-dibromo-9-methyl-N-[(3R)-piperidin-3-yl]-5,6-dihydro-4H-imidazo[4,5,1-ij]quinolin-2-amine hydrochloride
7,8-dibromo-2-(1,4-diazepan-1-yl)-9-methyl-5,6-dihydro-4H-imidazo[4,5,1-ij]quinoline hydrochloride
7,8-dibromo-9-cyclopropyl-2-(piperazin-1-yl)-5,6-dihydro-4H-imidazo[4,5,1-ij]quinoline hydrochloride
N-(azetidin-3-yl)-7,8-dibromo-9-methyl-5,6-dihydro-4H-imidazo[4,5,1-ij]quinolin-2-amine hydrochloride
7,8-dibromo-9-methyl-N-(morpholin-2-ylmethyl)-5,6-dihydro-4H-imidazo[4,5,1-ij]quinolin-2-amine hydrochloride
1-(7,8-dibromo-9-methyl-5,6-dihydro-4H-imidazo[4,5,1-ij]quinolin-2-yl)azetidin-3-amine hydrochloride
(3S)-1-(7,8-dibromo-9-methyl-5,6-dihydro-4H-imidazo[4,5,1-ij]quinolin-2-yl)pyrrolidin-3-amine hydrochloride
(3R)-1-(7,8-dibromo-9-methyl-5,6-dihydro-4H-imidazo[4,5,1-ij]quinolin-2-yl)piperidin-3-amine hydrochloride
(3S)-1-(7,8-dibromo-9-methyl-5,6-dihydro-4H-imidazo[4,5,1-ij]quinolin-2-yl)piperidin-3-amine hydrochloride
N-(7,8,9-tribromo-5,6-dihydro-4H-imidazo[4,5,1-ij]quinolin-2-yl)ethane-1,2-diamine hydrochloride
7,8,9-tribromo-N-[2-(morpholin-4-yl)ethyl]-5,6-dihydro-4H-imidazo[4,5,1-ij]quinolin-2-amine hydrochloride
7,8,9-tribromo-N-[2-(pyrrolidin-1-yl)ethyl]-5,6-dihydro-4H-imidazo[4,5,1-ij]quinolin-2-amine hydrochloride
(1R,2R)—N,N'-dimethyl-N-(7,8,9-tribromo-5,6-dihydro-4H-imidazo[4,5,1-ij]quinolin-2-yl)cyclohexane-1,2-diamine hydrochloride
1-(7,8,9-tribromo-5,6-dihydro-4H-imidazo[4,5,1-ij]quinolin-2-yl)piperidin-4-ol
7,8,9-tribromo-N-(pyridin-4-yl)-5,6-dihydro-4H-imidazo[4,5,1-ij]quinolin-2-amine
7,8,9-tribromo-N-phenyl-5,6-dihydro-4H-imidazo[4,5,1-ij]quinolin-2-amine
7,8,9-tribromo-2-(piperidin-1-yl)-5,6-dihydro-4H-imidazo[4,5,1-ij]quinoline
7,8,9-tribromo-N-cyclohexyl-5,6-dihydro-4H-imidazo[4,5,1-ij]quinolin-2-amine
3-[(7,8,9-tribromo-5,6-dihydro-4H-imidazo[4,5,1-ij]quinolin-2-yl)amino]propan-1-ol
7,8,9-tribromo-2-(morpholin-4-yl)-5,6-dihydro-4H-imidazo[4,5,1-ij]quinoline
N-(7,8,9-tribromo-5,6-dihydro-4H-imidazo[4,5,1-ij]quinolin-2-yl)butane-1,4-diamine
7,8,9-tribromo-N,N-diethyl-5,6-dihydro-4H-imidazo[4,5,1-ij]quinolin-2-amine
7,8,9-tribromo-5,6-dihydro-4H-imidazo[4,5,1-ij]quinolin-2-amine
N,N-dimethyl-N'-(7,8,9-tribromo-5,6-dihydro-4H-imidazo[4,5,1-ij]quinolin-2-yl)ethane-1,2-diamine
7,8,9-tribromo-N-[3-(pyrrolidin-1-yl)propyl]-5,6-dihydro-4H-imidazo[4,5,1-ij]quinolin-2-amine
7,8,9-tribromo-2-(4-methylpiperazin-1-yl)-5,6-dihydro-4H-imidazo[4,5,1-ij]quinoline
7,8,9-tribromo-2-(3,3-dimethylpiperazin-1-yl)-5,6-dihydro-4H-imidazo[4,5,1-ij]quinoline
1-(7,8,9-tribromo-5,6-dihydro-4H-imidazo[4,5,1-ij]quinolin-2-yl)piperidin-3-ol
7,8,9-tribromo-2-(3-methylpiperazin-1-yl)-5,6-dihydro-4H-imidazo[4,5,1-ij]quinoline
7,8,9-tribromo-2-(2-methylpyrrolidin-1-yl)-5,6-dihydro-4H-imidazo[4,5,1-ij]quinoline
7,8-dibromo-9-iodo-2-(2-methylpyrrolidin-1-yl)-5,6-dihydro-4H-imidazo[4,5,1-ij]quinoline
7,8-dibromo-9-iodo-2-[(3R)-3-methylpiperazin-1-yl]-5,6-dihydro-4H-imidazo[4,5,1-ij]quinoline
[1-(7,8,9-tribromo-5,6-dihydro-4H-imidazo[4,5,1-ij]quinolin-2-yl)piperidin-3-yl]methanol
7,8-dibromo-2-(3,3-dimethylpiperazin-1-yl)-9-iodo-5,6-dihydro-4H-imidazo[4,5,1-ij]quinoline
7,8-dibromo-N,N-diethyl-9-iodo-5,6-dihydro-4H-imidazo[4,5,1-ij]quinolin-2-amine
7,8-dibromo-9-iodo-5,6-dihydro-4H-imidazo[4,5,1-ij]quinolin-2-amine
7,8,9-tribromo-N-(tetrahydro-2H-pyran-4-yl)-5,6-dihydro-4H-imidazo[4,5,1-ij]quinolin-2-amine
7,8,9-tribromo-2-[(3S)-3-methylpiperazin-1-yl]-5,6-dihydro-4H-imidazo[4,5,1-ij]quinoline
7,8,9-tribromo-2-[(3R)-3-methylpiperazin-1-yl]-5,6-dihydro-4H-imidazo[4,5,1-ij]quinoline
(3R)-1-(7,8,9-tribromo-5,6-dihydro-4H-imidazo[4,5,1-ij]quinolin-2-yl)pyrrolidin-3-ol
7,8-dibromo-9-iodo-2-[(3R)-3-methylpiperazin-1-yl]-5,6-dihydro-4H-imidazo[4,5,1-ij]quinoline
7,8-dibromo-9-methyl-2-(2-methylpyrrolidin-1-yl)-5,6-dihydro-4H-imidazo[4,5,1-ij]quinoline
7,8,9-tribromo-N-[2-(4-methylpiperazin-1-yl)ethyl]-5,6-dihydro-4H-imidazo[4,5,1-ij]quinolin-2-amine
7,8-dibromo-2-[(3R,5S)-3,5-dimethylpiperazin-1-yl]-9-methyl-5,6-dihydro-4H-imidazo[4,5,1-ij]quinoline
7,8-dibromo-9-methyl-2-(3-methylpiperazin-1-yl)-5,6-dihydro-4H-imidazo[4,5,1-ij]quinoline
7,8-dibromo-2-(3,3-dimethylpiperazin-1-yl)-9-methyl-5,6-dihydro-4H-imidazo[4,5,1-ij]quinoline
7,8,9-tribromo-N-[3-(morpholin-4-yl)propyl]-5,6-dihydro-4H-imidazo[4,5,1-ij]quinolin-2-amine
7,8-dibromo-9-methyl-2-(4-methylpiperazin-1-yl)-5,6-dihydro-4H-imidazo[4,5,1-ij]quinoline
N,N-dimethyl-1-(7,8,9-tribromo-5,6-dihydro-4H-imidazo[4,5,1-ij]quinolin-2-yl)pyrrolidin-3-amine
7,8-dibromo-9-iodo-2-(4-methylpiperazin-1-yl)-5,6-dihydro-4H-imidazo[4,5,1-ij]quinoline
(3S)-1-(7,8,9-tribromo-5,6-dihydro-4H-imidazo[4,5,1-ij]quinolin-2-yl)pyrrolidin-3-ol
1-(7,8-dibromo-9-iodo-5,6-dihydro-4H-imidazo[4,5,1-ij]quinolin-2-yl)piperidin-4-ol
7,8-dibromo-N,N-diethyl-9-methyl-5,6-dihydro-4H-imidazo[4,5,1-ij]quinolin-2-amine
(3S)-1-(7,8-dibromo-9-methyl-5,6-dihydro-4H-imidazo[4,5,1-ij]quinolin-2-yl)pyrrolidin-3-amine
7,8-dibromo-9-methyl-2-[(2S)-2-methylpiperazin-1-yl]-5,6-dihydro-4H-imidazo[4,5,1-ij]quinoline
7,8,9-tribromo-2-(4-ethoxypiperidin-1-yl)-5,6-dihydro-4H-imidazo[4,5,1-ij]quinoline
N-[7,8-dibromo-2-(piperazin-1-yl)-5,6-dihydro-4H-imidazo[4,5,1-ij]quinolin-9-yl]acetamide
7,8,9-tribromo-2-(piperazin-1-yl)-5,6-dihydro-4H-imidazo[4,5,1-ij]quinoline maleate
7,8-dibromo-9-methyl-2-(1-methylpiperidin-4-yl)-5,6-dihydro-4H-imidazo[4,5,1-ij]quinoline hydrochloride
7,8,9-tribromo-2-(1-methylpiperidin-4-yl)-5,6-dihydro-4H-imidazo[4,5,1-ij]quinoline hydrochloride
7,8-dibromo-9-methyl-2-(piperidin-4-yl)-5,6-dihydro-4H-imidazo[4,5,1-ij]quinoline hydrochloride
7,8-dibromo-9-methyl-2-[1-(propan-2-yl)piperidin-4-yl]-5,6-dihydro-4H-imidazo[4,5,1-ij]quinoline hydrochloride
7,8,9-tribromo-2-(piperidin-4-yl)-5,6-dihydro-4H-imidazo[4,5,1-ij]quinoline hydrochloride 7,8-dibromo-9-methyl-2-(piperidin-3-yl)-5,6-dihydro-4H-imidazo[4,5,1-ij]quinoline hydrochloride
7,8-dibromo-9-methyl-2-(piperazin-2-yl)-5,6-dihydro-4H-imidazo[4,5,1-ij]quinoline hydrochloride
7,8-dibromo-2-(4-fluoro-piperidin-4-yl)-9-methyl-5,6-dihydro-4H-imidazo[4,5,1-ij]quinoline hydrochloride
2-[(2-aminoethyl)amino]-7,8-dibromo-5,6-dihydro-4H-imidazo[4,5,1-]quinoline-9-carbonitrile hydrochloride
7,8-dibromo-9-cyano-2-(piperazin-1-yl)-5,6-dihydro-4H-imidazo[4,5,1-ij]quinoline hydrochloride
7,8,9-tribromo-N-(piperidin-4-yl)-5,6-dihydro-4H-imidazo[4,5,1-ij]quinoline-2-carboxamide hydrochloride
piperazin-1-yl(7,8,9-tribromo-5,6-dihydro-4H-imidazo[4,5,1-ij]quinolin-2-yl)methanone hydrochloride
N-(2-aminoethyl)-7,8,9-tribromo-5,6-dihydro-4H-imidazo[4,5,1-ij]quinoline-2-carboxamide hydrochloride
7,8,9-tribromo-N-(2-hydroxyethyl)-5,6-dihydro-4H-imidazo[4,5,1-ij]quinoline-2-carboxamide hydrochloride
7,8-dibromo-9-methyl-2-[(3R)-3-methylpiperazin-1-yl]-5,6-dihydro-4H-imidazo[4,5,1-ij]quinoline
7,8-dibromo-9-methyl-2-(morpholin-4-yl)-5,6-dihydro-4H-imidazo[4,5,1-ij]quinoline 8. A compound according to any one of 1 to 7, wherein the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate.

9. A pharmaceutical composition comprising a compound according to any one of 1 to 8.

10. A pharmaceutical composition according to 9, wherein said composition comprises said compound as the only pharmaceutically active agent or wherein said composition comprises at least one further independent pharmaceutically active agent.

11. A pharmaceutical composition according to 9 or 10, wherein said composition is an oral, buccal, nasal, rectal, topical, transdermal and parenteral composition.

12. A pharmaceutical composition according to any one of 9 to 11, wherein said composition comprises at least one pharmaceutically acceptable excipient.

13. A pharmaceutical composition according to any one of 9 to 12 for use in the treatment of a disease selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angio sarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma [pinealoma], glioblastorna multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformians of the skull, meningioma, meningio sarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angio sarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyo sarcoma of the vagina, fallopian tubes carcinoma, breast; and malignant melanoma, basal cell carcinoma, squamous cell carcinoma, Gastrointestinal tumors, colon cancer, small and large intestine and rectum tumors, Karposi's sarcoma, moles dysplastic nevi, lipoma, angioma, dermatofibroma, keloids and bone marrow transplant rejection.

14. A pharmaceutical composition according to any one of 9 to 12 for use in the treatment of a cancer selected from a cancer of the gastrointestinal tract, preferably colorectal cancer, melanoma and lung cancer.

15. A pharmaceutical composition according to any one of 9 to 12 for use in the treatment of an autoimmune or inflammatory disease selected from the group consisting of allograft rejection, autoimmune thyroid diseases (including Graves' disease and Hashimoto's thyroiditis), autoimmune uveoretinitis, giant cell arteritis, inflammatory bowel diseases (including Crohn's disease, ulcerative colitis, asthma, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

16. A method for treating CDK8-related disorders and pathological conditions, wherein said method comprises the step of administering to a patient in need thereof a therapeutic amount of a compound according to any one of 1 to 8.

17. Use of a compound according to any one of 1 to 8 as CDK8 inhibitor for the treatment of disease selected from the group consisting of autoimmune and inflammatory diseases selected from the group consisting of allograft rejection, autoimmune thyroid diseases (including Graves' disease and Hashimoto's thyroiditis), autoimmune uveoretinitis, giant cell arteritis, inflammatory bowel diseases (including Crohn's disease, ulcerative colitis, asthma, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

18. Use of at least one CDK8 inhibitor for the treatment of a disease selected from the group consisting of autoimmune and inflammatory diseases including but not limited to allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, asthma, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

The invention claimed is:

1. A compound of formula (I)

wherein $X^1$, $X^2$ and $X^3$ are each independently selected from the group consisting of H, F, Cl, Br, I, —$OT^1$, —$N(T^2)(T^3)$, —$NHC(=O)T^4$, nitro, cyano, cyclopropyl and —$C_{1-3}$alkyl, with the proviso that at least two substituents selected from $X^1$, $X^2$ and $X^3$ are each independently selected from the group consisting of F, Cl, Br and I:

$Z^1$ and $Z^2$ are each independently selected from the group consisting of —$C_{1-6}$alkyl, —$OT^1$ and —$N(T^2)(T^3)$;

$Z^3$ and $Z^4$ are either taken together to form an oxo group at the carbon atom to which they are attached; or $Z^3$ and $Z^4$ are each independently selected from the group consisting of H, —$C_{1-6}$alkyl, —$OT^1$ and —$N(T^2)(T^3)$;

$Z^5$ and $Z^6$ are either taken together to form an oxo group at the carbon atom to which they are attached; or $Z^5$ and $Z^6$ are each independently selected from the group consisting of H, —$C_{1-6}$alkyl, —$OT^1$ and —$N(T^2)(T^3)$;

$X^4$ is absent;

$Y^1$ is piperazine, wherein said piperazine is optionally substituted with one or more substituents independently selected from F, Cl, Br, I, —$C(=O)H$, —$OT^1$, —$N(T^2)(T^3)$, —$C(=)N(T^2)(T^3)$, —$C(=O)OT^1$, —$ST^1$ and —$C_{1-3}$alkyl, wherein said —$C_{1-3}$alkyl is optionally substituted with one or more substituents independently selected from —$OT^1$ and $N(T^2)(T^3)$;

$T^1$, $T^2$ and $T^3$ are each independently selected from H and —$C_{1-6}$alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^7$, —$S(=O)_2OT^8$ and —$S(=O)_2N(T^5)(T^6)$;

$T^4$ is —$C_{1-6}$ alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^5$, $T^6$ and $T^7$ are each independently selected from H and —$C_{1-6}$ alkyl optional iv substituted with one or substituents independently selected from amino, hydroxyl, thiol, nitro and cyano; and $T^8$ is selected from —$C_{1-6}$alkyl optionally substituted with one or more substituents independently selected from amino, hydroxyl, thiol, nitro and cyano;

or a pharmaceutically acceptable salt thereof.

2. A compound according to claim 1, wherein $X^1$ is selected from the group consisting of H, F, Cl, Br, I, —$OT^1$, —$N(T^2)(T^3)$, —$NHC(=O)T^4$, nitro, cyano, cyclopropyl and —$C_{1-3}$alkyl; and $X^2$ and $X^3$ are independently selected from the group consisting of F, Cl, Br and I;

or a pharmaceutically acceptable salt thereof.

3. A compound according to claim 1, wherein said compound is selected from the group consisting of:

7,8,9-tribomo-2-(2-methylpiperazin-1-yl)-5,6-dihydro-4H-imidazo[4,5,1-ij]quinoline hydrochloride 7,8-dibrom-9-methyl-2-(piperazin-1-yl)-5,6-dihydro-4H-imidazo[4,5,1-ij]quinoline hydrochloride 7,8-dibromo-2-(piperazin-1-yl)-5,6-dihydro-4H-imidazo[4,5,1-ij]quinoline hydrochloride 8,9-dibromo-7-methyl-2-(piperazin-1-yl)-5,6-dihydro-4H-imidazo[4,5,1-ij]quinoline hydrochloride 7,8-dibromo-9-nitro-2-(piperazin-1-yl)-5,6-dihydro-4H-imidazo[4,5,1-ij]quinoline hydrochloride 7,8-dibromo-9-iodo-2-(piperazin-1-yl)-5,6-dihydro-4H-imidazo[4,5,1-ij]quinoline hydrochloride 7,8-dibromo-2-(piperazin-1-yl)-5,6-dihydro-4H-imidazo[4,5,1-ij]quinolin-9-amine hydrochloride 7,9-dibromo-8-methoxy-2-(piperazin-1-yl)-5,6-dihydro-4H-imidazo[4,5,1-ij]quinoline hydrochloride 7,8,9-tribomo-4-methyl-2-(piperazin-1-yl)-5,6-dihydro-4H-imidazo[4,5,1-ij]quinoline hydrochloride 7,9-dibromo-8-methyl-2-(piperazin-1-yl)-5,6-dihydro-4H-imidazo[4,5,1-ij]quinoline hydrochloride 7,8-dibromo-9-cyclopropyl-2-(piperazin-1-yl)-5,6-dihydro-4H-imidazo[4,5,1-ij]quinoline hydrochloride 7,8,9-tribomo-2-(4-methylpiperazin-1-yl)-5,6-dihydro-4H-imidazo[4,5,1-ij]quinoline 7,8,9-tribromo-2-(3,3-dimethylpiperazin-1-yl)-5,6-dihydro-4H-imidazo[4,5,1-ij]quinoline 7,8,9-tribromo-2-(3-methylpiperazin-1-yl)-5,6-dihydro-4H-imidazo[4,5,1-ij]quinoline 7,8-dibromo-9-iodo-2-[(3R)-3-methylpiperazin-1-yl]-5,6-dihydro-4H imidazo[4,5,1-ij]quinoline 7,8-dibromo-2-(3,3-dimethylpiperazin-1-yl)-9-iodo-5,6-dihydro-4H-imidazo[4,5,1-ij]quinoline 7,8,9-tribromo-2-[(3S)-3-methylpiperazin-1-yl]-5,6-dihydro-4H-imidazo[4,5,1-ij]quinoline 7,8,9-tribromo-2-[(3R)-3-methylpiperazin-1-yl]-5,6-dihydro-4H-imidazo[4,5,1-ij]quinoline 7,8-dibromo-9-iodo-2-[(3R)-3-methylpiperazin-1-yl]-5,6-dihydro-4H-imidazo[4,5,1-ij]quinoline 7,8-dibromo-2-[(3R,5S)-3,5-dimethylpiperazin-1-yl]-9-methyl-5,6-dihydro-4H-imidazo[4,5,1-ij]quinoline 7,8-dibromo-9-methyl-2-(3-methylpiperazin-1-yl)-5,6-dihydro-4H-imidazo[4,5,1-ij]quinoline 7,8-dibromo-2-(3,3-dimethylpiperazin-1-yl)-9-methyl-5,6-dihydro-4H-imidazo[4,5,1-ij]quinoline 7,8-dibromo-9-methyl-2-(4-methylpiperazin-1-yl)-5,6-dihydro-4H imidazo[4,5,1-ij]quinoline 7,8-dibromo-9-iodo-2-(4-methylpiperazin-1-yl)-5,6-dihydro-4H-imidazo[4,5,1-ij]quinoline 7,8-dibromo-9-methyl-2-[(2S)-2-methylpiperazin-1-yl]-5,6-dihydro-4H imidazo[4,5,1-ij]quinoline N-[7,8-dibromo-2-(piperazin-1-yl)-5,6-dihydro-4H-imidazo[4,5,1-ij]quinolin-9-yl]acetamide 7,8,9-tribromo-2-(piperazin-1-yl)-5,6-dihydro-4H-imidazo[4,5,1-ij]quinoline maleate 7,8-dibromo-9-methyl-2-(piperazin-2-yl)-5,6-dihydro-4H-imidazo[4,5,1-ij]quinoline hydrochloride 7,8-dibromo-9-cyano-2-(piperazin-1-yl)-5,6-dihydro-4H-imidazo[4,5,1-ij]quinoline hydrochloride and 7,8-dibromo-9-methyl-2-[(3R)-3-methylpiperazin-1-yl]-5,6-dihydro-4H imidazo[4,5,1-ij]quinoline;

or a pharmaceutically acceptable salt thereof.

4. A compound according to claim 1, wherein the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate.

5. A pharmaceutical composition comprising a compound according to claim 1.

6. A pharmaceutical composition according to claim 5, wherein said composition comprises said compound as the only pharmaceutically active agent or wherein said composition comprises at least one further independent pharmaceutically active agent.

7. A pharmaceutical composition according to claim 5, wherein said composition is a composition selected from the group consisting of an oral, buccal, nasal, rectal, topical, transdermal and parenteral composition.

8. A pharmaceutical composition according to claim 5, wherein said composition comprises at least one pharmaceutically acceptable excipient.

9. A method of treating a disease in a subject, comprising administering to said subject a pharmaceutical composition according to claim 5, wherein said disease is selected from the group consisting of acute myeloid leukemia lymphoma and lung cancer, Hodgkin's disease, non-Hodgkin's lymphoma (malignant lymphoma); sarcoma of the prostate, hepatocellular carcinoma, breast adenocarcinoma Gastrointestinal tumors, colon cancer, small and large intestine and rectum tumors.

10. A compound according to claim 1, wherein $Z^1$, $Z^2$, $Z^3$, $Z^4$, $Z^5$, and $Z^6$ are each independently selected from the group consisting of H, —$C_{1-6}$alkyl, —$OT^1$ and —$N(T^2)(T^3)$;

or a pharmaceutically acceptable salt thereof.

11. A compound according to claim 1, wherein $T^1$, $T^2$ and $T^3$ are each independently selected from H and —$C_{1-6}$alkyl optionally substituted with one or more substituent independently selected from —$N(T^5)(T^6)$, —$OT^7$, —$ST^7$, nitro, and cyano;

or a pharmaceutically acceptable salt thereof.

12. A compound according to claim 10, wherein $Y^1$ is piperazine, wherein said piperazine is optionally substituted with one more —$C_{1-3}$alkyl;

or a pharmaceutically acceptable salt thereof.

13. A compound according to claim 12, wherein $X^1$, $X^2$ and $X^3$ are each independently selected from the group consisting of H, F, Cl, Br, I, and —$C_{1-3}$alkyl, with the proviso that at least two substituents selected from $X^1$, $X^2$ and $X^3$ are each independently selected from the group consisting of F, Cl, Br and I;

or a pharmaceutically acceptable salt thereof.

14. A compound according to claim 13, wherein $X^2$ and $X^3$ are Br;

or a pharmaceutically acceptable salt thereof.

15. A compound according to claim 1, wherein said compound is 7,8-dibromo-9-methyl-2-(piperazin-1-yl)-5,6-dihydro-4H-imidazo[4,5,1-ij]quinoline or a pharmaceutically acceptable salt thereof.

16. A compound according to claim 1, wherein said compound is 7,8-dibromo-9-methyl-2-(piperazin-1-yl)-5,6-dihydro-4H-imidazo[4,5,1-ij]quinoline hydrochloride.

17. A compound according to claim 1, wherein said compound is 7,8,9-tribromo-2-(piperazin-1-yl)-5,6-dihydro-4H-imidazo[4,5,1-ij]quinoline or a pharmaceutically acceptable salt thereof.

18. A compound according to claim 1, wherein said compound is 7,8,9-tribromo-2-(piperazin-1-yl)-5,6-dihydro-4H-imidazo[4,5,1-ij]quinoline maleate.

* * * * *

UNITED STATES PATENT AND TRADEMARK OFFICE
CERTIFICATE OF CORRECTION

PATENT NO. : 9,745,299 B2
APPLICATION NO. : 14/441785
DATED : August 29, 2017
INVENTOR(S) : Rzymski et al.

Page 1 of 1

It is certified that error appears in the above-identified patent and that said Letters Patent is hereby corrected as shown below:

In the Claims

Claim 1
Column 126, Line 2, "N(T2)(T3)" should read -- -N(T2)(T3)--.

Claim 3
Column 126, Line 59, "6-dihydro-4H imidazo[4,5,1-ij]quinoline" should read
--6-dihydro-4H-imidazo[4,5,1-ij]quinoline--.
Column 127, Line 12, "5,6-dihydro-4H imidazo[4,5,1-ij]quinoline" should read
--5,6-dihydro-4H-imidazo[4,5,1-ij]quinoline--.
Column 127, Line 22, "5,6-dihydro-4H imidazo[4,5,1-ij]quinoline" should read
--5,6-dihydro-4H-imidazo[4,5,1-ij]quinoline--.

Signed and Sealed this
Sixteenth Day of October, 2018

Andrei Iancu
*Director of the United States Patent and Trademark Office*